(12) United States Patent
Grandi et al.

(10) Patent No.: US 11,066,453 B2
(45) Date of Patent: Jul. 20, 2021

(54) IMMUNOGENIC COMPOSITIONS CONTAINING BACTERIAL OUTER MEMBRANE VESICLES AND THERAPEUTIC USES THEREOF

(71) Applicant: UNIVERSITA' DEGLI STUDI DI TRENTO, Trento (IT)

(72) Inventors: Guido Grandi, Povo (IT); Valeria Cafardi, Povo (IT); Laura Fantappie', Povo (IT); Renata Grifantini, Siena (IT); Alberto Grandi, Siena (IT)

(73) Assignee: BIOMVIS SRL, Siena (IT)

( * ) Notice: Subject to any disclaimer, the term of this patent is extended or adjusted under 35 U.S.C. 154(b) by 0 days.

(21) Appl. No.: 15/573,920

(22) PCT Filed: May 17, 2016

(86) PCT No.: PCT/EP2016/061031
§ 371 (c)(1),
(2) Date: Nov. 14, 2017

(87) PCT Pub. No.: WO2016/184860
PCT Pub. Date: Nov. 24, 2016

(65) Prior Publication Data
US 2018/0353587 A1 Dec. 13, 2018

(30) Foreign Application Priority Data
May 18, 2015 (EP) .................................. 15168024

(51) Int. Cl.
| | | |
|---|---|---|
| *A61K 39/095* | (2006.01) | |
| *A61K 39/102* | (2006.01) | |
| *A61K 39/108* | (2006.01) | |
| *C07K 14/22* | (2006.01) | |
| *C07K 14/47* | (2006.01) | |

(52) U.S. Cl.
CPC ...... *C07K 14/4748* (2013.01); *A61K 39/0258* (2013.01); *A61K 39/095* (2013.01); *A61K 39/102* (2013.01); *C07K 14/22* (2013.01); *C07K 2319/40* (2013.01); *G01N 2333/212* (2013.01); *G01N 2333/22* (2013.01); *G01N 2333/245* (2013.01)

(58) Field of Classification Search
CPC ...... A61K 39/0225; A61K 2039/55505; A61K 2039/55566; A61K 2039/70; A61K 38/00; A61K 39/00; A61K 39/001104; C07K 14/20; C07K 16/1207; C07K 2319/00; C07K 2319/21; C07K 2319/22; C07K 2319/40; C07K 2317/73; C07K 2317/34; C07K 2317/734; C07K 14/22; C07K 14/4748; C07K 14/705; C07K 14/71; G01N 2333/20; G01N 33/56911; G01N 33/6854; G01N 2469/20; Y02A 50/401; Y02A 50/57; C12N 15/62
See application file for complete search history.

(56) References Cited

U.S. PATENT DOCUMENTS

2009/0124557 A1    5/2009    Moyal-Amsellem et al.

FOREIGN PATENT DOCUMENTS

| WO | 1999057280 A2 | 11/1999 |
|---|---|---|
| WO | 2004032958 A1 | 4/2004 |
| WO | 2006024954 A2 | 3/2006 |
| WO | 2009013115 A2 | 1/2009 |
| WO | 2014106123 A1 | 7/2014 |

OTHER PUBLICATIONS

Fang et al. Mol. Medicine Reports 10: 1056-1064, Jun. 10, 2014.*
Fantappie et al. J. Extracellular Vesicles 3: 24015, pp. 1-14, Aug. 11, 2014.*
Search Report and Written Opinion of PCT/EP2016/061031 dated Sep. 7, 2016.

* cited by examiner

Primary Examiner — Sarvamangala Devi
(74) Attorney, Agent, or Firm — Silvia Salvadori, P.C.; Silvia Salvadori

(57) ABSTRACT

The present invention provides means and products for the stimulation of an immune response against tumors in a subject in need thereof. More specifically the invention provides immunogenic compositions containing bacterial outer membrane vesicles loaded with tumor antigens, fusion proteins comprising a bacterial protein and a tumor antigen, and isolated bacterial outer membrane vesicles (OMVs) containing said fusion proteins. The fusion proteins, OMVs and immunogenic compositions according to the invention are used in the prevention and treatment of tumors.

10 Claims, 32 Drawing Sheets

Specification includes a Sequence Listing.

EGRFvIII one copy (vIII)

CTG GAA GAA AAA AAA GGT AAC TAC GTT GTT ACC GAC CAC
L   E   E   K   K   G   N   Y   V   V   T   D   H

EGRFvIII three copies (vIII3x)

CTG GAA GAA AAA AAA GGT AAC TAC GTT GTT ACC GAC CAC tct ggt
L   E   E   K   K   G   N   Y   V   V   T   D   H   S   G CTG GAA GAA AAA AAA GGT AAC TAC GTT GTT ACC GAC CAC ggc tct
L   E   E   K   K   G   N   Y   V   V   T   D   H   G   S

B

Cloning vIII 3x in pUC plasmid

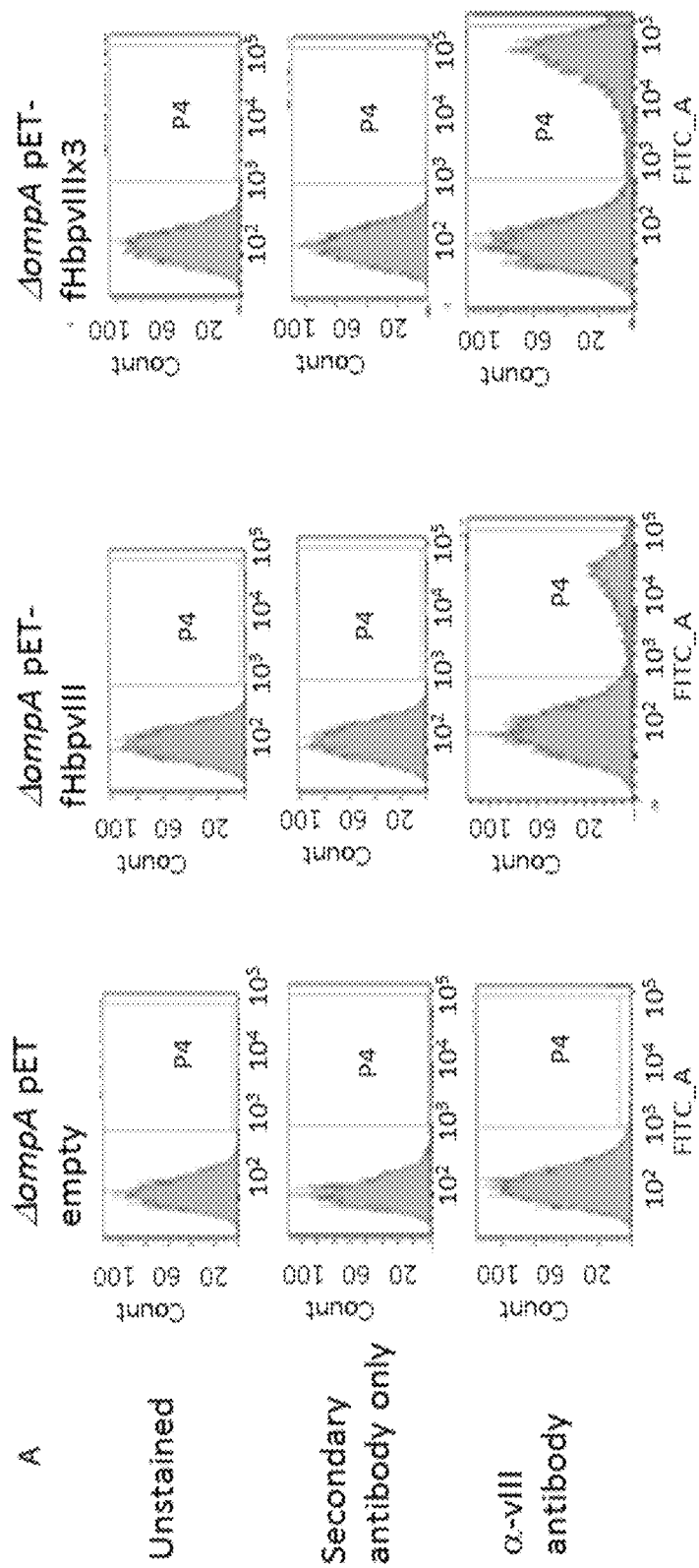

FIGURE 24

SEQUENCE LISTING

<160> NUMBER OF SEQ ID NOS: 150

<210> SEQ ID NO 1
<211> LENGTH: 274
<212> TYPE: PRT
<213> ORGANISM: Neisseria meningitidis

<400> SEQUENCE: 1

```
Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Val Tyr Lys Gln Ser His Ser Ala Leu Thr Ala Phe
            115                 120                 125

Gln Thr Glu Gln Ile Gln Asp Ser Glu His Ser Gly Lys Met Val Ala
        130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205
```

```
Asn Val Asp Leu Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
                260                 265                 270

Lys Gln

<210> SEQ ID NO 2
<211> LENGTH: 120
<212> TYPE: PRT
<213> ORGANISM: Neisseria meningitidis

<400> SEQUENCE: 2

Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Val Tyr Lys Gln
        115                 120

<210> SEQ ID NO 3
<211> LENGTH: 362
<212> TYPE: PRT
<213> ORGANISM: Escherichia coli

<400> SEQUENCE: 3

Met Met Lys Arg Asn Ile Leu Ala Val Ile Val Pro Ala Leu Leu Val
1               5                   10                  15

Ala Gly Thr Ala Asn Ala Ala Glu Ile Tyr Asn Lys Asp Gly Asn Lys
            20                  25                  30

Val Asp Leu Tyr Gly Lys Ala Val Gly Leu His Tyr Phe Ser Lys Gly
            35                  40                  45

Asn Gly Glu Asn Ser Tyr Gly Gly Asn Gly Asp Met Thr Tyr Ala Arg
        50                  55                  60

Leu Gly Phe Lys Gly Glu Thr Gln Ile Asn Ser Asp Leu Thr Gly Tyr
65                  70                  75                  80

Gly Gln Trp Glu Tyr Asn Phe Gln Gly Asn Asn Ser Glu Gly Ala Asp
                85                  90                  95

Ala Gln Thr Gly Asn Lys Thr Arg Leu Ala Phe Ala Gly Leu Lys Tyr
                100                 105                 110

Ala Asp Val Gly Ser Phe Asp Tyr Gly Arg Asn Tyr Gly Val Val Tyr
                115                 120                 125

Asp Ala Leu Gly Tyr Thr Asp Met Leu Pro Glu Phe Gly Gly Asp Thr
```

```
                    130                 135                 140
Ala Tyr Ser Asp Asp Phe Phe Val Gly Arg Val Gly Val Ala Thr
145                 150                 155                 160

Tyr Arg Asn Ser Asn Phe Phe Gly Leu Val Asp Gly Leu Asn Phe Ala
                    165                 170                 175

Val Gln Tyr Leu Gly Lys Asn Glu Arg Asp Thr Ala Arg Arg Ser Asn
                180                 185                 190

Gly Asp Gly Val Gly Gly Ser Ile Ser Tyr Glu Tyr Glu Gly Phe Gly
                195                 200                 205

Ile Val Gly Ala Tyr Gly Ala Ala Asp Arg Thr Asn Leu Gln Glu Ala
                210                 215                 220

Gln Pro Leu Gly Asn Gly Lys Lys Ala Glu Gln Trp Ala Thr Gly Leu
225                 230                 235                 240

Lys Tyr Asp Ala Asn Asn Ile Tyr Leu Ala Ala Asn Tyr Gly Glu Thr
                245                 250                 255

Arg Asn Ala Thr Pro Ile Thr Asn Lys Phe Thr Asn Thr Ser Gly Phe
                260                 265                 270

Ala Asn Lys Thr Gln Asp Val Leu Leu Val Ala Gln Tyr Gln Phe Asp
                275                 280                 285

Phe Gly Leu Arg Pro Ser Ile Ala Tyr Thr Lys Ser Lys Ala Lys Asp
    290                 295                 300

Val Glu Gly Ile Gly Asp Val Asp Leu Val Asn Tyr Phe Glu Val Gly
305                 310                 315                 320

Ala Thr Tyr Tyr Phe Asn Lys Asn Met Ser Thr Tyr Val Asp Tyr Ile
                325                 330                 335

Ile Asn Gln Ile Asp Ser Asp Asn Lys Leu Gly Val Gly Ser Asp Asp
                340                 345                 350

Thr Val Ala Val Gly Ile Val Tyr Gln Phe
                355                 360

<210> SEQ ID NO 4
<211> LENGTH: 396
<212> TYPE: PRT
<213> ORGANISM: Escherichia coli

<400> SEQUENCE: 4

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
                35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140
```

```
Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
            165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Arg Ile Thr Lys
385                 390                 395

<210> SEQ ID NO 5
<211> LENGTH: 13
<212> TYPE: PRT
<213> ORGANISM: Homo sapiens

<400> SEQUENCE: 5

Leu Glu Glu Lys Lys Gly Asn Tyr Val Val Thr Asp His
1               5                   10

<210> SEQ ID NO 6
<211> LENGTH: 25
<212> TYPE: PRT
<213> ORGANISM: Homo sapiens

<400> SEQUENCE: 6

Ile Gln Val Glu Ala Thr Asp Lys Asp Leu Gly Pro Asn Gly His Val
1               5                   10                  15

Thr Tyr Ser Ile Val Thr Asp Thr Asp
            20                  25

<210> SEQ ID NO 7
<211> LENGTH: 20
<212> TYPE: PRT
<213> ORGANISM: Homo sapiens
```

-continued

```
<400> SEQUENCE: 7

Gly Val Thr Ser Ala Pro Asp Thr Arg Pro Ala Pro Gly Ser Thr Ala
1               5                   10                  15
Pro Pro Ala His
            20

<210> SEQ ID NO 8
<211> LENGTH: 287
<212> TYPE: PRT
<213> ORGANISM: Unknown
<220> FEATURE:
<223> OTHER INFORMATION: fusion protein

<400> SEQUENCE: 8

Val Asn Arg Thr Ala Phe Cys Cys Leu Ser Leu Thr Thr Ala Leu Ile
1               5                   10                  15
Leu Thr Ala Cys Ser Ser Gly Gly Gly Val Ala Ala Asp Ile Gly
            20                  25                  30
Ala Gly Leu Ala Asp Ala Leu Thr Ala Pro Leu Asp His Lys Asp Lys
        35                  40                  45
Gly Leu Gln Ser Leu Thr Leu Asp Gln Ser Val Arg Lys Asn Glu Lys
    50                  55                  60
Leu Lys Leu Ala Ala Gln Gly Ala Glu Lys Thr Tyr Gly Asn Gly Asp
65                  70                  75                  80
Ser Leu Asn Thr Gly Lys Leu Lys Asn Asp Lys Val Ser Arg Phe Asp
                85                  90                  95
Phe Ile Arg Gln Ile Glu Val Asp Gly Gln Leu Ile Thr Leu Glu Ser
            100                 105                 110
Gly Glu Phe Gln Val Tyr Lys Gln Ser His Ser Ala Leu Thr Ala Phe
        115                 120                 125
Gln Thr Glu Gln Ile Gln Asp Ser Glu His Ser Gly Lys Met Val Ala
    130                 135                 140
Lys Arg Gln Phe Arg Ile Gly Asp Ile Ala Gly Glu His Thr Ser Phe
145                 150                 155                 160
Asp Lys Leu Pro Glu Gly Gly Arg Ala Thr Tyr Arg Gly Thr Ala Phe
                165                 170                 175
Gly Ser Asp Asp Ala Gly Gly Lys Leu Thr Tyr Thr Ile Asp Phe Ala
            180                 185                 190
Ala Lys Gln Gly Asn Gly Lys Ile Glu His Leu Lys Ser Pro Glu Leu
        195                 200                 205
Asn Val Asp Leu Ala Ala Ala Asp Ile Lys Pro Asp Gly Lys Arg His
    210                 215                 220
Ala Val Ile Ser Gly Ser Val Leu Tyr Asn Gln Ala Glu Lys Gly Ser
225                 230                 235                 240
Tyr Ser Leu Gly Ile Phe Gly Gly Lys Ala Gln Glu Val Ala Gly Ser
                245                 250                 255
Ala Glu Val Lys Thr Val Asn Gly Ile Arg His Ile Gly Leu Ala Ala
            260                 265                 270
Lys Gln Leu Glu Glu Lys Lys Gly Asn Tyr Val Val Thr Asp His
        275                 280                 285

<210> SEQ ID NO 9
<211> LENGTH: 133
<212> TYPE: PRT
<213> ORGANISM: Unknown
<220> FEATURE:
<223> OTHER INFORMATION: fusion protein
```

<400> SEQUENCE: 9

| Val | Asn | Arg | Thr | Ala | Phe | Cys | Cys | Leu | Ser | Leu | Thr | Thr | Ala | Leu | Ile |
| 1 | | | | 5 | | | | | 10 | | | | | 15 | |

| Leu | Thr | Ala | Cys | Ser | Ser | Gly | Gly | Gly | Gly | Val | Ala | Ala | Asp | Ile | Gly |
| | | | 20 | | | | | 25 | | | | | 30 | | |

| Ala | Gly | Leu | Ala | Asp | Ala | Leu | Thr | Ala | Pro | Leu | Asp | His | Lys | Asp | Lys |
| | | 35 | | | | | 40 | | | | | 45 | | | |

| Gly | Leu | Gln | Ser | Leu | Thr | Leu | Asp | Gln | Ser | Val | Arg | Lys | Asn | Glu | Lys |
| | 50 | | | | | 55 | | | | | 60 | | | | |

| Leu | Lys | Leu | Ala | Ala | Gln | Gly | Ala | Glu | Lys | Thr | Tyr | Gly | Asn | Gly | Asp |
| 65 | | | | | 70 | | | | | 75 | | | | | 80 |

| Ser | Leu | Asn | Thr | Gly | Lys | Leu | Lys | Asn | Asp | Lys | Val | Ser | Arg | Phe | Asp |
| | | | | 85 | | | | | 90 | | | | | 95 | |

| Phe | Ile | Arg | Gln | Ile | Glu | Val | Asp | Gly | Gln | Leu | Ile | Thr | Leu | Glu | Ser |
| | | | 100 | | | | | 105 | | | | | 110 | | |

| Gly | Glu | Phe | Gln | Val | Tyr | Lys | Gln | Leu | Glu | Glu | Lys | Lys | Gly | Asn | Tyr |
| | | | 115 | | | | | 120 | | | | | 125 | | |

| Val | Val | Thr | Asp | His |
| | | | 130 | |

<210> SEQ ID NO 10
<211> LENGTH: 321
<212> TYPE: PRT
<213> ORGANISM: Unknown
<220> FEATURE:
<223> OTHER INFORMATION: fusion protein

<400> SEQUENCE: 10

| Val | Asn | Arg | Thr | Ala | Phe | Cys | Cys | Leu | Ser | Leu | Thr | Thr | Ala | Leu | Ile |
| 1 | | | | 5 | | | | | 10 | | | | | 15 | |

| Leu | Thr | Ala | Cys | Ser | Ser | Gly | Gly | Gly | Gly | Val | Ala | Ala | Asp | Ile | Gly |
| | | | 20 | | | | | 25 | | | | | 30 | | |

| Ala | Gly | Leu | Ala | Asp | Ala | Leu | Thr | Ala | Pro | Leu | Asp | His | Lys | Asp | Lys |
| | | 35 | | | | | 40 | | | | | 45 | | | |

| Gly | Leu | Gln | Ser | Leu | Thr | Leu | Asp | Gln | Ser | Val | Arg | Lys | Asn | Glu | Lys |
| | 50 | | | | | 55 | | | | | 60 | | | | |

| Leu | Lys | Leu | Ala | Ala | Gln | Gly | Ala | Glu | Lys | Thr | Tyr | Gly | Asn | Gly | Asp |
| 65 | | | | | 70 | | | | | 75 | | | | | 80 |

| Ser | Leu | Asn | Thr | Gly | Lys | Leu | Lys | Asn | Asp | Lys | Val | Ser | Arg | Phe | Asp |
| | | | | 85 | | | | | 90 | | | | | 95 | |

| Phe | Ile | Arg | Gln | Ile | Glu | Val | Asp | Gly | Gln | Leu | Ile | Thr | Leu | Glu | Ser |
| | | | 100 | | | | | 105 | | | | | 110 | | |

| Gly | Glu | Phe | Gln | Val | Tyr | Lys | Gln | Ser | His | Ser | Ala | Leu | Thr | Ala | Phe |
| | | | 115 | | | | | 120 | | | | | 125 | | |

| Gln | Thr | Glu | Gln | Ile | Gln | Asp | Ser | Glu | His | Ser | Gly | Lys | Met | Val | Ala |
| | 130 | | | | | 135 | | | | | 140 | | | | |

| Lys | Arg | Gln | Phe | Arg | Ile | Gly | Asp | Ile | Ala | Gly | Glu | His | Thr | Ser | Phe |
| 145 | | | | | 150 | | | | | 155 | | | | | 160 |

| Asp | Lys | Leu | Pro | Glu | Gly | Gly | Arg | Ala | Thr | Tyr | Arg | Gly | Thr | Ala | Phe |
| | | | | 165 | | | | | 170 | | | | | 175 | |

| Gly | Ser | Asp | Asp | Ala | Gly | Gly | Lys | Leu | Thr | Tyr | Thr | Ile | Asp | Phe | Ala |
| | | | 180 | | | | | 185 | | | | | 190 | | |

| Ala | Lys | Gln | Gly | Asn | Gly | Lys | Ile | Glu | His | Leu | Lys | Ser | Pro | Glu | Leu |
| | | | 195 | | | | | 200 | | | | | 205 | | |

```
Asn Val Asp Leu Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
                260                 265                 270

Lys Gln Gly Ser Leu Glu Glu Lys Gly Asn Tyr Val Thr Asp
                275                 280                 285

His Ser Gly Leu Glu Glu Lys Lys Gly Asn Tyr Val Val Thr Asp His
    290                 295                 300

Gly Ser Leu Glu Glu Lys Lys Gly Asn Tyr Val Val Thr Asp His Ser
305                 310                 315                 320

Gly
```

<210> SEQ ID NO 11
<211> LENGTH: 167
<212> TYPE: PRT
<213> ORGANISM: Unknown
<220> FEATURE:
<223> OTHER INFORMATION: fusion protein

<400> SEQUENCE: 11

```
Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Val Tyr Lys Gln Gly Ser Leu Glu Glu Lys Lys Gly
            115                 120                 125

Asn Tyr Val Val Thr Asp His Ser Gly Leu Glu Glu Lys Lys Gly Asn
        130                 135                 140

Tyr Val Val Thr Asp His Gly Ser Leu Glu Glu Lys Lys Gly Asn Tyr
145                 150                 155                 160

Val Val Thr Asp His Ser Gly
                165
```

<210> SEQ ID NO 12
<211> LENGTH: 363
<212> TYPE: PRT
<213> ORGANISM: Unknown
<220> FEATURE:
<223> OTHER INFORMATION: fusion protein

<400> SEQUENCE: 12

```
Met Met Lys Arg Asn Ile Leu Ala Val Ile Val Pro Ala Leu Leu Val
1               5                   10                  15
```

Ala Gly Thr Ala Asn Ala Ala Glu Ile Tyr Asn Lys Asp Gly Asn Lys
            20                  25                  30

Val Asp Leu Tyr Gly Lys Ala Val Gly Leu His Tyr Phe Leu Glu Glu
        35                  40                  45

Lys Lys Gly Asn Tyr Val Val Thr Asp His Gly Asp Met Thr Tyr Ala
50                  55                  60

Arg Leu Gly Phe Lys Gly Glu Thr Gln Ile Asn Ser Asp Leu Thr Gly
65                  70                  75                  80

Tyr Gly Gln Trp Glu Tyr Asn Phe Gln Gly Asn Ser Glu Gly Ala
                85                  90                  95

Asp Ala Gln Thr Gly Asn Lys Thr Arg Leu Ala Phe Ala Gly Leu Lys
                100                 105                 110

Tyr Ala Asp Val Gly Ser Phe Asp Tyr Gly Arg Asn Tyr Gly Val Val
            115                 120                 125

Tyr Asp Ala Leu Gly Tyr Thr Asp Met Leu Pro Glu Phe Gly Gly Asp
        130                 135                 140

Thr Ala Tyr Ser Asp Asp Phe Val Gly Arg Val Gly Gly Val Ala
145                 150                 155                 160

Thr Tyr Arg Asn Ser Asn Phe Phe Gly Leu Val Asp Gly Leu Asn Phe
                165                 170                 175

Ala Val Gln Tyr Leu Gly Lys Asn Glu Arg Asp Thr Ala Arg Arg Ser
            180                 185                 190

Asn Gly Asp Gly Val Gly Gly Ser Ile Ser Tyr Glu Tyr Glu Gly Phe
        195                 200                 205

Gly Ile Val Gly Ala Tyr Gly Ala Ala Asp Arg Thr Asn Leu Gln Glu
210                 215                 220

Ala Gln Pro Leu Gly Asn Gly Lys Lys Ala Glu Gln Trp Ala Thr Gly
225                 230                 235                 240

Leu Lys Tyr Asp Ala Asn Asn Ile Tyr Leu Ala Ala Asn Tyr Gly Glu
                245                 250                 255

Thr Arg Asn Ala Thr Pro Ile Thr Asn Lys Phe Thr Asn Thr Ser Gly
            260                 265                 270

Phe Ala Asn Lys Thr Gln Asp Val Leu Leu Val Ala Gln Tyr Gln Phe
        275                 280                 285

Asp Phe Gly Leu Arg Pro Ser Ile Ala Tyr Thr Lys Ser Lys Ala Lys
290                 295                 300

Asp Val Glu Gly Ile Gly Asp Val Asp Leu Val Asn Tyr Phe Glu Val
305                 310                 315                 320

Gly Ala Thr Tyr Tyr Phe Asn Lys Asn Met Ser Thr Tyr Val Asp Tyr
                325                 330                 335

Ile Ile Asn Gln Ile Asp Ser Asp Asn Lys Leu Gly Val Gly Ser Asp
            340                 345                 350

Asp Thr Val Ala Val Gly Ile Val Tyr Gln Phe
        355                 360

<210> SEQ ID NO 13
<211> LENGTH: 397
<212> TYPE: PRT
<213> ORGANISM: Unknown
<220> FEATURE:
<223> OTHER INFORMATION: fusion protein

<400> SEQUENCE: 13

Met Met Lys Arg Asn Ile Leu Ala Val Ile Val Pro Ala Leu Leu Val
1               5                   10                  15

Ala Gly Thr Ala Asn Ala Ala Glu Ile Tyr Asn Lys Asp Gly Asn Lys
            20                  25                  30

Val Asp Leu Tyr Gly Lys Ala Val Gly Leu His Tyr Phe Gly Ser Leu
         35                  40                  45

Glu Glu Lys Lys Gly Asn Tyr Val Val Thr Asp His Ser Gly Leu Glu
     50                  55                  60

Glu Lys Lys Gly Asn Tyr Val Val Thr Asp His Gly Ser Leu Glu Glu
65                  70                  75                  80

Lys Lys Gly Asn Tyr Val Val Thr Asp His Ser Gly Gly Asp Met Thr
                 85                  90                  95

Tyr Ala Arg Leu Gly Phe Lys Gly Glu Thr Gln Ile Asn Ser Asp Leu
            100                 105                 110

Thr Gly Tyr Gly Gln Trp Glu Tyr Asn Phe Gln Gly Asn Asn Ser Glu
        115                 120                 125

Gly Ala Asp Ala Gln Thr Gly Asn Lys Thr Arg Leu Ala Phe Ala Gly
    130                 135                 140

Leu Lys Tyr Ala Asp Val Gly Ser Phe Asp Tyr Gly Arg Asn Tyr Gly
145                 150                 155                 160

Val Val Tyr Asp Ala Leu Gly Tyr Thr Asp Met Leu Pro Glu Phe Gly
                165                 170                 175

Gly Asp Thr Ala Tyr Ser Asp Asp Phe Phe Val Gly Arg Val Gly Gly
            180                 185                 190

Val Ala Thr Tyr Arg Asn Ser Asn Phe Phe Gly Leu Val Asp Gly Leu
        195                 200                 205

Asn Phe Ala Val Gln Tyr Leu Gly Lys Asn Glu Arg Asp Thr Ala Arg
    210                 215                 220

Arg Ser Asn Gly Asp Gly Val Gly Gly Ser Ile Ser Tyr Glu Tyr Glu
225                 230                 235                 240

Gly Phe Gly Ile Val Gly Ala Tyr Gly Ala Ala Asp Arg Thr Asn Leu
                245                 250                 255

Gln Glu Ala Gln Pro Leu Gly Asn Gly Lys Lys Ala Glu Gln Trp Ala
            260                 265                 270

Thr Gly Leu Lys Tyr Asp Ala Asn Asn Ile Tyr Leu Ala Ala Asn Tyr
        275                 280                 285

Gly Glu Thr Arg Asn Ala Thr Pro Ile Thr Asn Lys Phe Thr Asn Thr
    290                 295                 300

Ser Gly Phe Ala Asn Lys Thr Gln Asp Val Leu Leu Val Ala Gln Tyr
305                 310                 315                 320

Gln Phe Asp Phe Gly Leu Arg Pro Ser Ile Ala Tyr Thr Lys Ser Lys
                325                 330                 335

Ala Lys Asp Val Glu Gly Ile Gly Asp Val Asp Leu Val Asn Tyr Phe
            340                 345                 350

Glu Val Gly Ala Thr Tyr Tyr Phe Asn Lys Asn Met Ser Thr Tyr Val
        355                 360                 365

Asp Tyr Ile Ile Asn Gln Ile Asp Ser Asp Asn Lys Leu Gly Val Gly
    370                 375                 380

Ser Asp Asp Thr Val Ala Val Gly Ile Val Tyr Gln Phe
385                 390                 395

<210> SEQ ID NO 14
<211> LENGTH: 366
<212> TYPE: PRT
<213> ORGANISM: Unknown
<220> FEATURE:
<223> OTHER INFORMATION: fusion protein

<400> SEQUENCE: 14

```
Met Met Lys Arg Asn Ile Leu Ala Val Ile Val Pro Ala Leu Leu Val
1               5                   10                  15

Ala Gly Thr Ala Asn Ala Ala Glu Ile Tyr Asn Lys Asp Gly Asn Lys
            20                  25                  30

Val Asp Leu Tyr Gly Lys Ala Val Gly Leu His Tyr Phe Ser Lys Gly
        35                  40                  45

Asn Gly Glu Asn Ser Tyr Gly Gly Asn Gly Asp Met Thr Tyr Ala Arg
    50                  55                  60

Leu Gly Phe Lys Gly Glu Thr Gln Ile Asn Ser Asp Leu Thr Gly Tyr
65                  70                  75                  80

Gly Gln Trp Glu Tyr Asn Phe Gln Gly Asn Leu Glu Glu Lys Lys Gly
                85                  90                  95

Asn Tyr Val Val Thr Asp His Gly Asn Lys Thr Arg Leu Ala Phe Ala
            100                 105                 110

Gly Leu Lys Tyr Ala Asp Val Gly Ser Phe Asp Tyr Gly Arg Asn Tyr
        115                 120                 125

Gly Val Val Tyr Asp Ala Leu Gly Tyr Thr Asp Met Leu Pro Glu Phe
    130                 135                 140

Gly Gly Asp Thr Ala Tyr Ser Asp Asp Phe Phe Val Gly Arg Val Gly
145                 150                 155                 160

Gly Val Ala Thr Tyr Arg Asn Ser Asn Phe Phe Gly Leu Val Asp Gly
                165                 170                 175

Leu Asn Phe Ala Val Gln Tyr Leu Gly Lys Asn Glu Arg Asp Thr Ala
            180                 185                 190

Arg Arg Ser Asn Gly Asp Gly Val Gly Gly Ser Ile Ser Tyr Glu Tyr
        195                 200                 205

Glu Gly Phe Gly Ile Val Gly Ala Tyr Gly Ala Ala Asp Arg Thr Asn
    210                 215                 220

Leu Gln Glu Ala Gln Pro Leu Gly Asn Gly Lys Lys Ala Glu Gln Trp
225                 230                 235                 240

Ala Thr Gly Leu Lys Tyr Asp Ala Asn Asn Ile Tyr Leu Ala Ala Asn
                245                 250                 255

Tyr Gly Glu Thr Arg Asn Ala Thr Pro Ile Thr Asn Lys Phe Thr Asn
            260                 265                 270

Thr Ser Gly Phe Ala Asn Lys Thr Gln Asp Val Leu Leu Val Ala Gln
        275                 280                 285

Tyr Gln Phe Asp Phe Gly Leu Arg Pro Ser Ile Ala Tyr Thr Lys Ser
    290                 295                 300

Lys Ala Lys Asp Val Glu Gly Ile Gly Asp Val Asp Leu Val Asn Tyr
305                 310                 315                 320

Phe Glu Val Gly Ala Thr Tyr Tyr Phe Asn Lys Asn Met Ser Thr Tyr
                325                 330                 335

Val Asp Tyr Ile Ile Asn Gln Ile Asp Ser Asp Asn Lys Leu Gly Val
            340                 345                 350

Gly Ser Asp Asp Thr Val Ala Val Gly Ile Val Tyr Gln Phe
        355                 360                 365
```

<210> SEQ ID NO 15
<211> LENGTH: 367
<212> TYPE: PRT
<213> ORGANISM: Unknown
<220> FEATURE:
<223> OTHER INFORMATION: fusion protein

<400> SEQUENCE: 15

```
Met Met Lys Arg Asn Ile Leu Ala Val Ile Val Pro Ala Leu Leu Val
1               5                   10                  15

Ala Gly Thr Ala Asn Ala Ala Glu Ile Tyr Asn Lys Asp Gly Asn Lys
            20                  25                  30

Val Asp Leu Tyr Gly Lys Ala Val Gly Leu His Tyr Phe Ser Lys Gly
        35                  40                  45

Asn Gly Glu Asn Ser Tyr Gly Gly Asn Gly Asp Met Thr Tyr Ala Arg
    50                  55                  60

Leu Gly Phe Lys Gly Glu Thr Gln Ile Asn Ser Asp Leu Thr Gly Tyr
65                  70                  75                  80

Gly Gln Trp Glu Tyr Asn Phe Gln Gly Asn Asn Ser Glu Gly Ala Asp
                85                  90                  95

Ala Gln Thr Gly Asn Lys Thr Arg Leu Ala Phe Ala Gly Leu Lys Tyr
            100                 105                 110

Ala Asp Val Gly Ser Phe Asp Tyr Gly Arg Asn Tyr Gly Val Val Tyr
        115                 120                 125

Asp Ala Leu Gly Tyr Thr Asp Met Leu Pro Glu Phe Gly Gly Asp Thr
    130                 135                 140

Ala Tyr Ser Asp Asp Phe Phe Val Gly Arg Val Gly Gly Val Ala Thr
145                 150                 155                 160

Tyr Arg Asn Ser Asn Phe Phe Gly Leu Val Asp Gly Leu Asn Phe Ala
                165                 170                 175

Val Gln Tyr Leu Gly Lys Asn Leu Glu Glu Lys Lys Gly Asn Tyr Val
            180                 185                 190

Val Thr Asp His Asn Gly Asp Gly Val Gly Gly Ser Ile Ser Tyr Glu
        195                 200                 205

Tyr Glu Gly Phe Gly Ile Val Gly Ala Tyr Gly Ala Ala Asp Arg Thr
    210                 215                 220

Asn Leu Gln Glu Ala Gln Pro Leu Gly Asn Gly Lys Lys Ala Glu Gln
225                 230                 235                 240

Trp Ala Thr Gly Leu Lys Tyr Asp Ala Asn Asn Ile Tyr Leu Ala Ala
                245                 250                 255

Asn Tyr Gly Glu Thr Arg Asn Ala Thr Pro Ile Thr Asn Lys Phe Thr
            260                 265                 270

Asn Thr Ser Gly Phe Ala Asn Lys Thr Gln Asp Val Leu Leu Val Ala
        275                 280                 285

Gln Tyr Gln Phe Asp Phe Gly Leu Arg Pro Ser Ile Ala Tyr Thr Lys
    290                 295                 300

Ser Lys Ala Lys Asp Val Glu Gly Ile Gly Asp Val Asp Leu Val Asn
305                 310                 315                 320

Tyr Phe Glu Val Gly Ala Thr Tyr Tyr Phe Asn Lys Asn Met Ser Thr
                325                 330                 335

Tyr Val Asp Tyr Ile Ile Asn Gln Ile Asp Ser Asp Asn Lys Leu Gly
            340                 345                 350

Val Gly Ser Asp Asp Thr Val Ala Val Gly Ile Val Tyr Gln Phe
        355                 360                 365
```

<210> SEQ ID NO 16
<211> LENGTH: 401
<212> TYPE: PRT
<213> ORGANISM: Unknown
<220> FEATURE:
<223> OTHER INFORMATION: fusion protein

<400> SEQUENCE: 16

```
Met Met Lys Arg Asn Ile Leu Ala Val Ile Val Pro Ala Leu Leu Val
1               5                   10                  15
Ala Gly Thr Ala Asn Ala Ala Glu Ile Tyr Asn Lys Asp Gly Asn Lys
            20                  25                  30
Val Asp Leu Tyr Gly Lys Ala Val Gly Leu His Tyr Phe Ser Lys Gly
        35                  40                  45
Asn Gly Glu Asn Ser Tyr Gly Asn Gly Asp Met Thr Tyr Ala Arg
    50                  55                  60
Leu Gly Phe Lys Gly Glu Thr Gln Ile Asn Ser Asp Leu Thr Gly Tyr
65                  70                  75                  80
Gly Gln Trp Glu Tyr Asn Phe Gln Gly Asn Asn Ser Glu Gly Ala Asp
                85                  90                  95
Ala Gln Thr Gly Asn Lys Thr Arg Leu Ala Phe Ala Gly Leu Lys Tyr
            100                 105                 110
Ala Asp Val Gly Ser Phe Asp Tyr Gly Arg Asn Tyr Gly Val Val Tyr
        115                 120                 125
Asp Ala Leu Gly Tyr Thr Asp Met Leu Pro Glu Phe Gly Gly Asp Thr
    130                 135                 140
Ala Tyr Ser Asp Asp Phe Phe Val Gly Arg Val Gly Gly Val Ala Thr
145                 150                 155                 160
Tyr Arg Asn Ser Asn Phe Gly Leu Val Asp Gly Leu Asn Phe Ala
                165                 170                 175
Val Gln Tyr Leu Gly Lys Asn Gly Ser Leu Glu Glu Lys Lys Gly Asn
            180                 185                 190
Tyr Val Val Thr Asp His Ser Gly Leu Glu Glu Lys Lys Gly Asn Tyr
        195                 200                 205
Val Val Thr Asp His Gly Ser Leu Glu Glu Lys Lys Gly Asn Tyr Val
    210                 215                 220
Val Thr Asp His Ser Gly Asn Gly Asp Gly Val Gly Gly Ser Ile Ser
225                 230                 235                 240
Tyr Glu Tyr Glu Gly Phe Gly Ile Val Gly Ala Tyr Gly Ala Ala Asp
                245                 250                 255
Arg Thr Asn Leu Gln Glu Ala Gln Pro Leu Gly Asn Gly Lys Lys Ala
            260                 265                 270
Glu Gln Trp Ala Thr Gly Leu Lys Tyr Asp Ala Asn Asn Ile Tyr Leu
        275                 280                 285
Ala Ala Asn Tyr Gly Glu Thr Arg Asn Ala Thr Pro Ile Thr Asn Lys
    290                 295                 300
Phe Thr Asn Thr Ser Gly Phe Ala Asn Lys Thr Gln Asp Val Leu Leu
305                 310                 315                 320
Val Ala Gln Tyr Gln Phe Asp Phe Gly Leu Arg Pro Ser Ile Ala Tyr
                325                 330                 335
Thr Lys Ser Lys Ala Lys Asp Val Glu Gly Ile Gly Asp Val Asp Leu
            340                 345                 350
Val Asn Tyr Phe Glu Val Gly Ala Thr Tyr Tyr Phe Asn Lys Asn Met
        355                 360                 365
Ser Thr Tyr Val Asp Tyr Ile Ile Asn Gln Ile Asp Ser Asp Asn Lys
    370                 375                 380
Leu Gly Val Gly Ser Asp Asp Thr Val Ala Val Gly Ile Val Tyr Gln
385                 390                 395                 400
Phe
```

<210> SEQ ID NO 17
<211> LENGTH: 363
<212> TYPE: PRT
<213> ORGANISM: Unknown
<220> FEATURE:
<223> OTHER INFORMATION: fusion protein

<400> SEQUENCE: 17

```
Met Met Lys Arg Asn Ile Leu Ala Val Ile Val Pro Ala Leu Leu Val
 1               5                  10                  15

Ala Gly Thr Ala Asn Ala Ala Glu Ile Tyr Asn Lys Asp Gly Asn Lys
             20                  25                  30

Val Asp Leu Tyr Gly Lys Ala Val Gly Leu His Tyr Phe Ser Lys Gly
         35                  40                  45

Asn Gly Glu Asn Ser Tyr Gly Gly Asn Gly Asp Met Thr Tyr Ala Arg
     50                  55                  60

Leu Gly Phe Lys Gly Glu Thr Gln Ile Asn Ser Asp Leu Thr Gly Tyr
 65                  70                  75                  80

Gly Gln Trp Glu Tyr Asn Phe Gln Gly Asn Asn Ser Glu Gly Ala Asp
                 85                  90                  95

Ala Gln Thr Gly Asn Lys Thr Arg Leu Ala Phe Ala Gly Leu Lys Tyr
            100                 105                 110

Ala Asp Val Gly Ser Phe Asp Tyr Gly Arg Asn Tyr Gly Val Val Tyr
        115                 120                 125

Asp Ala Leu Gly Tyr Thr Asp Met Leu Pro Glu Phe Gly Gly Asp Thr
    130                 135                 140

Ala Tyr Ser Asp Asp Phe Phe Val Gly Arg Val Gly Gly Val Ala Thr
145                 150                 155                 160

Tyr Arg Asn Ser Asn Phe Phe Gly Leu Val Asp Gly Leu Asn Phe Ala
                165                 170                 175

Val Gln Tyr Leu Gly Lys Asn Glu Arg Asp Thr Ala Arg Arg Ser Asn
            180                 185                 190

Gly Asp Gly Val Gly Gly Ser Ile Ser Tyr Glu Tyr Glu Gly Phe Gly
        195                 200                 205

Ile Val Gly Ala Tyr Gly Ala Ala Asp Arg Thr Asn Leu Gln Glu Ala
    210                 215                 220

Gln Pro Leu Gly Asn Gly Lys Lys Ala Glu Gln Trp Ala Thr Gly Leu
225                 230                 235                 240

Lys Tyr Asp Ala Asn Asn Ile Tyr Leu Ala Ala Asn Tyr Gly Glu Thr
                245                 250                 255

Arg Asn Ala Thr Leu Glu Glu Lys Lys Gly Asn Tyr Val Val Thr Asp
            260                 265                 270

His Ala Asn Lys Thr Gln Asp Val Leu Leu Val Ala Gln Tyr Gln Phe
        275                 280                 285

Asp Phe Gly Leu Arg Pro Ser Ile Ala Tyr Thr Lys Ser Lys Ala Lys
    290                 295                 300

Asp Val Glu Gly Ile Gly Asp Val Asp Leu Val Asn Tyr Phe Glu Val
305                 310                 315                 320

Gly Ala Thr Tyr Tyr Phe Asn Lys Asn Met Ser Thr Tyr Val Asp Tyr
                325                 330                 335

Ile Ile Asn Gln Ile Asp Ser Asp Asn Lys Leu Gly Val Gly Ser Asp
            340                 345                 350

Asp Thr Val Ala Val Gly Ile Val Tyr Gln Phe
        355                 360
```

<210> SEQ ID NO 18
<211> LENGTH: 365
<212> TYPE: PRT
<213> ORGANISM: Unknown
<220> FEATURE:
<223> OTHER INFORMATION: fusion protein

<400> SEQUENCE: 18

```
Met Met Lys Arg Asn Ile Leu Ala Val Ile Val Pro Ala Leu Leu Val
1               5                   10                  15

Ala Gly Thr Ala Asn Ala Ala Glu Ile Tyr Asn Lys Asp Gly Asn Lys
            20                  25                  30

Val Asp Leu Tyr Gly Lys Ala Val Gly Leu His Tyr Phe Ser Lys Gly
        35                  40                  45

Asn Gly Glu Asn Ser Tyr Gly Gly Asn Gly Asp Met Thr Tyr Ala Arg
    50                  55                  60

Leu Gly Phe Lys Gly Glu Thr Gln Ile Asn Ser Asp Leu Thr Gly Tyr
65                  70                  75                  80

Gly Gln Trp Glu Tyr Asn Phe Gln Gly Asn Asn Ser Glu Gly Ala Asp
                85                  90                  95

Ala Gln Thr Gly Asn Lys Thr Arg Leu Ala Phe Ala Gly Leu Lys Tyr
            100                 105                 110

Ala Asp Val Gly Ser Phe Asp Tyr Gly Arg Asn Tyr Gly Val Val Tyr
        115                 120                 125

Asp Ala Leu Gly Tyr Thr Asp Met Leu Pro Glu Phe Gly Gly Asp Thr
    130                 135                 140

Ala Tyr Ser Asp Asp Phe Phe Val Gly Arg Val Gly Gly Val Ala Thr
145                 150                 155                 160

Tyr Arg Asn Ser Asn Phe Phe Gly Leu Val Asp Gly Leu Asn Phe Ala
                165                 170                 175

Val Gln Tyr Leu Gly Lys Asn Glu Arg Asp Thr Ala Arg Arg Ser Asn
            180                 185                 190

Gly Asp Gly Val Gly Gly Ser Ile Ser Tyr Glu Tyr Glu Gly Phe Gly
        195                 200                 205

Ile Val Gly Ala Tyr Gly Ala Ala Asp Arg Thr Asn Leu Gln Glu Ala
    210                 215                 220

Gln Pro Leu Gly Asn Gly Lys Lys Ala Glu Gln Trp Ala Thr Gly Leu
225                 230                 235                 240

Lys Tyr Asp Ala Asn Asn Ile Tyr Leu Ala Ala Asn Tyr Gly Glu Thr
                245                 250                 255

Arg Asn Ala Thr Pro Ile Thr Asn Lys Phe Thr Asn Thr Ser Gly Phe
            260                 265                 270

Ala Asn Lys Thr Gln Asp Val Leu Leu Val Ala Gln Tyr Gln Phe Asp
        275                 280                 285

Phe Gly Leu Arg Pro Ser Ile Ala Tyr Thr Lys Ser Lys Ala Lys Leu
    290                 295                 300

Glu Glu Lys Lys Gly Asn Tyr Val Val Thr Asp His Val Asn Tyr Phe
305                 310                 315                 320

Glu Val Gly Ala Thr Tyr Tyr Phe Asn Lys Asn Met Ser Thr Tyr Val
                325                 330                 335

Asp Tyr Ile Ile Asn Gln Ile Asp Ser Asp Asn Lys Leu Gly Val Gly
            340                 345                 350

Ser Asp Asp Thr Val Ala Val Gly Ile Val Tyr Gln Phe
        355                 360                 365
```

<210> SEQ ID NO 19
<211> LENGTH: 362
<212> TYPE: PRT
<213> ORGANISM: Unknown
<220> FEATURE:
<223> OTHER INFORMATION: fusion protein

<400> SEQUENCE: 19

```
Met Met Lys Arg Asn Ile Leu Ala Val Ile Val Pro Ala Leu Leu Val
1               5                   10                  15

Ala Gly Thr Ala Asn Ala Ala Glu Ile Tyr Asn Lys Asp Gly Asn Lys
            20                  25                  30

Val Asp Leu Tyr Gly Lys Ala Val Gly Leu His Tyr Phe Ser Lys Gly
        35                  40                  45

Asn Gly Glu Asn Ser Tyr Gly Asn Gly Asp Met Thr Tyr Ala Arg
    50                  55                  60

Leu Gly Phe Lys Gly Glu Thr Gln Ile Asn Ser Asp Leu Thr Gly Tyr
65                  70                  75                  80

Gly Gln Trp Glu Tyr Asn Phe Gln Gly Asn Asn Ser Glu Gly Ala Asp
                85                  90                  95

Ala Gln Thr Gly Asn Lys Thr Arg Leu Ala Phe Ala Gly Leu Lys Tyr
            100                 105                 110

Ala Asp Val Gly Ser Phe Asp Tyr Gly Arg Asn Tyr Gly Val Val Tyr
        115                 120                 125

Asp Ala Leu Gly Tyr Thr Asp Met Leu Pro Glu Phe Gly Gly Asp Thr
    130                 135                 140

Ala Tyr Ser Asp Asp Phe Phe Val Gly Arg Val Gly Gly Val Ala Thr
145                 150                 155                 160

Tyr Arg Asn Ser Asn Phe Phe Gly Leu Val Asp Gly Leu Asn Phe Ala
                165                 170                 175

Val Gln Tyr Leu Gly Lys Asn Glu Arg Asp Thr Ala Arg Arg Ser Asn
            180                 185                 190

Gly Asp Gly Val Gly Gly Ser Ile Ser Tyr Glu Tyr Glu Gly Phe Gly
        195                 200                 205

Ile Val Gly Ala Tyr Gly Ala Ala Asp Arg Thr Asn Leu Gln Glu Ala
    210                 215                 220

Gln Pro Leu Gly Asn Gly Lys Lys Ala Glu Gln Trp Ala Thr Gly Leu
225                 230                 235                 240

Lys Tyr Asp Ala Asn Asn Ile Tyr Leu Ala Ala Asn Tyr Gly Glu Thr
                245                 250                 255

Arg Asn Ala Thr Pro Ile Thr Asn Lys Phe Thr Asn Thr Ser Gly Phe
            260                 265                 270

Ala Asn Lys Thr Gln Asp Val Leu Leu Val Ala Gln Tyr Gln Phe Asp
        275                 280                 285

Phe Gly Leu Arg Pro Ser Ile Ala Tyr Thr Lys Ser Lys Ala Lys Asp
    290                 295                 300

Val Glu Gly Ile Gly Asp Val Asp Leu Val Asn Tyr Phe Glu Val Gly
305                 310                 315                 320

Ala Thr Tyr Tyr Phe Asn Lys Asn Met Ser Thr Tyr Val Asp Tyr Ile
                325                 330                 335

Ile Asn Gln Leu Glu Glu Lys Lys Gly Asn Tyr Val Val Thr Asp His
            340                 345                 350

Thr Val Ala Val Gly Ile Val Tyr Gln Phe
        355                 360
```

<210> SEQ ID NO 20
<211> LENGTH: 409
<212> TYPE: PRT
<213> ORGANISM: Unknown
<220> FEATURE:
<223> OTHER INFORMATION: fusion protein

<400> SEQUENCE: 20

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
            355                 360                 365
```

```
Val Arg Thr Ala Val Ile Asn Ala Ala Ser Gly Arg Gln Thr Val Asp
    370                 375                 380

Glu Ala Leu Lys Asp Ala Gln Thr Arg Ile Thr Lys Leu Glu Glu Lys
385                 390                 395                 400

Lys Gly Asn Tyr Val Val Thr Asp His
                405

<210> SEQ ID NO 21
<211> LENGTH: 195
<212> TYPE: PRT
<213> ORGANISM: Unknown
<220> FEATURE:
<223> OTHER INFORMATION: fusion protein

<400> SEQUENCE: 21

Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Val Tyr Lys Gln Ile Gln Val Glu Ala Thr Asp Lys
            115                 120                 125

Asp Leu Gly Pro Asn Gly His Val Thr Tyr Ser Ile Val Thr Asp Thr
        130                 135                 140

Asp Ile Gln Val Glu Ala Thr Asp Lys Asp Leu Gly Pro Asn Gly His
145                 150                 155                 160

Val Thr Tyr Ser Ile Val Thr Asp Thr Asp Ile Gln Val Glu Ala Thr
                165                 170                 175

Asp Lys Asp Leu Gly Pro Asn Gly His Val Thr Tyr Ser Ile Val Thr
            180                 185                 190

Asp Thr Asp
        195

<210> SEQ ID NO 22
<211> LENGTH: 349
<212> TYPE: PRT
<213> ORGANISM: Unknown
<220> FEATURE:
<223> OTHER INFORMATION: fusion protein

<400> SEQUENCE: 22

Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
```

```
            50                  55                  60
Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln Ile Gln Val Glu Ala Thr Asp Lys Asp Leu Gly Pro Asn Gly
        275                 280                 285

His Val Thr Tyr Ser Ile Val Thr Asp Thr Asp Ile Gln Val Glu Ala
    290                 295                 300

Thr Asp Lys Asp Leu Gly Pro Asn Gly His Val Thr Tyr Ser Ile Val
305                 310                 315                 320

Thr Asp Thr Asp Ile Gln Val Glu Ala Thr Asp Lys Asp Leu Gly Pro
                325                 330                 335

Asn Gly His Val Thr Tyr Ser Ile Val Thr Asp Thr Asp
            340                 345

<210> SEQ ID NO 23
<211> LENGTH: 471
<212> TYPE: PRT
<213> ORGANISM: Unknown
<220> FEATURE:
<223> OTHER INFORMATION: fusion protein

<400> SEQUENCE: 23

Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
                 20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
```

```
            65                  70                  75                  80
Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
            130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
                195                 200                 205

Val Asp Asn Ala Gly Ala Lys Ala Gly Leu Thr Phe Leu Val Asp Leu
            210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Arg Ile Thr Lys Ile Gln Val Glu
385                 390                 395                 400

Ala Thr Asp Lys Asp Leu Gly Pro Asn Gly His Val Thr Tyr Ser Ile
                405                 410                 415

Val Thr Asp Thr Asp Ile Gln Val Glu Ala Thr Asp Lys Asp Leu Gly
            420                 425                 430

Pro Asn Gly His Val Thr Tyr Ser Ile Val Thr Asp Thr Asp Ile Gln
            435                 440                 445

Val Glu Ala Thr Asp Lys Asp Leu Gly Pro Asn Gly His Val Thr Tyr
            450                 455                 460

Ser Ile Val Thr Asp Thr Asp
465                 470

<210> SEQ ID NO 24
```

<211> LENGTH: 220
<212> TYPE: PRT
<213> ORGANISM: Unknown
<220> FEATURE:
<223> OTHER INFORMATION: fusion protein

<400> SEQUENCE: 24

Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Gly Val Thr Ser Ala Pro Asp Thr
        115                 120                 125

Arg Pro Ala Pro Gly Ser Thr Ala Pro Pro Ala His Gly Val Thr Ser
    130                 135                 140

Ala Pro Asp Thr Arg Pro Ala Pro Gly Ser Thr Ala Pro Pro Ala His
145                 150                 155                 160

Gly Val Thr Ser Ala Pro Asp Thr Arg Pro Ala Pro Gly Ser Thr Ala
                165                 170                 175

Pro Pro Ala His Gly Val Thr Ser Ala Pro Asp Thr Arg Pro Ala Pro
            180                 185                 190

Gly Ser Thr Ala Pro Pro Ala His Gly Val Thr Ser Ala Pro Asp Thr
        195                 200                 205

Arg Pro Ala Pro Gly Ser Thr Ala Pro Pro Ala His
    210                 215                 220

<210> SEQ ID NO 25
<211> LENGTH: 496
<212> TYPE: PRT
<213> ORGANISM: Unknown
<220> FEATURE:
<223> OTHER INFORMATION: fusion protein

<400> SEQUENCE: 25

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln

```
                100            105             110
Asp Lys Leu Tyr Pro Phe Thr Trp Asp Ala Val Arg Tyr Asn Gly Lys
            115                 120                 125
Leu Ile Ala Tyr Pro Ile Ala Val Glu Ala Leu Ser Leu Ile Tyr Asn
        130                 135                 140
Lys Asp Leu Leu Pro Asn Pro Pro Lys Thr Trp Glu Glu Ile Pro Ala
145                 150                 155                 160
Leu Asp Lys Glu Leu Lys Ala Lys Gly Lys Ser Ala Leu Met Phe Asn
                165                 170                 175
Leu Gln Glu Pro Tyr Phe Thr Trp Pro Leu Ile Ala Ala Asp Gly Gly
            180                 185                 190
Tyr Ala Phe Lys Tyr Glu Asn Gly Lys Tyr Asp Ile Lys Asp Val Gly
        195                 200                 205
Val Asp Asn Ala Gly Ala Lys Ala Gly Leu Thr Phe Leu Val Asp Leu
    210                 215                 220
Ile Lys Asn Lys His Met Asn Ala Asp Thr Asp Tyr Ser Ile Ala Glu
225                 230                 235                 240
Ala Ala Phe Asn Lys Gly Glu Thr Ala Met Thr Ile Asn Gly Pro Trp
                245                 250                 255
Ala Trp Ser Asn Ile Asp Thr Ser Lys Val Asn Tyr Gly Val Thr Val
            260                 265                 270
Leu Pro Thr Phe Lys Gly Gln Pro Ser Lys Pro Phe Val Gly Val Leu
        275                 280                 285
Ser Ala Gly Ile Asn Ala Ala Ser Pro Asn Lys Glu Leu Ala Lys Glu
    290                 295                 300
Phe Leu Glu Asn Tyr Leu Leu Thr Asp Glu Gly Leu Glu Ala Val Asn
305                 310                 315                 320
Lys Asp Lys Pro Leu Gly Ala Val Ala Leu Lys Ser Tyr Glu Glu Glu
                325                 330                 335
Leu Ala Lys Asp Pro Arg Ile Ala Ala Thr Met Glu Asn Ala Gln Lys
            340                 345                 350
Gly Glu Ile Met Pro Asn Ile Pro Gln Met Ser Ala Phe Trp Tyr Ala
        355                 360                 365
Val Arg Thr Ala Val Ile Asn Ala Ala Ser Gly Arg Gln Thr Val Asp
    370                 375                 380
Glu Ala Leu Lys Asp Ala Gln Thr Arg Ile Thr Lys Gly Val Thr Ser
385                 390                 395                 400
Ala Pro Asp Thr Arg Pro Ala Pro Gly Ser Thr Ala Pro Pro Ala His
                405                 410                 415
Gly Val Thr Ser Ala Pro Asp Thr Arg Pro Ala Pro Gly Ser Thr Ala
            420                 425                 430
Pro Pro Ala His Gly Val Thr Ser Ala Pro Asp Thr Arg Pro Ala Pro
        435                 440                 445
Gly Ser Thr Ala Pro Pro Ala His Gly Val Thr Ser Ala Pro Asp Thr
    450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
                485                 490                 495

<210> SEQ ID NO 26
<211> LENGTH: 39
<212> TYPE: DNA
<213> ORGANISM: Unknown
```

-continued

<220> FEATURE:
<223> OTHER INFORMATION: oligonucleotide primer

<400> SEQUENCE: 26
gtgatggtga tgttattagc cggaatggtc ggtaaccac                                    39

<210> SEQ ID NO 27
<211> LENGTH: 39
<212> TYPE: DNA
<213> ORGANISM: Unknown
<220> FEATURE:
<223> OTHER INFORMATION: Oligonucleotide primer

<400> SEQUENCE: 27
ccaagtatac aaacaaggtt ccctggaaga aagaaggg                                     39

<210> SEQ ID NO 28
<211> LENGTH: 38
<212> TYPE: DNA
<213> ORGANISM: Unknown
<220> FEATURE:
<223> OTHER INFORMATION: oligonucleotide primer

<400> SEQUENCE: 28
cttgccgcca agcaaggttc cctggaagaa aagaaggg                                     38

<210> SEQ ID NO 29
<211> LENGTH: 57
<212> TYPE: DNA
<213> ORGANISM: Unknown
<220> FEATURE:
<223> OTHER INFORMATION: oligonucleotide primer

<400> SEQUENCE: 29
aacgtagtta cctttttttt cttccagttg tttgtatact tggaactctc cactctc               57

<210> SEQ ID NO 30
<211> LENGTH: 47
<212> TYPE: DNA
<213> ORGANISM: Unknown
<220> FEATURE:
<223> OTHER INFORMATION: oligonucleotide primer

<400> SEQUENCE: 30
ttaaacgtag ttaccttttt tttcttccag ttgcttggcg gcaaggc                           47

<210> SEQ ID NO 31
<211> LENGTH: 59
<212> TYPE: DNA
<213> ORGANISM: Unknown
<220> FEATURE:
<223> OTHER INFORMATION: oligonucleotide primer

<400> SEQUENCE: 31
aaaggtaact acgttgttac cgaccactaa catcaccatc accatcacga ttacaaaga             59

<210> SEQ ID NO 32
<211> LENGTH: 45
<212> TYPE: DNA
<213> ORGANISM: Unknown
<220> FEATURE:
<223> OTHER INFORMATION: oligonucleotide primer

<400> SEQUENCE: 32
gtgatggtga tgttattgtt tgtatacttg gaactctcca ctctc                             45

<210> SEQ ID NO 33
<211> LENGTH: 35
<212> TYPE: DNA
<213> ORGANISM: Unknown
<220> FEATURE:
<223> OTHER INFORMATION: oligonucleotide primer

<400> SEQUENCE: 33
gtgatggtga tgttattatt gcttggcggc aaggc                        35

<210> SEQ ID NO 34
<211> LENGTH: 20
<212> TYPE: DNA
<213> ORGANISM: Unknown
<220> FEATURE:
<223> OTHER INFORMATION: oligonucleotide primer

<400> SEQUENCE: 34
ttattgcttg gcggcaaggc                                          20

<210> SEQ ID NO 35
<211> LENGTH: 30
<212> TYPE: DNA
<213> ORGANISM: Unknown
<220> FEATURE:
<223> OTHER INFORMATION: oligonucleotide primer

<400> SEQUENCE: 35
ttgtttgtat acttggaact ctccactctc                               30

<210> SEQ ID NO 36
<211> LENGTH: 40
<212> TYPE: DNA
<213> ORGANISM: Unknown
<220> FEATURE:
<223> OTHER INFORMATION: oligonucleotide primer

<400> SEQUENCE: 36
ggagatatac atatggtgaa tcgaactgcc ttctgctgcc                    40

<210> SEQ ID NO 37
<211> LENGTH: 30
<212> TYPE: DNA
<213> ORGANISM: Unknown
<220> FEATURE:
<223> OTHER INFORMATION: oligonucleotide primer

<400> SEQUENCE: 37
catatgtata tctccttctt aaagttaaac                               30

<210> SEQ ID NO 38
<211> LENGTH: 32
<212> TYPE: DNA
<213> ORGANISM: Unknown
<220> FEATURE:
<223> OTHER INFORMATION: oligonucleotide primer

<400> SEQUENCE: 38
taacatcacc atcaccatca cgattacaaa ga                            32

<210> SEQ ID NO 39
<211> LENGTH: 37
<212> TYPE: DNA
<213> ORGANISM: Unknown
<220> FEATURE:
<223> OTHER INFORMATION: oligonucleotide primer

```
<400> SEQUENCE: 39
ggaattccat atgaaaataa aaacaggtgc acgcatc                              37

<210> SEQ ID NO 40
<211> LENGTH: 37
<212> TYPE: DNA
<213> ORGANISM: Unknown
<220> FEATURE:
<223> OTHER INFORMATION: oligonucleotide primer

<400> SEQUENCE: 40 ccttttttt cttccagctt ggtgatacga gtctgcg                               37

<210> SEQ ID NO 41
<211> LENGTH: 39
<212> TYPE: DNA
<213> ORGANISM: Unknown
<220> FEATURE:
<223> OTHER INFORMATION: oligonucleotide primer

<400> SEQUENCE: 41
taacaacgta gttaccttt ttttcttcca gcttggtga                             39

<210> SEQ ID NO 42
<211> LENGTH: 51
<212> TYPE: DNA
<213> ORGANISM: Unknown
<220> FEATURE:
<223> OTHER INFORMATION: oligonucleotide primer

<400> SEQUENCE: 42
ccccgctcga gttagtggtc ggtaacaacg tagttacctt tttttcttc c               51

<210> SEQ ID NO 43
<211> LENGTH: 39
<212> TYPE: DNA
<213> ORGANISM: Unknown
<220> FEATURE:
<223> OTHER INFORMATION: oligonucleotide primer

<400> SEQUENCE: 43
ggagatatac atatgaaaat aaaaacaggt gcacgcatc                            39

<210> SEQ ID NO 44
<211> LENGTH: 52
<212> TYPE: DNA
<213> ORGANISM: Unknown
<220> FEATURE:
<223> OTHER INFORMATION: oligonucleotide primer

<400> SEQUENCE: 44
gtgatggtga tgttagtggt cggtaacaac gtagttacct tttttttctt cc             52

<210> SEQ ID NO 45
<211> LENGTH: 33
<212> TYPE: DNA
<213> ORGANISM: Unknown
<220> FEATURE:
<223> OTHER INFORMATION: oligonucleotide primer

<400> SEQUENCE: 45
ggaattccat atgatgaagc gcaatattct ggc                                  33

<210> SEQ ID NO 46
```

```
<211> LENGTH: 35
<212> TYPE: DNA
<213> ORGANISM: Unknown
<220> FEATURE:
<223> OTHER INFORMATION: oligonucleotide primer

<400> SEQUENCE: 46
ccccgctcga gttagaactg gtaaacgata cccac                              35

<210> SEQ ID NO 47
<211> LENGTH: 35
<212> TYPE: DNA
<213> ORGANISM: Unknown
<220> FEATURE:
<223> OTHER INFORMATION: oligonucleotide primer

<400> SEQUENCE: 47
ggagatatac atatgatgaa gcgcaatatt ctggc                              35

<210> SEQ ID NO 48
<211> LENGTH: 36
<212> TYPE: DNA
<213> ORGANISM: Unknown
<220> FEATURE:
<223> OTHER INFORMATION: oligonucleotide primer

<400> SEQUENCE: 48
gtgatggtga tgttagaact ggtaaacgat acccac                             36

<210> SEQ ID NO 49
<211> LENGTH: 46
<212> TYPE: DNA
<213> ORGANISM: Unknown
<220> FEATURE:
<223> OTHER INFORMATION: oligonucleotide primer

<400> SEQUENCE: 49
aaaggtaact acgttgttac cgaccacggc gacatgacct atgccc                  46

<210> SEQ ID NO 50
<211> LENGTH: 55
<212> TYPE: DNA
<213> ORGANISM: Unknown
<220> FEATURE:
<223> OTHER INFORMATION: oligonucleotide primer

<400> SEQUENCE: 50
aacgtagtta cctttttttt cttccagaaa ataatgcaga ccaacagctt taccg        55

<210> SEQ ID NO 51
<211> LENGTH: 47
<212> TYPE: DNA
<213> ORGANISM: Unknown
<220> FEATURE:
<223> OTHER INFORMATION: oligonucleotide primer

<400> SEQUENCE: 51
aaaggtaact acgttgttac cgaccacggt aacaaaacgc gtctggc                 47

<210> SEQ ID NO 52
<211> LENGTH: 52
<212> TYPE: DNA
<213> ORGANISM: Unknown
<220> FEATURE:
<223> OTHER INFORMATION: oligonucleotide primer

<400> SEQUENCE: 52
```
aacgtagtta cctttttttt cttccaggtt accctggaag ttatattccc ac            52

<210> SEQ ID NO 53
<211> LENGTH: 45
<212> TYPE: DNA
<213> ORGANISM: Unknown
<220> FEATURE:
<223> OTHER INFORMATION: oligonucleotide primer

<400> SEQUENCE: 53
aaaggtaact acgttgttac cgaccacaac ggcgacggtg ttggc                   45

<210> SEQ ID NO 54
<211> LENGTH: 51
<212> TYPE: DNA
<213> ORGANISM: Unknown
<220> FEATURE:
<223> OTHER INFORMATION: oligonucleotide primer

<400> SEQUENCE: 54
aacgtagtta cctttttttt cttccaggtt tttacccagg tactgaacag c             51

<210> SEQ ID NO 55
<211> LENGTH: 51
<212> TYPE: DNA
<213> ORGANISM: Unknown
<220> FEATURE:
<223> OTHER INFORMATION: oligonucleotide primer

<400> SEQUENCE: 55
aaaggtaact acgttgttac cgaccacgcc aacaaaacgc aagacgttct g             51

<210> SEQ ID NO 56
<211> LENGTH: 48
<212> TYPE: DNA
<213> ORGANISM: Unknown
<220> FEATURE:
<223> OTHER INFORMATION: oligonucleotide primer

<400> SEQUENCE: 56
aacgtagtta cctttttttt cttccagcgt agcgttacgg gtttcacc                48

<210> SEQ ID NO 57
<211> LENGTH: 49
<212> TYPE: DNA
<213> ORGANISM: Unknown
<220> FEATURE:
<223> OTHER INFORMATION: oligonucleotide primer

<400> SEQUENCE: 57
aaaggtaact acgttgttac cgaccacgtg aactactttg aagtgggcg                49

<210> SEQ ID NO 58
<211> LENGTH: 54
<212> TYPE: DNA
<213> ORGANISM: Unknown
<220> FEATURE:
<223> OTHER INFORMATION: oligonucleotide primer

<400> SEQUENCE: 58
aacgtagtta cctttttttt cttccagttt cgctttagat ttggtgtaag cgat          54

<210> SEQ ID NO 59
<211> LENGTH: 48
<212> TYPE: DNA

<213> ORGANISM: Unknown
<220> FEATURE:
<223> OTHER INFORMATION: oligonucleotide primer

<400> SEQUENCE: 59
aaaggtaact acgttgttac cgaccacacc gttgctgtgg gtatcgtt         48

<210> SEQ ID NO 60
<211> LENGTH: 53
<212> TYPE: DNA
<213> ORGANISM: Unknown
<220> FEATURE:
<223> OTHER INFORMATION: oligonucleotide primer

<400> SEQUENCE: 60
aacgtagtta ccttttttt cttccagctg gttgatgatg tagtcaacat agg    53

<210> SEQ ID NO 61
<211> LENGTH: 38
<212> TYPE: DNA
<213> ORGANISM: Unknown
<220> FEATURE:
<223> OTHER INFORMATION: oligonucleotide primer

<400> SEQUENCE: 61
ggtctgcatt attttggttc cctggaagaa aagaaggg                    38

<210> SEQ ID NO 62
<211> LENGTH: 33
<212> TYPE: DNA
<213> ORGANISM: Unknown
<220> FEATURE:
<223> OTHER INFORMATION: oligonucleotide primer

<400> SEQUENCE: 62
ggtcatgtcg ccgccggaat ggtcggtaac cac                         33

<210> SEQ ID NO 63
<211> LENGTH: 33
<212> TYPE: DNA
<213> ORGANISM: Unknown
<220> FEATURE:
<223> OTHER INFORMATION: oligonucleotide primer

<400> SEQUENCE: 63
gggtaaaaac ggttccctgg aagaaaagaa ggg                         33

<210> SEQ ID NO 64
<211> LENGTH: 32
<212> TYPE: DNA
<213> ORGANISM: Unknown
<220> FEATURE:
<223> OTHER INFORMATION: oligonucleotide primer

<400> SEQUENCE: 64
ccgtcgccgt tgccggaatg gtcggtaacc ac                          32

<210> SEQ ID NO 65
<211> LENGTH: 20
<212> TYPE: DNA
<213> ORGANISM: Unknown
<220> FEATURE:
<223> OTHER INFORMATION: oligonucleotide primer

<400> SEQUENCE: 65
ggcgacatga cctatgcccg                                        20

-continued

```
<210> SEQ ID NO 66
<211> LENGTH: 28
<212> TYPE: DNA
<213> ORGANISM: Unknown
<220> FEATURE:
<223> OTHER INFORMATION: oligonucleotide primer

<400> SEQUENCE: 66
aaaataatgc agaccaacag ctttaccg                                          28

<210> SEQ ID NO 67
<211> LENGTH: 20
<212> TYPE: DNA
<213> ORGANISM: Unknown
<220> FEATURE:
<223> OTHER INFORMATION: oligonucleotide primer

<400> SEQUENCE: 67
aacggcgacg gtgttggcgg                                                   20

<210> SEQ ID NO 68
<211> LENGTH: 24
<212> TYPE: DNA
<213> ORGANISM: Unknown
<220> FEATURE:
<223> OTHER INFORMATION: oligonucleotide primer

<400> SEQUENCE: 68
gtttttaccc aggtactgaa cagc                                              24

<210> SEQ ID NO 69
<211> LENGTH: 32
<212> TYPE: DNA
<213> ORGANISM: Unknown
<220> FEATURE:
<223> OTHER INFORMATION: oligonucleotide primer

<400> SEQUENCE: 69
taacatcacc atcaccatca cgattacaaa ga                                     32

<210> SEQ ID NO 70
<211> LENGTH: 20
<212> TYPE: DNA
<213> ORGANISM: Unknown
<220> FEATURE:
<223> OTHER INFORMATION: oligonucleotide primer

<400> SEQUENCE: 70
ttattgcttg gcggcaaggc                                                   20

<210> SEQ ID NO 71
<211> LENGTH: 30
<212> TYPE: DNA
<213> ORGANISM: Unknown
<220> FEATURE:
<223> OTHER INFORMATION: oligonucleotide primer

<400> SEQUENCE: 71
ttgtttgtat acttggaact ctccactctc                                        30

<210> SEQ ID NO 72
<211> LENGTH: 24
<212> TYPE: DNA
<213> ORGANISM: Unknown
<220> FEATURE:
```

<223> OTHER INFORMATION: oligonucleotide primer

<400> SEQUENCE: 72
catcaccatc accatcacga ttac                                    24

<210> SEQ ID NO 73
<211> LENGTH: 24
<212> TYPE: DNA
<213> ORGANISM: Unknown
<220> FEATURE:
<223> OTHER INFORMATION: oligonucleotide primer

<400> SEQUENCE: 73
cttggtgata cgagtctgcg cgtc                                    24

<210> SEQ ID NO 74
<211> LENGTH: 45
<212> TYPE: DNA
<213> ORGANISM: Unknown
<220> FEATURE:
<223> OTHER INFORMATION: oligonucleotide primer

<400> SEQUENCE: 74
attcaagtgg aagcgactga caaagatctg ggcccgaatg gccat             45

<210> SEQ ID NO 75
<211> LENGTH: 45
<212> TYPE: DNA
<213> ORGANISM: Unknown
<220> FEATURE:
<223> OTHER INFORMATION: oligonucleotide primer

<400> SEQUENCE: 75
atctgtatcc gtaacgattg aataagttac atggccattc gggcc             45

<210> SEQ ID NO 76
<211> LENGTH: 48
<212> TYPE: DNA
<213> ORGANISM: Unknown
<220> FEATURE:
<223> OTHER INFORMATION: oligonucleotide primer

<400> SEQUENCE: 76
acggatacag atatccaggt agaggcaacc gataaagatt taggtccc          48

<210> SEQ ID NO 77
<211> LENGTH: 48
<212> TYPE: DNA
<213> ORGANISM: Unknown
<220> FEATURE:
<223> OTHER INFORMATION: oligonucleotide primer

<400> SEQUENCE: 77
ggtatccgtt acgatactat atgtgacgtg gccattggga cctaaatc          48

<210> SEQ ID NO 78
<211> LENGTH: 51
<212> TYPE: DNA
<213> ORGANISM: Unknown
<220> FEATURE:
<223> OTHER INFORMATION: oligonucleotide primer

<400> SEQUENCE: 78
gtaacggata ccgacattca ggtggaagct accgataaag acctgggtcc g       51

```
<210> SEQ ID NO 79
<211> LENGTH: 51
<212> TYPE: DNA
<213> ORGANISM: Unknown
<220> FEATURE:
<223> OTHER INFORMATION: oligonucleotide primer

<400> SEQUENCE: 79
atctgtatcg gtaacaatag aatacgtcac gtgaccattc ggacccaggt c          51

<210> SEQ ID NO 80
<211> LENGTH: 30
<212> TYPE: DNA
<213> ORGANISM: Unknown
<220> FEATURE:
<223> OTHER INFORMATION: oligonucleotide primer

<400> SEQUENCE: 80
cttgccgcca agcaaattca agtggaagcg                                  30

<210> SEQ ID NO 81
<211> LENGTH: 30
<212> TYPE: DNA
<213> ORGANISM: Unknown
<220> FEATURE:
<223> OTHER INFORMATION: oligonucleotide primer

<400> SEQUENCE: 81
caagtataca aacaaattca agtggaagcg                                  30

<210> SEQ ID NO 82
<211> LENGTH: 36
<212> TYPE: DNA
<213> ORGANISM: Unknown
<220> FEATURE:
<223> OTHER INFORMATION: oligonucleotide primer

<400> SEQUENCE: 82
gtgatggtga tggtgatgtt aatctgtatc ggtaac                           36

<210> SEQ ID NO 83
<211> LENGTH: 37
<212> TYPE: DNA
<213> ORGANISM: Unknown
<220> FEATURE:
<223> OTHER INFORMATION: oligonucleotide primer

<400> SEQUENCE: 83
cgcgcagact cgtatcacca agattcaagt ggaagcg                          37

<210> SEQ ID NO 84
<211> LENGTH: 38
<212> TYPE: DNA
<213> ORGANISM: Unknown
<220> FEATURE:
<223> OTHER INFORMATION: oligonucleotide primer

<400> SEQUENCE: 84
tcgtgatggt gatggtgatg ttaatgcgcc ggcggagc                         38

<210> SEQ ID NO 85
<211> LENGTH: 825
<212> TYPE: DNA
<213> ORGANISM: Neisseria meningitidis

<400> SEQUENCE: 85
```

```
gtgaatcgaa ctgccttctg ctgcctttct ctgaccactg ccctgattct gaccgcctgc    60
agcagcggag ggggtggtgt cgccgccgac atcggtgcgg ggcttgccga tgcactaacc   120
gcaccgctcg accataaaga caaaggtttg cagtctttga cgctggatca gtccgtcagg   180
aaaaacgaga aactgaagct ggcggcacaa ggtgcggaaa aaacttatgg aaacggtgac   240
agcctcaata cgggcaaatt gaagaacgac aaggtcagcc gtttcgactt tatccgccaa   300
atcgaagtgg acgggcagct cattaccttg gagagtggag agttccaagt atacaaacaa   360
agccattccg ccttaaccgc cttcagacc gagcaaatac aagattcgga gcattccggg    420
aagatggttg cgaaacgcca gttcagaatc ggcgacatag cgggcgaaca tacatctttt   480
gacaagcttc ccgaaggcgg cagggcgaca tatcgcggga cggcgttcgg ttcagacgat   540
gccggcggaa aactgaccta caccatagat ttcgccgcca agcagggaaa cggcaaaatc   600
gaacatttga atcgccaga actcaatgtc gacctggccg ccgccgatat caagccggat    660
ggaaaacgcc atgccgtcat cagcggttcc gtcctttaca accaagccga gaaaggcagt   720
tactccctcg gtatctttgg cggaaaaagcc caggaagttg ccggcagcgc ggaagtgaaa   780
accgtaaacg gcatacgcca tatcggcctt gccgccaagc aataa                   825
```

<210> SEQ ID NO 86
<211> LENGTH: 363
<212> TYPE: DNA
<213> ORGANISM: Neisseria meningitidis

<400> SEQUENCE: 86

```
gtgaatcgaa ctgccttctg ctgcctttct ctgaccactg ccctgattct gaccgcctgc    60
agcagcggag ggggtggtgt cgccgccgac atcggtgcgg ggcttgccga tgcactaacc   120
gcaccgctcg accataaaga caaaggtttg cagtctttga cgctggatca gtccgtcagg   180
aaaaacgaga aactgaagct ggcggcacaa ggtgcggaaa aaacttatgg aaacggtgac   240
agcctcaata cgggcaaatt gaagaacgac aaggtcagcc gtttcgactt tatccgccaa   300
atcgaagtgg acgggcagct cattaccttg gagagtggag agttccaagt atacaaacaa   360
taa                                                                 363
```

<210> SEQ ID NO 87
<211> LENGTH: 864
<212> TYPE: DNA
<213> ORGANISM: Unknown
<220> FEATURE:
<223> OTHER INFORMATION: fusion gene

<400> SEQUENCE: 87

```
gtgaatcgaa ctgccttctg ctgcctttct ctgaccactg ccctgattct gaccgcctgc    60
agcagcggag ggggtggtgt cgccgccgac atcggtgcgg ggcttgccga tgcactaacc   120
gcaccgctcg accataaaga caaaggtttg cagtctttga cgctggatca gtccgtcagg   180
aaaaacgaga aactgaagct ggcggcacaa ggtgcggaaa aaacttatgg aaacggtgac   240
agcctcaata cgggcaaatt gaagaacgac aaggtcagcc gtttcgactt tatccgccaa   300
atcgaagtgg acgggcagct cattaccttg gagagtggag agttccaagt atacaaacaa   360
agccattccg ccttaaccgc cttcagacc gagcaaatac aagattcgga gcattccggg    420
aagatggttg cgaaacgcca gttcagaatc ggcgacatag cgggcgaaca tacatctttt   480
gacaagcttc ccgaaggcgg cagggcgaca tatcgcggga cggcgttcgg ttcagacgat   540
gccggcggaa aactgaccta caccatagat ttcgccgcca agcagggaaa cggcaaaatc   600
```

```
gaacatttga aatcgccaga actcaatgtc gacctggccg ccgccgatat caagccggat    660
ggaaaacgcc atgccgtcat cagcggttcc gtcctttaca accaagccga aaaggcagt    720 tactccctcg gtatctttgg cggaaaagcc caggaagttg ccggcagcgc ggaagtgaaa    780
accgtaaacg gcatacgcca tatcggcctt gccgccaagc aactggaaga aaaaaaggt    840 aactacgttg ttaccgacca ctaa                                          864
```

<210> SEQ ID NO 88
<211> LENGTH: 405
<212> TYPE: DNA
<213> ORGANISM: Unknown
<220> FEATURE:
<223> OTHER INFORMATION: fusion gene

<400> SEQUENCE: 88

```
gtgaatcgaa ctgccttctg ctgcctttct ctgaccactg ccctgattct gaccgcctgc     60
agcagcggag ggggtggtgt cgccgccgac atcggtgcgg ggcttgccga tgcactaacc    120
gcaccgctcg accataaaga caaaggtttg cagtctttga cgctggatca gtccgtcagg    180
aaaaacgaga aactgaagct ggcggcacaa ggtgcggaaa aaacttatgg aaacggtgac    240
agcctcaata cggcaaatt gaagaacgac aaggtcagcc gtttcgactt tatccgccaa    300
atcgaagtgg acgggcagct cattaccttg gagagtggag agttccaagt atacaaacaa    360
ctggaagaaa aaaaggtaa ctacgttgtt accgaccact aataa                    405
```

<210> SEQ ID NO 89
<211> LENGTH: 966
<212> TYPE: DNA
<213> ORGANISM: Unknown
<220> FEATURE:
<223> OTHER INFORMATION: fusion gene

<400> SEQUENCE: 89

```
gtgaatcgaa ctgccttctg ctgcctttct ctgaccactg ccctgattct gaccgcctgc     60
agcagcggag ggggtggtgt cgccgccgac atcggtgcgg ggcttgccga tgcactaacc    120
gcaccgctcg accataaaga caaaggtttg cagtctttga cgctggatca gtccgtcagg    180
aaaaacgaga aactgaagct ggcggcacaa ggtgcggaaa aaacttatgg aaacggtgac    240
agcctcaata cggcaaatt gaagaacgac aaggtcagcc gtttcgactt tatccgccaa    300
atcgaagtgg acgggcagct cattaccttg gagagtggag agttccaagt atacaaacaa    360
agccattccg ccttaaccgc ctttcagacc gagcaaatac aagattcgga cattccggg    420 aagatggttg cgaaacgcca gttcagaatc ggcgacatag cgggcgaaca tacatctttt    480
gacaagcttc ccgaaggcgg cagggcgaca tatcgcggga cggcgttcgg ttcagacgat    540
gccggcggaa aactgaccta caccatagat ttcgccgcca agcagggaaa cggcaaaatc    600
gaacatttga aatcgccaga actcaatgtc gacctggccg ccgccgatat caagccggat    660
ggaaaacgcc atgccgtcat cagcggttcc gtcctttaca accaagccga aaaggcagt    720 tactccctcg gtatctttgg cggaaaagcc caggaagttg ccggcagcgc ggaagtgaaa    780
accgtaaacg gcatacgcca tatcggcctt gccgccaagc aaggttccct ggaagaaaag    840
aagggtaact atgtggtgac cgaccactct ggtctggagg agaaaaaagg caactacgtt    900
gttactgatc acggctctct ggaggaaaag aaaggtaatt acgtggttac cgaccattcc    960
ggctaa                                                               966
```

<210> SEQ ID NO 90
<211> LENGTH: 504
<212> TYPE: DNA
<213> ORGANISM: Unknown
<220> FEATURE:
<223> OTHER INFORMATION: fusion gene

<400> SEQUENCE: 90

```
gtgaatcgaa ctgccttctg ctgcctttct ctgaccactg ccctgattct gaccgcctgc      60
agcagcggag ggggtggtgt cgccgccgac atcggtgcgg ggcttgccga tgcactaacc     120
gcaccgctcg accataaaga caaaggtttg cagtctttga cgctggatca gtccgtcagg     180
aaaaacgaga aactgaagct ggcggcacaa ggtgcgaaaa aacttatgg aaacggtgac      240
agcctcaata cgggcaaatt gaagaacgac aaggtcagcc gtttcgactt tatccgccaa     300
atcgaagtgg acgggcagct cattaccttg agagtggag agttccaagt atacaaacaa      360
ggttccctgg aagaaaagaa gggtaactat gtggtgaccg accactctgg tctggaggag     420
aaaaaaggca actacgttgt tactgatcac ggctctctgg aggaaaagaa aggtaattac     480
gtggttaccg accattccgg ctaa                                            504
```

<210> SEQ ID NO 91
<211> LENGTH: 1089
<212> TYPE: DNA
<213> ORGANISM: Escherichia coli

<400> SEQUENCE: 91

```
atgatgaagc gcaatattct ggcagtgatc gtccctgctc tgttagtagc aggtactgca      60
aacgctgcag aaatctataa caaagatggc aacaaagtag atctgtacgg taaagctgtt     120
ggtctgcatt atttttccaa gggtaacggt gaaaacagtt acgtggcaa tggcgacatg      180
acctatgccc gtcttggttt taaggggaa actcaaatca attccgatct gaccggttat      240
ggtcagtggg aatataactt ccagggtaac aactctgaag cgctgacgc tcaaactggt      300
aacaaaacgc gtctggcatt cgcgggtctt aaatacgctg acgttggttc tttcgattac     360
ggccgtaact acggtgtggt ttatgatgca ctgggttaca ccgatatgct gccagaattt     420
ggtggtgata ctgcatacag cgatgacttc ttcgttggtc gtgttggcgg cgttgctacc     480
tatcgtaact ccaacttctt tggtctggtt gatggcctga acttcgctgt tcagtacctg     540
ggtaaaaacg agcgtgacac tgcacgccgt tctaacggcg acggtgttgg cggttctatc     600
agctacgaat acgaaggctt tggtatcgtt ggtgcttatg gtgcagctga ccgtaccaac     660
ctgcaagaag ctcaacctct tggcaacggt aaaaagctg aacagtgggc tactggtctg      720
aagtacgacg cgaacaacat ctacctggca gcgaactacg tgaaacccg taacgctacg      780
ccgatcacta taaatttac aaacaccagc ggcttcgcca caaaacgca agacgttctg       840
ttagttgcgc ataccagtt cgatttcggt ctgcgtccgt ccatcgctta caccaaatct      900
aaagcgaaag acgtagaagg tatcggtgat gttgatctgg tgaactactt tgaagtgggc     960
gcaacctact acttcaacaa aaacatgtcc acctatgttg actacatcat caaccagatc    1020
gattctgaca caaactggg cgtaggttca gacgacaccg ttgctgtggg tatcgtttac    1080
cagttctaa                                                            1089
```

<210> SEQ ID NO 92
<211> LENGTH: 1092
<212> TYPE: DNA
<213> ORGANISM: Unknown

<220> FEATURE:
<223> OTHER INFORMATION: fusion gene

<400> SEQUENCE: 92

| | | | | | |
|---|---|---|---|---|---|
| atgatgaagc | gcaatattct | ggcagtgatc | gtccctgctc | tgttagtagc | aggtactgca | 60 |
| aacgctgcag | aaatctataa | caaagatggc | aacaaagtag | atctgtacgg | taaagctgtt | 120 |
| ggtctgcatt | attttctgga | agaaaaaaaa | ggtaactacg | ttgttaccga | ccacggcgac | 180 |
| atgacctatg | cccgtcttgg | ttttaaaggg | gaaactcaaa | tcaattccga | tctgaccggt | 240 |
| tatggtcagt | gggaatataa | cttccagggt | aacaactctg | aaggcgctga | cgctcaaact | 300 |
| ggtaacaaaa | cgcgtctggc | attcgcgggt | cttaaatacg | ctgacgttgg | ttctttcgat | 360 |
| tacggccgta | actacggtgt | ggtttatgat | gcactgggtt | acaccgatat | gctgccagaa | 420 |
| tttggtggtg | atactgcata | cagcgatgac | ttcttcgttg | gtcgtgttgg | cggcgttgct | 480 |
| acctatcgta | actccaactt | ctttggtctg | gttgatggcc | tgaacttcgc | tgttcagtac | 540 |
| ctgggtaaaa | acgagcgtga | cactgcacgc | cgttctaacg | gcgacggtgt | tggcggttct | 600 |
| atcagctacg | aatacgaagg | ctttggtatc | gttggtgctt | atggtgcagc | tgaccgtacc | 660 |
| aacctgcaag | aagctcaacc | tcttggcaac | ggtaaaaaag | ctgaacagtg | gctactggt | 720 |
| ctgaagtacg | acgcgaacaa | catctacctg | gcagcgaact | acggtgaaac | ccgtaacgct | 780 |
| acgccgatca | ctaataaatt | tacaaacacc | agcggcttcg | ccaacaaaac | gcaagacgtt | 840 |
| ctgttagttg | cgcaatacca | gttcgatttc | ggtctgcgtc | cgtccatcgc | ttacaccaaa | 900 |
| tctaaagcga | aagacgtaga | aggtatcggt | gatgttgatc | tggtgaacta | ctttgaagtg | 960 |
| ggcgcaacct | actacttcaa | caaaaacatg | tccacctatg | ttgactacat | catcaaccag | 1020 |
| atcgattctg | acaacaaact | gggcgtaggt | tcagacgaca | ccgttgctgt | gggtatcgtt | 1080 |
| taccagttct | aa | | | | | 1092 |

<210> SEQ ID NO 93
<211> LENGTH: 1194
<212> TYPE: DNA
<213> ORGANISM: Unknown
<220> FEATURE:
<223> OTHER INFORMATION: fusion gene

<400> SEQUENCE: 93

| | | | | | |
|---|---|---|---|---|---|
| atgatgaagc | gcaatattct | ggcagtgatc | gtccctgctc | tgttagtagc | aggtactgca | 60 |
| aacgctgcag | aaatctataa | caaagatggc | aacaaagtag | atctgtacgg | taaagctgtt | 120 |
| ggtctgcatt | attttggttc | cctggaagaa | aagaagggta | actatgtggt | gaccgaccac | 180 |
| tctggtctgg | aggagaaaaa | aggcaactac | gttgttactg | atcacggctc | tctggaggaa | 240 |
| aagaaaggta | attacgtggt | taccgaccat | tccggcggcg | acatgaccta | tgcccgtctt | 300 |
| ggttttaaag | gggaaactca | aatcaattcc | gatctgaccg | ttatggtca | gtgggaatat | 360 |
| aacttccagg | gtaacaactc | tgaaggcgct | gacgctcaaa | ctggtaacaa | aacgcgtctg | 420 |
| gcattcgcgg | gtcttaaata | cgctgacgtt | ggttctttcg | attacggccg | taactacggt | 480 |
| gtggtttatg | atgcactggg | ttacaccgat | atgctgccag | aatttggtgg | tgatactgca | 540 |
| tacagcgatg | acttcttcgt | tggtcgtgtt | ggcggcgttg | ctacctatcg | taactccaac | 600 |
| ttctttggtc | tggttgatgg | cctgaacttc | gctgttcagt | acctgggtaa | aaacgagcgt | 660 |
| gacactgcac | gccgttctaa | cggcgacggt | gttggcggtt | ctatcagcta | cgaatacgaa | 720 |
| ggctttggta | tcgttggtgc | ttatggtgca | gctgaccgta | ccaacctgca | agaagctcaa | 780 |

| | |
|---|---:|
| cctcttggca acggtaaaaa agctgaacag tgggctactg gtctgaagta cgacgcgaac | 840 |
| aacatctacc tggcagcgaa ctacggtgaa acccgtaacg ctacgccgat cactaataaa | 900 |
| tttacaaaca ccagcggctt cgccaacaaa acgcaagacg ttctgttagt tgcgcaatac | 960 |
| cagttcgatt tcggtctgcg tccgtccatc gcttacacca atctaaagc gaaagacgta | 1020 |
| gaaggtatcg gtgatgttga tctggtgaac tactttgaag tgggcgcaac ctactacttc | 1080 |
| aacaaaaaca tgtccaccta tgttgactac atcatcaacc agatcgattc tgacaacaaa | 1140 |
| ctgggcgtag gttcagacga caccgttgct gtgggtatcg tttaccagtt ctaa | 1194 |

<210> SEQ ID NO 94
<211> LENGTH: 1101
<212> TYPE: DNA
<213> ORGANISM: Unknown
<220> FEATURE:
<223> OTHER INFORMATION: fusion gene

<400> SEQUENCE: 94

| | |
|---|---:|
| atgatgaagc gcaatattct ggcagtgatc gtccctgctc tgttagtagc aggtactgca | 60 |
| aacgctgcag aaatctataa caaagatggc aacaaagtag atctgtacgg taaagctgtt | 120 |
| ggtctgcatt atttttccaa gggtaacggt gaaaacagtt acggtggcaa tggcgacatg | 180 |
| acctatgccc gtcttggttt taaaggggaa actcaaatca attccgatct gaccggttat | 240 |
| ggtcagtggg aatataactt ccagggtaac ctggaagaaa aaaaggtaa ctacgttgtt | 300 |
| accgaccacg gtaacaaaac gcgtctggca ttcgcgggtc ttaaatacgc tgacgttggt | 360 |
| tctttcgatt acgccgtaa ctacggtgtg gtttatgatg cactgggtta caccgatatg | 420 |
| ctgccagaat tggtggtga tactgcatac agcgatgact tcttcgttgg tcgtgttggc | 480 |
| ggcgttgcta cctatcgtaa ctccaacttc tttggtctgg ttgatggcct gaacttcgct | 540 |
| gttcagtacc tgggtaaaaa cgagcgtgac actgcacgcc gttctaacgg cgacggtgtt | 600 |
| ggcggttcta tcagctacga atacgaaggc tttggtatcg ttggtgctta tggtgcagct | 660 |
| gaccgtacca acctgcaaga agctcaacct cttggcaacg gtaaaaaagc tgaacagtgg | 720 |
| gctactggtc tgaagtacga cgcgaacaac atctacctgg cagcgaacta cggtgaaacc | 780 |
| cgtaacgcta cgccgatcac taataaattt acaaacacca gcggcttcgc caacaaaacg | 840 |
| caagacgttc tgttagttgc gcaataccag ttcgatttcg gtctgcgtcc gtccatcgct | 900 |
| tacaccaaat ctaaagcgaa agacgtagaa ggtatcggtg atgttgatct ggtgaactac | 960 |
| tttgaagtgg gcgcaacctta ctacttcaac aaaaacatgt ccaccatgt tgactacatc | 1020 |
| atcaaccaga tcgattctga caacaaactg ggcgtaggtt cagacgacac cgttgctgtg | 1080 |
| ggtatcgttt accagttcta a | 1101 |

<210> SEQ ID NO 95
<211> LENGTH: 1104
<212> TYPE: DNA
<213> ORGANISM: Unknown
<220> FEATURE:
<223> OTHER INFORMATION: fusion gene

<400> SEQUENCE: 95

| | |
|---|---:|
| atgatgaagc gcaatattct ggcagtgatc gtccctgctc tgttagtagc aggtactgca | 60 |
| aacgctgcag aaatctataa caaagatggc aacaaagtag atctgtacgg taaagctgtt | 120 |
| ggtctgcatt atttttccaa gggtaacggt gaaaacagtt acggtggcaa tggcgacatg | 180 |
| acctatgccc gtcttggttt taaaggggaa actcaaatca attccgatct gaccggttat | 240 |

```
ggtcagtggg aatataactt ccagggtaac aactctgaag gcgctgacgc tcaaactggt        300
aacaaaacgc gtctggcatt cgcgggtctt aaatacgctg acgttggttc tttcgattac        360
ggccgtaact acggtgtggt ttatgatgca ctgggttaca ccgatatgct gccagaattt        420
ggtggtgata ctgcatacag cgatgacttc ttcgttggtc gtgttggcgg cgttgctacc        480
tatcgtaact ccaacttctt tggtctggtt gatggcctga acttcgctgt tcagtacctg        540
ggtaaaaacc tggaagaaaa aaaaggtaac tacgttgtta ccgaccacaa cggcgacggt        600
gttggcggtt ctatcagcta cgaatacgaa ggctttggta tcgttggtgc ttatggtgca        660
gctgaccgta ccaacctgca agaagctcaa cctcttggca acggtaaaaa agctgaacag        720
tgggctactg gtctgaagta cgacgcgaac aacatctacc tggcagcgaa ctacggtgaa        780
acccgtaacg ctacgccgat cactaataaa tttacaaaca ccagcggctt cgccaacaaa        840
acgcaagacg ttctgttagt tgcgcaatac cagttcgatt tcggtctgcg tccgtccatc        900
gcttacacca aatctaaagc gaaagacgta gaaggtatcg tgatgttga tctggtgaac        960 tactttgaag tgggcgcaac ctactacttc aacaaaaaca tgtccaccta tgttgactac       1020
atcatcaacc agatcgattc tgacaacaaa ctgggcgtag gttcagacga caccgttgct       1080
gtgggtatcg tttaccagtt ctaa                                              1104

<210> SEQ ID NO 96
<211> LENGTH: 1206
<212> TYPE: DNA
<213> ORGANISM: Unknown
<220> FEATURE:
<223> OTHER INFORMATION: fusion gene

<400> SEQUENCE: 96
atgatgaagc gcaatattct ggcagtgatc gtccctgctc tgttagtagc aggtactgca         60
aacgctgcag aaatctataa caaagatggc aacaaagtag atctgtacgg taaagctgtt        120
ggtctgcatt attttttcca gggtaacggt gaaaacagtt acgtggcaa tggcgacatg        180 acctatgccc gtcttggttt taaggggaa actcaaatca attccgatct gaccggttat        240
ggtcagtggg aatataactt ccagggtaac aactctgaag gcgctgacgc tcaaactggt        300
aacaaaacgc gtctggcatt cgcgggtctt aaatacgctg acgttggttc tttcgattac        360
ggccgtaact acggtgtggt ttatgatgca ctgggttaca ccgatatgct gccagaattt        420
ggtggtgata ctgcatacag cgatgacttc ttcgttggtc gtgttggcgg cgttgctacc        480
tatcgtaact ccaacttctt tggtctggtt gatggcctga acttcgctgt tcagtacctg        540
ggtaaaaacg gttccctgga agaaagaag gtaactatg tggtgaccga ccactctggt        600
ctggaggaga aaaaggcaa ctacgttgtt actgatcacg gctctctgga ggaaaagaaa        660
ggtaattacg tggttaccga ccattccggc aacggcgacg tgttggcgg ttctatcagc        720 tacgaatacg aaggctttgg tatcgttggt gcttatggtg cagctgaccg taccaacctg        780
caagaagctc aacctcttgg caacggtaaa aaagctgaac agtgggctac tggtctgaag        840
tacgacgcga acaacatcta cctggcagcg aactacggtg aaacccgtaa cgctacgccg        900
atcactaata aatttacaaa caccagcggc ttcgccaaca aaacgcaaga cgttctgtta        960
gttgcgcaat accagttcga tttcggtctg cgtccgtcca tcgcttacac caaatctaaa       1020
gcgaaagacg tagaaggtat cggtgatgtt gatctggtga actactttga agtgggcgca       1080
acctactact tcaacaaaaa catgtccacc tatgttgact acatcatcaa ccagatcgat       1140
```

```
tctgacaaca aactgggcgt aggttcagac gacaccgttg ctgtgggtat cgtttaccag      1200
ttctaa                                                                 1206

<210> SEQ ID NO 97
<211> LENGTH: 1092
<212> TYPE: DNA
<213> ORGANISM: Unknown
<220> FEATURE:
<223> OTHER INFORMATION: fusion gene

<400> SEQUENCE: 97
atgatgaagc gcaatattct ggcagtgatc gtccctgctc tgttagtagc aggtactgca        60
aacgctgcag aaatctataa caaagatggc aacaaagtag atctgtacgg taaagctgtt       120
ggtctgcatt attttccaa gggtaacggt gaaaacagtt acggtggcaa tggcgacatg        180
acctatgccc gtcttggttt taaaggggaa actcaaatca attccgatct gaccggttat       240
ggtcagtggg aatataactt ccagggtaac aactctgaag gcgctgacgc tcaaactggt       300
aacaaaacgc gtctggcatt cgcgggtctt aaatacgctg acgttggttc tttcgattac       360
ggccgtaact acggtgtggt ttatgatgca ctgggttaca ccgatatgct gccagaattt       420
ggtggtgata ctgcatacag cgatgacttc ttcgttggtc gtgttggcgg cgttgctacc       480
tatcgtaact ccaacttctt tggtctggtt gatggcctga acttcgctgt tcagtacctg       540
ggtaaaaacg agcgtgacac tgcacgccgt tctaacggcg acggtgttgg cggttctatc       600
agctacgaat acgaaggctt tggtatcgtt ggtgcttatg gtgcagctga ccgtaccaac       660
ctgcaagaag ctcaacctct tggcaacggt aaaaagctg aacagtgggc tactggtctg       720
aagtacgacg cgaacaacat ctacctggca gcgaactacg gtgaaacccg taacgctacg       780
ctggaagaaa aaaaggtaa ctacgttgtt accgaccacg ccaacaaaac gcaagacgtt       840
ctgttagttg cgcaatacca gttcgatttc ggtctgcgtc cgtccatcgc ttacaccaaa       900
tctaaagcga agacgtaga aggtatcggt gatgttgatc tggtgaacta ctttgaagtg       960
ggcgcaacct actacttcaa caaaaacatg tccacctatg ttgactacat catcaaccag      1020
atcgattctg acaacaaact gggcgtaggt tcagacgaca ccgttgctgt gggtatcgtt      1080
taccagttct aa                                                          1092

<210> SEQ ID NO 98
<211> LENGTH: 1098
<212> TYPE: DNA
<213> ORGANISM: Unknown
<220> FEATURE:
<223> OTHER INFORMATION: fusion gene

<400> SEQUENCE: 98
atgatgaagc gcaatattct ggcagtgatc gtccctgctc tgttagtagc aggtactgca        60
aacgctgcag aaatctataa caaagatggc aacaaagtag atctgtacgg taaagctgtt       120
ggtctgcatt attttccaa gggtaacggt gaaaacagtt acggtggcaa tggcgacatg        180
acctatgccc gtcttggttt taaaggggaa actcaaatca attccgatct gaccggttat       240
ggtcagtggg aatataactt ccagggtaac aactctgaag gcgctgacgc tcaaactggt       300
aacaaaacgc gtctggcatt cgcgggtctt aaatacgctg acgttggttc tttcgattac       360
ggccgtaact acggtgtggt ttatgatgca ctgggttaca ccgatatgct gccagaattt       420
ggtggtgata ctgcatacag cgatgacttc ttcgttggtc gtgttggcgg cgttgctacc       480
tatcgtaact ccaacttctt tggtctggtt gatggcctga acttcgctgt tcagtacctg       540
```

```
ggtaaaaacg agcgtgacac tgcacgccgt tctaacggcg acggtgttgg cggttctatc        600
agctacgaat acgaaggctt tggtatcgtt ggtgcttatg gtgcagctga ccgtaccaac        660
ctgcaagaag ctcaacctct tggcaacggt aaaaagctg aacagtgggc tactggtctg         720
aagtacgacg cgaacaacat ctacctggca gcgaactacg gtgaaacccg taacgctacg        780
ccgatcacta ataaatttac aaacaccagc ggcttcgcca acaaaacgca agacgttctg        840
ttagttgcgc aataccagtt cgatttcggt ctgcgtccgt ccatcgctta caccaaatct        900
aaagcgaaac tggaagaaaa aaaaggtaac tacgttgtta ccgaccacgt gaactacttt        960
gaagtgggcg caacctacta cttcaacaaa aacatgtcca cctatgttga ctacatcatc       1020
aaccagatcg attctgacaa caaactgggc gtaggttcag acgacaccgt tgctgtgggt       1080
atcgtttacc agttctaa                                                    1098

<210> SEQ ID NO 99
<211> LENGTH: 1089
<212> TYPE: DNA
<213> ORGANISM: Unknown
<220> FEATURE:
<223> OTHER INFORMATION: fusion gene

<400> SEQUENCE: 99
atgatgaagc gcaatattct ggcagtgatc gtccctgctc tgttagtagc aggtactgca         60
aacgctgcag aaatctataa caaagatggc aacaaagtag atctgtacgg taaagctgtt        120
ggtctgcatt attttccaa gggtaacggt gaaaacagtt acggtggcaa tggcgacatg         180
acctatgccc gtcttggttt taaggggaa actcaaatca attccgatct gaccggttat         240
ggtcagtggg aatataactt ccagggtaac aactctgaag cgctgacgc tcaaactggt         300 aacaaaacgc gtctggcatt cgcgggtctt aaatacgctg acgttggttc tttcgattac        360
ggccgtaact acggtgtggt ttatgatgca ctgggttaca ccgatatgct gccagaattt        420
ggtggtgata ctgcatacag cgatgacttc ttcgttggtc gtgttggcgg cgttgctacc        480
tatcgtaact ccaacttctt tggtctggtt gatggcctga acttcgctgt tcagtacctg        540
ggtaaaaacg agcgtgacac tgcacgccgt tctaacggcg acggtgttgg cggttctatc        600
agctacgaat acgaaggctt tggtatcgtt ggtgcttatg gtgcagctga ccgtaccaac        660
ctgcaagaag ctcaacctct tggcaacggt aaaaagctg aacagtgggc tactggtctg         720
aagtacgacg cgaacaacat ctacctggca gcgaactacg gtgaaacccg taacgctacg        780
ccgatcacta ataaatttac aaacaccagc ggcttcgcca acaaaacgca agacgttctg        840
ttagttgcgc aataccagtt cgatttcggt ctgcgtccgt ccatcgctta caccaaatct        900
aaagcgaaac gtagaagg tatcggtgat gttgatctgg tgaactactt tgaagtgggc          960
gcaacctact acttcaacaa aaacatgtcc acctatgttg actacatcat caaccagctg       1020
gaagaaaaaa aaggtaacta cgttgttacc gaccacaccg ttgctgtggg tatcgtttac       1080
cagttctaa                                                              1089

<210> SEQ ID NO 100
<211> LENGTH: 1191
<212> TYPE: DNA
<213> ORGANISM: Escherichia coli

<400> SEQUENCE: 100
atgaaaataa aaacaggtgc acgcatcctc gcattatccg cattaacgac gatgatgttt        60
```

| | |
|---|---|
| tccgcctcgg ctctcgccaa atcgaagaa ggtaaactgg taatctggat taacggcgat | 120 |
| aaaggctata acggtctcgc tgaagtcggt aagaaattcg agaaagatac cggaattaaa | 180 |
| gtcaccgttg agcatccgga taaactggaa gagaaattcc cacaggttgc ggcaactggc | 240 |
| gatggccctg acattatctt ctgggcacac gaccgctttg gtggctacgc tcaatctggc | 300 |
| ctgttggctg aaatcacccc ggacaaagcg ttccaggaca agctgtatcc gtttacctgg | 360 |
| gatgccgtac gttacaacgg caagctgatt gcttacccga tcgctgttga agcgttatcg | 420 |
| ctgatttata caaagatct gctgccgaac ccgccaaaaa cctgggaaga gatcccggcg | 480 |
| ctggataaag aactgaaagc gaaagtaag agcgcgctga tgttcaacct gcaagaaccg | 540 |
| tacttcacct ggccgctgat tgctgctgac gggggttatg cgttcaagta tgaaaacggc | 600 |
| aagtacgaca ttaaagacgt gggcgtggat aacgctggcg cgaaagcggg tctgaccttc | 660 |
| ctggttgacc tgattaaaaa caaacacatg aatgcagaca ccgattactc catcgcagaa | 720 |
| gctgccttta taaaggcga aacagcgatg accatcaacg gcccgtgggc atggtccaac | 780 |
| atcgacacca gcaaagtgaa ttatggtgta acggtactgc cgaccttcaa gggtcaacca | 840 |
| tccaaaccgt tcgttggcgt gctgagcgca ggtattaacg ccgccagtcc gaacaaagag | 900 |
| ctggcgaaag agttcctcga aaactatctg ctgactgatg aaggtctgga agcggttaat | 960 |
| aaagacaaac cgctgggtgc cgtagcgctg aagtcttacg aggaagagtt ggcgaaagat | 1020 |
| ccacgtattg ccgccaccat ggaaaacgcc cagaaaggtg aaatcatgcc gaacatcccg | 1080 |
| cagatgtccg ctttctggta tgccgtgcgt actgcggtga tcaacgccgc cagcggtcgt | 1140 |
| cagactgtcg atgaagccct gaaagacgcg cagactcgta tcaccaagta a | 1191 |

<210> SEQ ID NO 101
<211> LENGTH: 1230
<212> TYPE: DNA
<213> ORGANISM: Unknown
<220> FEATURE:
<223> OTHER INFORMATION: fusion gene

<400> SEQUENCE: 101

| | |
|---|---|
| atgaaaataa aaacaggtgc acgcatcctc gcattatccg cattaacgac gatgatgttt | 60 |
| tccgcctcgg ctctcgccaa atcgaagaa ggtaaactgg taatctggat taacggcgat | 120 |
| aaaggctata acggtctcgc tgaagtcggt aagaaattcg agaaagatac cggaattaaa | 180 |
| gtcaccgttg agcatccgga taaactggaa gagaaattcc cacaggttgc ggcaactggc | 240 |
| gatggccctg acattatctt ctgggcacac gaccgctttg gtggctacgc tcaatctggc | 300 |
| ctgttggctg aaatcacccc ggacaaagcg ttccaggaca agctgtatcc gtttacctgg | 360 |
| gatgccgtac gttacaacgg caagctgatt gcttacccga tcgctgttga agcgttatcg | 420 |
| ctgatttata caaagatct gctgccgaac ccgccaaaaa cctgggaaga gatcccggcg | 480 |
| ctggataaag aactgaaagc gaaagtaag agcgcgctga tgttcaacct gcaagaaccg | 540 |
| tacttcacct ggccgctgat tgctgctgac gggggttatg cgttcaagta tgaaaacggc | 600 |
| aagtacgaca ttaaagacgt gggcgtggat aacgctggcg cgaaagcggg tctgaccttc | 660 |
| ctggttgacc tgattaaaaa caaacacatg aatgcagaca ccgattactc catcgcagaa | 720 |
| gctgccttta taaaggcga aacagcgatg accatcaacg gcccgtgggc atggtccaac | 780 |
| atcgacacca gcaaagtgaa ttatggtgta acggtactgc cgaccttcaa gggtcaacca | 840 |
| tccaaaccgt tcgttggcgt gctgagcgca ggtattaacg ccgccagtcc gaacaaagag | 900 |
| ctggcgaaag agttcctcga aaactatctg ctgactgatg aaggtctgga agcggttaat | 960 |

```
aaagacaaac cgctgggtgc cgtagcgctg aagtcttacg aggaagagtt ggcgaaagat    1020
ccacgtattg ccgccaccat ggaaaacgcc cagaaaggtg aaatcatgcc gaacatcccg    1080
cagatgtccg ctttctggta tgccgtgcgt actgcggtga tcaacgccgc cagcggtcgt    1140
cagactgtcg atgaagccct gaaagacgcg cagactcgta tcaccaagct ggaagaaaaa    1200
aaaggtaact acgttgttac cgaccactaa                                    1230
```

<210> SEQ ID NO 102
<211> LENGTH: 225
<212> TYPE: DNA
<213> ORGANISM: Unknown
<220> FEATURE:
<223> OTHER INFORMATION: fusion gene

<400> SEQUENCE: 102

```
attcaagtgg aagcgactga caaagatctg ggcccgaatg ccatgtaac ttattcaatc     60 gttacggata cagatatcca ggtagaggca accgataaag atttaggtcc caatggccac   120
gtcacatata gtatcgtaac ggataccgac attcaggtgg aagctaccga taaagacctg   180
ggtccgaatg gtcacgtgac gtattctatt gttaccgata cagat                   225
```

<210> SEQ ID NO 103
<211> LENGTH: 585
<212> TYPE: DNA
<213> ORGANISM: Unknown
<220> FEATURE:
<223> OTHER INFORMATION: fusion gene

<400> SEQUENCE: 103

```
gtgaatcgaa ctgccttctg ctgcctttct ctgaccactg ccctgattct gaccgcctgc    60
agcagcggag ggggtggtgt cgccgccgac atcggtgcgg ggcttgccga tgcactaacc   120
gcaccgctcg accataaaga caaaggtttg cagtctttga cgctggatca gtccgtcagg   180
aaaaacgaga aactgaagct ggcggcacaa ggtgcgaaaa aaacttatgg aaacggtgac   240
agcctcaata cgggcaaatt gaagaacgac aaggtcagcc gtttcgactt tatccgccaa   300
atcgaagtgg acgggcagct cattaccttg gagagtggag agttccaagt atacaaacaa   360
attcaagtgg aagcgactga caaagatctg ggcccgaatg ccatgtaac ttattcaatc    420 gttacggata cagatatcca ggtagaggca accgataaag atttaggtcc caatggccac   480
gtcacatata gtatcgtaac ggataccgac attcaggtgg aagctaccga taaagacctg   540
ggtccgaatg gtcacgtgac gtattctatt gttaccgata cagat                   585
```

<210> SEQ ID NO 104
<211> LENGTH: 1047
<212> TYPE: DNA
<213> ORGANISM: Unknown
<220> FEATURE:
<223> OTHER INFORMATION: fusion gene

<400> SEQUENCE: 104

```
gtgaatcgaa ctgccttctg ctgcctttct ctgaccactg ccctgattct gaccgcctgc    60
agcagcggag ggggtggtgt cgccgccgac atcggtgcgg ggcttgccga tgcactaacc   120
gcaccgctcg accataaaga caaaggtttg cagtctttga cgctggatca gtccgtcagg   180
aaaaacgaga aactgaagct ggcggcacaa ggtgcgaaaa aaacttatgg aaacggtgac   240
agcctcaata cgggcaaatt gaagaacgac aaggtcagcc gtttcgactt tatccgccaa   300
```

| | |
|---|---|
| atcgaagtgg acgggcagct cattaccttg gagagtggag agttccaagt atacaaacaa | 360 |
| agccattccg ccttaaccgc ctttcagacc gagcaaatac aagattcgga gcattccggg | 420 |
| aagatggttg cgaaacgcca gttcagaatc ggcgacatag cgggcgaaca tacatctttt | 480 |
| gacaagcttc ccgaaggcgg cagggcgaca tatcgcggga cggcgttcgg ttcagacgat | 540 |
| gccggcggaa aactgaccta caccatagat ttcgccgcca agcagggaaa cggcaaaatc | 600 |
| gaacatttga aatcgccaga actcaatgtc gacctggccg ccgccgatat caagccggat | 660 |
| ggaaaacgcc atgccgtcat cagcggttcc gtcctttaca accaagccga aaaggcagt | 720 |
| tactccctcg gtatctttgg cggaaaagcc caggaagttg ccggcagcgc ggaagtgaaa | 780 |
| accgtaaacg gcatacgcca tatcggcctt gccgccaagc aaattcaagt ggaagcgact | 840 |
| gacaaagatc tgggcccgaa tggccatgta acttattcaa tcgttacgga tacagatatc | 900 |
| caggtagagg caaccgataa agatttaggt cccaatggcc acgtcacata tagtatcgta | 960 |
| acggataccg acattcaggt ggaagctacc gataaagacc tgggtccgaa tggtcacgtg | 1020 |
| acgtattcta ttgttaccga tacagat | 1047 |

<210> SEQ ID NO 105
<211> LENGTH: 1413
<212> TYPE: DNA
<213> ORGANISM: Unknown
<220> FEATURE:
<223> OTHER INFORMATION: fusion gene

<400> SEQUENCE: 105

| | |
|---|---|
| atgaaaataa aaacaggtgc acgcatcctc gcattatccg cattaacgac gatgatgttt | 60 |
| tccgcctcgg ctctcgccaa aatcgaagaa ggtaaactgg taatctggat taacggcgat | 120 |
| aaaggctata acgtctcgc tgaagtcggt aagaaattcg agaaagatac cggaattaaa | 180 |
| gtcaccgttg agcatccgga taaactggaa gagaaattcc cacaggttgc ggcaactggc | 240 |
| gatgccctg acattatctt ctgggcacac gaccgctttg gtggctacgc tcaatctggc | 300 |
| ctgttggctg aaatcacccc ggacaaagcg ttccaggaca agctgtatcc gtttacctgg | 360 |
| gatgccgtac gttacaacgg caagctgatt gcttacccga tcgctgttga agcgttatcg | 420 |
| ctgatttata acaaagatct gctgccgaac ccgccaaaaa cctgggaaga tcccggcg | 480 |
| ctggataaag aactgaaagc gaaaggtaag agcgcgctga tgttcaacct gcaagaaccg | 540 |
| tacttcacct ggccgctgat tgctgctgac gggggttatg cgttcaagta tgaaaacggc | 600 |
| aagtacgaca ttaaagacgt gggcgtggat aacgctggcg cgaaagcggg tctgaccttc | 660 |
| ctggttgacc tgattaaaaa caaacacatg aatgcagaca ccgattactc catcgcagaa | 720 |
| gctgccttta taaaggcga aacagcgatg accatcaacg gccgtgggc atggtccaac | 780 |
| atcgacacca gcaaagtgaa ttatggtgta acggtactgc cgaccttcaa gggtcaacca | 840 |
| tccaaaccgt tcgttggcgt gctgagcgca ggtattaacg ccgccagtcc gaacaaagag | 900 |
| ctggcgaaag agttcctcga aaactatctg ctgactgatg aaggtctgga agcggttaat | 960 |
| aaagacaaac gctgggtgc cgtagcgctg aagtcttacg aggaagagtt ggcgaaagat | 1020 |
| ccacgtattg ccgccaccat ggaaaacgcc cagaaaggtg aaatcatgcc gaacatcccg | 1080 |
| cagatgtccg ctttctggta tgccgtgcgt actgcggtga tcaacgccgc cagcggtcgt | 1140 |
| cagactgtcg atgaagccct gaaagacgcg cagactcgta tcaccaagat tcaagtggaa | 1200 |
| gcgactgaca agatctgggg cccgaatggc catgtaactt attcaatcgt tacggataca | 1260 |
| gatatccagg tagaggcaac cgataaagat ttaggtccca atggccacgt cacatatagt | 1320 |

| | |
|---|---|
| atcgtaacgg ataccgacat tcaggtggaa gctaccgata aagacctggg tccgaatggt | 1380 |
| cacgtgacgt attctattgt taccgataca gat | 1413 |

<210> SEQ ID NO 106
<211> LENGTH: 300
<212> TYPE: DNA
<213> ORGANISM: Unknown
<220> FEATURE:
<223> OTHER INFORMATION: fusion gene

<400> SEQUENCE: 106

| | |
|---|---|
| ggggtgacga gcgcgccaga tacacgtccg gctcctggct cgacggcccc ccctgcccac | 60 |
| ggagtaacgt cagcaccaga cacgcgcccg gcaccgggat ccaccgctcc gccggcgcat | 120 |
| ggtgttacta gtgcgcccga tacccgtcca gcaccgggct ccaccgcgcc tccagcccat | 180 |
| ggagtcacgt cagcaccgga cactcgtcca gccccgggtt caaccgcgcc tccggcacat | 240 |
| ggcgtcacct cagctccaga tacgcgcccg gccccaggca gtaccgctcc gccggcgcat | 300 |

<210> SEQ ID NO 107
<211> LENGTH: 660
<212> TYPE: DNA
<213> ORGANISM: Unknown
<220> FEATURE:
<223> OTHER INFORMATION: fusion gene

<400> SEQUENCE: 107

| | |
|---|---|
| gtgaatcgaa ctgccttctg ctgcctttct ctgaccactg ccctgattct gaccgcctgc | 60 |
| agcagcggag ggggtggtgt cgccgccgac atcggtgcgg ggcttgccga tgcactaacc | 120 |
| gcaccgctcg accataaaga caaaggtttg cagtctttga cgctggatca gtccgtcagg | 180 |
| aaaaacgaga aactgaagct ggcggcacaa ggtgcgaaaa aaacttatgg aaacggtgac | 240 |
| agcctcaata cgggcaaatt gaagaacgac aaggtcagcc gtttcgactt tatccgccaa | 300 |
| atcgaagtgg acgggcagct cattaccttg gagagtggag agttccaagt atacaaacaa | 360 |
| ggggtgacga gcgcgccaga tacacgtccg gctcctggct cgacggcccc ccctgcccac | 420 |
| ggagtaacgt cagcaccaga cacgcgcccg gcaccgggat ccaccgctcc gccggcgcat | 480 |
| ggtgttacta gtgcgcccga tacccgtcca gcaccgggct ccaccgcgcc tccagcccat | 540 |
| ggagtcacgt cagcaccgga cactcgtcca gccccgggtt caaccgcgcc tccggcacat | 600 |
| ggcgtcacct cagctccaga tacgcgcccg gccccaggca gtaccgctcc gccggcgcat | 660 |

<210> SEQ ID NO 108
<211> LENGTH: 1488
<212> TYPE: DNA
<213> ORGANISM: Unknown
<220> FEATURE:
<223> OTHER INFORMATION: fusion gene

<400> SEQUENCE: 108

| | |
|---|---|
| atgaaaataa aaacaggtgc acgcatcctc gcattatccg cattaacgac gatgatgttt | 60 |
| tccgcctcgg ctctcgccaa aatcgaagaa ggtaaactgg taatctggat taacggcgat | 120 |
| aaaggctata acggtctcgc tgaagtcggt aagaaattcg agaaagatac cggaattaaa | 180 |
| gtcaccgttg agcatccgga taaactggaa gagaaattcc cacaggttgc ggcaactggc | 240 |
| gatggccctg acattatctt ctgggcacac gaccgctttg gtggctacgc tcaatctggc | 300 |
| ctgttggctg aaatcacccc ggacaaagcg ttccaggaca agctgtatcc gtttacctgg | 360 |

```
gatgccgtac gttacaacgg caagctgatt gcttacccga tcgctgttga agcgttatcg    420
ctgatttata caaagatct gctgccgaac ccgccaaaaa cctgggaaga gatcccggcg    480
ctggataaag aactgaaagc gaaaggtaag agcgcgctga tgttcaacct gcaagaaccg    540
tacttcacct ggccgctgat tgctgctgac gggggttatg cgttcaagta tgaaaacggc    600
aagtacgaca ttaaagacgt gggcgtggat aacgctggcg cgaaagcggg tctgaccttc    660
ctggttgacc tgattaaaaa caaacacatg aatgcagaca ccgattactc catcgcagaa    720
gctgccttta ataaaggcga acagcgatg accatcaacg gcccgtgggc atggtccaac    780
atcgacacca gcaaagtgaa ttatggtgta acggtactgc cgaccttcaa gggtcaacca    840
tccaaaccgt tcgttggcgt gctgagcgca ggtattaacg ccgccagtcc gaacaaagag    900
ctggcgaaag agttcctcga aactatctg ctgactgatg aaggtctgga agcggttaat    960
aaagacaaac cgctgggtgc cgtagcgctg aagtcttacg aggaagagtt ggcgaaagat   1020
ccacgtattg ccgccaccat ggaaaacgcc cagaaaggtg aaatcatgcc gaacatcccg   1080
cagatgtccg ctttctggta tgccgtgcgt actgcggtga tcaacgccgc cagcggtcgt   1140
cagactgtcg atgaagccct gaaagacgcg cagactcgta tcaccaaggg ggtgacgagc   1200
gcgccagata cacgtccggc tcctggctcg acggccccccc tgcccacgg agtaacgtca   1260 gcaccagaca cgcgcccggc accgggatcc accgctccgc cggcgcatgg tgttactagt   1320
gcgcccgata cccgtccagc accgggctcc accgcgcctc cagcccatgg agtcacgtca   1380
gcaccggaca ctcgtccagc cccgggttca accgcgcctc cggcacatgg cgtcacctca   1440
gctccagata cgcgcccggc cccaggcagt accgctccgc cggcgcat              1488

<210> SEQ ID NO 109
<211> LENGTH: 488
<212> TYPE: PRT
<213> ORGANISM: Neisseria meningitidis

<400> SEQUENCE: 109

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175
```

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Glu Val Ala Gly
    450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485

<210> SEQ ID NO 110
<211> LENGTH: 275
<212> TYPE: PRT
<213> ORGANISM: Unknown
<220> FEATURE:
<223> OTHER INFORMATION: Aggregatibacter actinomycetemcomitans

<400> SEQUENCE: 110

Met Val Tyr Pro Val Ile Thr Lys Gly Arg Lys Gln Met Lys Thr Lys
1               5                   10                  15

Tyr Leu Leu Ala Ala Leu Thr Val Ala Cys Thr Leu Ser Ala Cys Ser
            20                  25                  30

Gln Ala Ala Gly Gly Leu Ala Asp Gly Leu Leu Lys Pro Phe Asp Pro
        35                  40                  45

```
Lys Ala Lys Asp Trp Lys Gln Leu Thr Ile Ser Glu Ser Val Pro Asp
 50                  55                  60

Asn Gly Thr Leu Glu Leu Thr Asp Arg Gly Gly Lys Thr Gln Ile Leu
 65                  70                  75                  80

Arg Lys Gly Gly Val Leu Asp Thr Gly His Leu Arg Ser Asp Lys Ile
                 85                  90                  95

Ser Asp Tyr Asp Tyr Val Lys Lys Ile Asn Val Asn Gly Gln Ile Ile
            100                 105                 110

Glu Leu Glu Arg Gly Asp Phe Leu Ile Tyr Lys Gln Asn Asn Ser Ile
        115                 120                 125

Ile Ala Ala Thr Leu Ala Lys Gln Lys Thr Asn Ala Asp Gly Thr Arg
130                 135                 140

Ser Ser Ala Phe Asp Phe His Val Asn Glu Ile Gln Gly Arg Asp Ile
145                 150                 155                 160

Ala Phe Asn Asn Leu Pro Ala Ser Gly Gln Val Asn Tyr Arg Gly Ile
                165                 170                 175

Ala Phe Thr Gly Asp Asp Arg Arg Gly Arg Leu Ser Tyr Thr Ile Asp
            180                 185                 190

Phe Ala Lys Lys Gln Gly Ser Gly Arg Ile Ser Asp Leu Arg Gly Asp
        195                 200                 205

Tyr Asn Val Asp Leu Ala Gln Thr Asp Val Arg Ala Met Gly Asn Gly
210                 215                 220

Ser Gly Leu Ser Gly Lys Ala Met Lys Asn Gly Val Glu Arg Gly Asn
225                 230                 235                 240

Tyr Thr Leu Lys Ile Phe Gly Asn Lys Ala Glu Glu Ile Ala Gly Lys
                245                 250                 255

Ala Glu Ile Lys Thr Gly Lys Gly Thr Gln Glu Ile Gly Leu Ala Gly
            260                 265                 270

Lys Lys Glu
        275

<210> SEQ ID NO 111
<211> LENGTH: 535
<212> TYPE: PRT
<213> ORGANISM: Unknown
<220> FEATURE:
<223> OTHER INFORMATION: fusion protein

<400> SEQUENCE: 111

Met Phe Lys Arg Ser Val Ile Ala Met Ala Cys Ile Phe Ala Leu Ser
  1               5                  10                  15

Ala Cys Gly Gly Gly Gly Gly Ser Pro Asp Val Lys Ser Ala Asp
                 20                  25                  30

Thr Leu Ser Lys Pro Ala Ala Pro Val Val Ser Glu Lys Glu Thr Glu
             35                  40                  45

Ala Lys Glu Asp Ala Pro Gln Ala Gly Ser Gln Gly Gln Gly Ala Pro
         50                  55                  60

Ser Ala Gln Gly Ser Gln Asp Met Ala Ala Val Ser Glu Glu Asn Thr
 65                  70                  75                  80

Gly Asn Gly Gly Ala Val Thr Ala Asp Asn Pro Lys Asn Glu Asp Glu
                 85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125
```

```
Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
                195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
    275                 280                 285

Pro Lys Pro Thr Ser Phe Ala Arg Phe Arg Arg Ser Ala Arg Ser Arg
290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
    355                 360                 365

Ala Lys Gly Glu Met Leu Ala Gly Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
    435                 440                 445

Asp Val Ser Gly Lys Phe Tyr Gly Pro Ala Gly Glu Glu Val Ala Gly
450                 455                 460

Lys Tyr Ser Tyr Arg Pro Thr Asp Ala Glu Lys Gly Phe Gly Val
465                 470                 475                 480

Phe Ala Gly Lys Lys Glu Gln Asp Gly Ser Leu Glu Glu Lys Lys Gly
                485                 490                 495

Asn Tyr Val Val Thr Asp His Ser Gly Leu Glu Glu Lys Lys Gly Asn
            500                 505                 510

Tyr Val Val Thr Asp His Gly Ser Leu Glu Glu Lys Lys Gly Asn Tyr
    515                 520                 525

Val Val Thr Asp His Ser Gly
    530                 535
```

```
<210> SEQ ID NO 112
<211> LENGTH: 513
<212> TYPE: PRT
<213> ORGANISM: Unknown
<220> FEATURE:
<223> OTHER INFORMATION: fusion protein

<400> SEQUENCE: 112

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
    195                 200                 205

Asn Gly Val Leu Ile Asp Gly Pro Ser Gln Asn Ile Thr Leu Thr His
210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Ala Val Tyr Asn Gly Glu Val
```

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
            405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
            435                 440                 445

Asp Val Ser Gly Lys Phe Tyr Gly Pro Ala Gly Glu Val Ala Gly
        450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp Leu Glu Glu Lys Lys Gly Asn Tyr
                485                 490                 495

Val Val Thr Gly Pro Leu Thr Ser Pro Ser Pro Ser Arg Leu Gln Arg
            500                 505                 510

Arg

<210> SEQ ID NO 113
<211> LENGTH: 1479
<212> TYPE: DNA
<213> ORGANISM: Neisseria meningitidis

<400> SEQUENCE: 113

```
atgtttaaac gcagcgtaat cgcaatggct tgtattttg cccttttcagc ctgcggggc      60
ggcggtggcg gatcgcccga tgtcaagtcg gcggacacgc tgtcaaaacc tgccgcccct    120
gttgtttctg aaaagagac agaggcaaag gaagatgcgc cacaggcagg ttctcaagga     180
cagggcgcgc catccgcaca aggcagtcaa gatatggcgg cggtttcgga gaaaatca     240
ggcaatggcg gtgcggtaac agcggataat cccaaaaatg aagacgaggt ggcacaaaat    300
gatatgccgc aaaatgccgc cggtacagat agttcgacac cgaatcacac cccggatccg    360
aatatgcttg ccggaaatat ggaaaatcaa gcaacggatg ccggggaatc gtctcagccg    420
gcaaaccaac cggatatggc aaatgcggcg gacggaatgc aggggacga tccgtcggca    480
ggcgggcaaa atgccggcaa tacgctgcc caaggtgcaa atcaagccgg aaacaatcaa    540
gccgccggtt cttcagatcc catccccgcg tcaaaccctg cacctgcgaa tggcggtagc    600
aatttttggaa gggttgattt ggctaatggc gttttgattg acgggccgtc gcaaaatata    660
acgttgaccc actgtaaagg cgattcttgt agtggcaata atttcttgga tgaagaagta    720
cagctaaaaat cagaatttga aaaattaagt gatgcagaca aaataagtaa ttacaagaaa    780
gatgggaaga atgataaatt tgtcggtttg gttgccgata gtgtgcagat gaagggaatc    840
aatcaatata ttatcttta aaacctaaa cccacttcat ttgcgcgatt taggcgttct    900
gcacggtcga ggcggtcgct tccggccgag atgccgctga ttcccgtcaa tcaggcggat    960
acgctgattg tcgatgggga agcggtcagc ctgacggggc attccggcaa tatcttcgcg   1020
cccgaaggga attaccggta tctgacttac ggggcgaaa aattgcccgg cggatcgtat    1080
gcccttcgtg ttcaaggcga accggcaaaa ggcgaaatgc ttgcgggcgc ggccgtgtac   1140
aacggcgaag tactgcattt ccatacggaa aacggccgtc cgtacccgac caggggcagg   1200
tttgccgcaa aagtcgattt cggcagcaaa tctgtggacg gcattatcga cagcggcgat   1260
gatttgcata tgggtacgca aaaattcaaa gccgccatcg atggaaacgg ctttaagggg   1320
```

```
acttggacgg aaaatggcag cggggatgtt tccggaaagt tttacggccc ggccggcgag    1380
gaagtggcgg gaaaatacag ctatcgcccg acagatgcgg aaagggcgg attcggcgtg    1440 tttgccggca aaaagagca ggattgataa catcaccat                            1479
```

<210> SEQ ID NO 114
<211> LENGTH: 1542
<212> TYPE: DNA
<213> ORGANISM: Unknown
<220> FEATURE:
<223> OTHER INFORMATION: fusion sequence

<400> SEQUENCE: 114

```
atgtttaaac gcagcgtaat cgcaatggct tgtattttg cccttcagc ctgcggggc       60 ggcggtggcg atcgcccga tgtcaagtcg gcggacacgc tgtcaaaacc tgccgcccct    120
gttgtttctg aaaagagac agaggcaaag gaagatgcgc cacaggcagg ttctcaagga    180
cagggcgcgc catccgcaca aggcagtcaa gatatggcgg cggtttcgga agaaaataca    240
ggcaatggcg gtgcggtaac agcggataat cccaaaaatg aagacgaggt ggcacaaaat    300
gatatgccgc aaaatgccgc cggtacagat agttcgacac cgaatcacac cccgatccg    360 aatatgcttg ccggaaatat ggaaaatcaa gcaacggatg ccggggaatc gtctcagccg    420
gcaaaccaac cggatatggc aaatgcggcg gacggaatgc aggggacga tccgtcggca    480 ggcgggcaaa atgccggcaa tacggctgcc caaggtgcaa atcaagccgg aaacaatcaa    540
gccgccggtt cttcagatcc catccccgcg tcaaaccctg cacctgcgaa tggcggtagc    600
aattttggaa gggttgattt ggctaatggc gttttgattg acgggccgtc gcaaaatata    660
acgttgaccc actgtaaagg cgattcttgt agtggcaata atttcttgga tgaagaagta    720
cagctaaaat cagaattga aaattaagt gatgcagaca aaataagtaa ttacaagaaa    780
gatgggaaga tgataaatt tgtcggtttg gttgccgata gtgtgcagat gaagggaatc    840
aatcaatata ttatctttta taaacctaaa cccacttcat ttgcgcgatt taggcgttct    900
gcacggtcga ggcggtcgct tccgccgag atgccgctga ttcccgtcaa tcaggcggat    960
acgctgattg tcgatgggga agcggtcagc ctgacgggc attccggcaa tatcttcgcg   1020
cccgaaggga attaccggta tctgacttac ggggcggaaa aattgcccgg cggatcgtat   1080
gcccttcgtg ttcaaggcga accggcaaaa ggcgaaatgc ttgcgggcgc ggccgtgtac   1140
aacggcgaag tactgcattt ccatacggaa acggccgtc cgtacccgac caggggcagg   1200
tttgccgcaa aagtcgattt cggcagcaaa tctgtggacg gcattatcga cagcggcgat   1260
gatttgcata tgggtacgca aaaattcaaa gccgccatcg atggaaacgg ctttaagggg   1320
acttggacgg aaaatggcag cggggatgtt tccggaaagt tttacggccc ggccggcgag   1380
gaagtggcgg gaaaatacag ctatcgcccg acagatgcgg aaagggcgg attcggcgtg   1440 tttgccggca aaaagagca ggatctggaa gaaaaaaag gtaactacgt tgttaccgga   1500
ccactaacat caccatcacc atcacgatta caaagacgat ga                     1542
```

<210> SEQ ID NO 115
<211> LENGTH: 1608
<212> TYPE: DNA
<213> ORGANISM: Unknown
<220> FEATURE:
<223> OTHER INFORMATION: fusion sequence

<400> SEQUENCE: 115

```
atgtttaaac gcagcgtaat cgcaatggct tgtatttttg cccttttcagc ctgcgggggc     60
ggcggtggcg gatcgcccga tgtcaagtcg gcggacacgc tgtcaaaacc tgccgcccct    120
gttgtttctg aaaagagac agaggcaaag gaagatgcgc acaggcagg ttctcaagga     180
cagggcgcgc catccgcaca aggcagtcaa gatatggcgg cggtttcgga agaaaataca    240
ggcaatggcg gtgcggtaac agcggataat cccaaaaatg aagacgaggt ggcacaaaat    300
gatatgccgc aaaatgccgc cggtacagat agttcgacac cgaatcacac cccgatccg     360
aatatgcttg ccggaaatat ggaaaatcaa gcaacggatg ccggggaatc gtctcagccg    420
gcaaaccaac cggatatggc aaatgcggcg gacggaatgc aggggacga tccgtcggca    480
ggcgggcaaa atgccggcaa tacggctgcc caaggtgcaa atcaagccgg aaacaatcaa    540
gccgccggtt cttcagatcc catccccgcg tcaaaccctg cacctgcgaa tggcggtagc    600
aattttggaa gggttgattt ggctaatggc gttttgattg acgggccgtc gcaaaatata    660
acgttgaccc actgtaaagg cgattcttgt agtggcaata atttcttgga tgaagaagta    720
cagctaaaat cagaatttga aaattaagt gatgcagaca aataagtaa ttacaagaaa     780
gatgggaaga atgataaatt tgtcggtttg gttgccgata tgtgtcagat gaagggaatc    840
aatcaatata ttatcttta taaacctaaa cccacttcat ttgcgcgatt taggcgttct    900
gcacggtcga ggcggtcgct tccggccgag atgccgctga ttcccgtcaa tcaggcggat    960
acgctgattg tcgatgggga agcggtcagc ctgacgggc attccggcaa tatcttcgcg   1020
cccgaaggga attaccggta tctgacttac ggggcggaaa aattgcccgg cggatcgtat   1080
gcccttcgtg ttcaaggcga accggcaaaa ggcgaaatgc ttgcgggcgc ggccgtgtac   1140
aacggcgaag tactgcattt ccatacggaa aacggccgtc cgtacccgac caggggcagg   1200
tttgccgcaa aagtcgattt cggcagcaaa tctgtggacg gcattatcga cagcggcgat   1260
gatttgcata tgggtacgca aaaattcaaa gccgccatcg atggaaacgg ctttaagggg   1320
acttggacga aaaatggcag cggggatgtt tccggaaagt tttacggccc ggccggcgag   1380
gaagtggcgg gaaaatacag ctatcgcccg acagatgcgg aaaagggcgg attcggcgtg   1440
tttgccggca aaaagagca ggatggttcc ctggaagaaa agaagggtaa ctatgtggtg   1500
accgaccact ctggtctgga ggagaaaaaa ggcaactacg ttgttactga tcacggctct   1560
ctggaggaaa agaaaggtaa ttacgtggtt accgaccatt ccggctaa              1608
```

<210> SEQ ID NO 116
<211> LENGTH: 828
<212> TYPE: DNA
<213> ORGANISM: Unknown
<220> FEATURE:
<223> OTHER INFORMATION: fusion sequence

<400> SEQUENCE: 116

```
atggtttacc ctgttataac gaaaggaagg aaacaaatga aaacaaaata tttattggcg     60
gcgctgaccg tcgcctgcac attatccgca tgcagccaag ctgccggggg gttggcggat    120
ggtctactga aaccgttcga tccgaaagca aaagactgga agcagttaac catctccgaa    180
tctgttcccg ataacggcac tttggaacta accgaccgcg gcggcaaaac ccagatcttg    240
cgtaaaggcg gcgttctgga tacaggccat ttgagatccg ataagatctc tgactacgat    300
tacgtcaaaa aaatcaacgt gaacggtcaa ataatcgagt tggaacgagg cgattttctg    360
atatataaac agaataattc catcatcgcc gctacgttag cgaaacagaa aaccaacgca    420
gatggtacac gctcctctgc ctttgatttc catgtcaacg agattcaagg gcgagacatc    480
```

```
gcctttaata atctgccggc ttcgggacag gtaaactatc gcggcatcgc atttaccggc    540
gatgaccgta gaggtcgttt atcctacact atcgacttcg ctaaaaaaca aggcagcggt    600
cgcatcagtg atctacgtgg tgactataac gtagatttgg cgcaaacaga cgtccgcgca    660
atggggaacg gttccgggtt gagtggtaag gctatgaaaa atggtgtgga aagaggaaat    720
tacacgctaa aaatcttcgg taacaaggca gaagaaatcg ccggtaaagc tgagatcaaa    780
accggtaagg gaactcaaga aatcggtttg gcaggtaaaa aagaataa                 828
```

<210> SEQ ID NO 117
<211> LENGTH: 59
<212> TYPE: DNA
<213> ORGANISM: Unknown
<220> FEATURE:
<223> OTHER INFORMATION: oligonucleotide primer

<400> SEQUENCE: 117

```
aaaggtaact acgttgttac cgaccactaa catcaccatc accatcacga ttacaaaga     59
```

<210> SEQ ID NO 118
<211> LENGTH: 43
<212> TYPE: DNA
<213> ORGANISM: Unknown
<220> FEATURE:
<223> OTHER INFORMATION: oligonucleotide primer

<400> SEQUENCE: 118

```
ccggcaaaaa agagcaggat ggttccctgg aagaaaagaa ggg                      43
```

<210> SEQ ID NO 119
<211> LENGTH: 36
<212> TYPE: DNA
<213> ORGANISM: Unknown
<220> FEATURE:
<223> OTHER INFORMATION: oligonucleotide primer

<400> SEQUENCE: 119

```
gtgatggtga tgttagccgg aatggtcggt aaccac                              36
```

<210> SEQ ID NO 120
<211> LENGTH: 20
<212> TYPE: DNA
<213> ORGANISM: Unknown
<220> FEATURE:
<223> OTHER INFORMATION: oligonucleotide primer

<400> SEQUENCE: 120

```
atcctgctct tttttgccgg                                                20
```

<210> SEQ ID NO 121
<211> LENGTH: 32
<212> TYPE: DNA
<213> ORGANISM: Unknown
<220> FEATURE:
<223> OTHER INFORMATION: oligonucleotide primer

<400> SEQUENCE: 121

```
taacatcacc atcaccatca cgattacaaa ga                                  32
```

<210> SEQ ID NO 122
<211> LENGTH: 36
<212> TYPE: DNA
<213> ORGANISM: Unknown
<220> FEATURE:

<223> OTHER INFORMATION: oligonucleotide primer

<400> SEQUENCE: 122
gaaggagata tacatatggt ttaccctgtt ataacg      36

<210> SEQ ID NO 123
<211> LENGTH: 36
<212> TYPE: DNA
<213> ORGANISM: Unknown
<220> FEATURE:
<223> OTHER INFORMATION: oligonucleotide primer

<400> SEQUENCE: 123
atggtgatgg tgatgttctt ttttacctgc caaacc      36

<210> SEQ ID NO 124
<211> LENGTH: 41
<212> TYPE: DNA
<213> ORGANISM: Unknown
<220> FEATURE:
<223> OTHER INFORMATION: oligonucleotide primer

<400> SEQUENCE: 124
catatgtata tctccttctt aaagttaaac aaaattattt c      41

<210> SEQ ID NO 125
<211> LENGTH: 48
<212> TYPE: DNA
<213> ORGANISM: Unknown
<220> FEATURE:
<223> OTHER INFORMATION: oligonucleotide primer

<400> SEQUENCE: 125
catcaccatc accatcacta agattacaaa gacgatgatg acaagtga      48

<210> SEQ ID NO 126
<211> LENGTH: 14
<212> TYPE: PRT
<213> ORGANISM: Homo sapiens

<400> SEQUENCE: 126

Leu Glu Glu Lys Lys Gly Asn Tyr Val Val Thr Asp His Cys
1               5                   10

<210> SEQ ID NO 127
<211> LENGTH: 20
<212> TYPE: PRT
<213> ORGANISM: Homo sapiens

<400> SEQUENCE: 127

Pro Asp Thr Arg Pro Ala Pro Gly Ser Thr Ala Pro Pro Ala His Gly
1               5                   10                  15

Val Thr Ser Ala
            20

<210> SEQ ID NO 128
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 128
ggagatatac atatgtttaa acgcagcgta atc      33

<210> SEQ ID NO 129
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 129
gtgatggtga tgttatcaat cctgctcttt tttg                         34

<210> SEQ ID NO 130
<211> LENGTH: 47
<212> TYPE: DNA
<213> ORGANISM: Artificial Sequence
<220> FEATURE:
<223> OTHER INFORMATION: oligonucleotide primer

<400> SEQUENCE: 130
aacgtagtta cctttttttt cttccagatc ctgctctttt ttgccgg            47

<210> SEQ ID NO 131
<211> LENGTH: 36
<212> TYPE: DNA
<213> ORGANISM: Artificial Sequence
<220> FEATURE:
<223> OTHER INFORMATION: synthetic primer

<400> SEQUENCE: 131
ggggtgacga gcgcgccaga tacacgtccg gctcct                        36

<210> SEQ ID NO 132
<211> LENGTH: 36
<212> TYPE: DNA
<213> ORGANISM: Artificial Sequence
<220> FEATURE:
<223> OTHER INFORMATION: synthetic primer

<400> SEQUENCE: 132
atgcgccggc ggggccgtcg agccaggagc cggacg                        36

<210> SEQ ID NO 133
<211> LENGTH: 42
<212> TYPE: DNA
<213> ORGANISM: Artificial Sequence
<220> FEATURE:
<223> OTHER INFORMATION: synthetic primer

<400> SEQUENCE: 133
ccgccggcgc atggagtaac gtcagcacca gacacgcgcc cg                 42

<210> SEQ ID NO 134
<211> LENGTH: 42
<212> TYPE: DNA
<213> ORGANISM: Artificial Sequence
<220> FEATURE:
<223> OTHER INFORMATION: synthetic primer

<400> SEQUENCE: 134
gtgggcaggg ggagcggtgg atcccggtgc cgggcgcgtg tc                 42

<210> SEQ ID NO 135
<211> LENGTH: 42
<212> TYPE: DNA
<213> ORGANISM: Artificial Sequence
<220> FEATURE:
<223> OTHER INFORMATION: synthetic primer

<400> SEQUENCE: 135 cccctgccc acggtgttac tagtgcgccc gatacccgtc ca        42

<210> SEQ ID NO 136
<211> LENGTH: 42
<212> TYPE: DNA
<213> ORGANISM: Artificial Sequence
<220> FEATURE:
<223> OTHER INFORMATION: synthetic primer

<400> SEQUENCE: 136
atgcgccggc ggcgcggtgg agcccggtgc tggacgggta tc        42

<210> SEQ ID NO 137
<211> LENGTH: 42
<212> TYPE: DNA
<213> ORGANISM: Artificial Sequence
<220> FEATURE:
<223> OTHER INFORMATION: synthetic primer

<400> SEQUENCE: 137
ccgccggcgc atggagtcac gtcagcaccg gacactcgtc ca        42

<210> SEQ ID NO 138
<211> LENGTH: 42
<212> TYPE: DNA
<213> ORGANISM: Artificial Sequence
<220> FEATURE:
<223> OTHER INFORMATION: synthetic primer

<400> SEQUENCE: 138
gtgtgctgga ggcgcggttg aacccggggc tggacgagtg tc        42

<210> SEQ ID NO 139
<211> LENGTH: 42
<212> TYPE: DNA
<213> ORGANISM: Artificial Sequence
<220> FEATURE:
<223> OTHER INFORMATION: synthetic primer

<400> SEQUENCE: 139
cctccagcac acggcgtcac ctcagctcca gatacgcgcc cg        42

<210> SEQ ID NO 140
<211> LENGTH: 42
<212> TYPE: DNA
<213> ORGANISM: Artificial Sequence
<220> FEATURE:
<223> OTHER INFORMATION: synthetic primer

<400> SEQUENCE: 140
atgtgccggc ggagcggtac tgcctggggc cgggcgcgta tc        42

<210> SEQ ID NO 141
<211> LENGTH: 36
<212> TYPE: DNA
<213> ORGANISM: Artificial Sequence
<220> FEATURE:
<223> OTHER INFORMATION: synthetic primer

<400> SEQUENCE: 141
gtgatggtga tggtgatgtt aatgcgccgg cggagc        36

<210> SEQ ID NO 142

```
<211> LENGTH: 30
<212> TYPE: DNA
<213> ORGANISM: Artificial Sequence
<220> FEATURE:
<223> OTHER INFORMATION: synthetic primer

<400> SEQUENCE: 142
caagtataca aacaagggt gacgagcgcg                                       30

<210> SEQ ID NO 143
<211> LENGTH: 37
<212> TYPE: DNA
<213> ORGANISM: Artificial Sequence
<220> FEATURE:
<223> OTHER INFORMATION: synthetic primer

<400> SEQUENCE: 143
cgcgcagact cgtatcacca aggggtgac gagcgcg                               37

<210> SEQ ID NO 144
<211> LENGTH: 38
<212> TYPE: DNA
<213> ORGANISM: Artificial Sequence
<220> FEATURE:
<223> OTHER INFORMATION: synthetic primer

<400> SEQUENCE: 144
tcgtgatggt gatggtgatg ttaatgcgcc ggcggagc                             38

<210> SEQ ID NO 145
<211> LENGTH: 39
<212> TYPE: DNA
<213> ORGANISM: Homo sapiens

<400> SEQUENCE: 145
ctggaagaaa aaaagctaa ctacgttgtt accgaccac                             39

<210> SEQ ID NO 146
<211> LENGTH: 13
<212> TYPE: PRT
<213> ORGANISM: Homo sapiens

<400> SEQUENCE: 146

Leu Glu Glu Lys Lys Gly Asn Tyr Val Val Thr Asp His
 1               5                  10

<210> SEQ ID NO 147
<211> LENGTH: 90
<212> TYPE: DNA
<213> ORGANISM: Artificial Sequence
<220> FEATURE:
<223> OTHER INFORMATION: recombinant sequence

<400> SEQUENCE: 147
ctggaagaaa aaaaggtaa ctacgttgtt accgaccact ctggtctgga agaaaaaaaa      60
ggtaactacg ttgttaccga ccacggctct                                      90

<210> SEQ ID NO 148
<211> LENGTH: 30
<212> TYPE: PRT
<213> ORGANISM: Artificial Sequence
<220> FEATURE:
<223> OTHER INFORMATION: recombinant sequence

<400> SEQUENCE: 148
```

Leu Glu Glu Lys Lys Gly Asn Tyr Val Val Thr Asp His Ser Gly Leu
1               5                   10                  15

Glu Glu Lys Lys Gly Asn Tyr Val Val Thr Asp His Gly Ser
            20                  25                  30

<210> SEQ ID NO 149
<211> LENGTH: 274
<212> TYPE: PRT
<213> ORGANISM: Neisseria meningitidis

<400> SEQUENCE: 149

Val Asn Arg Thr Ala Phe Cys Cys Ile Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Asp Leu
        195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 150
<211> LENGTH: 275
<212> TYPE: PRT
<213> ORGANISM: Unknown
<220> FEATURE:
<223> OTHER INFORMATION: Aggregatibacter actinomycetemcomitans

<400> SEQUENCE: 150

Met Val Tyr Pro Val Ile Thr Lys Gly Arg Lys Gln Met Lys Thr Lys
1               5                   10                  15

-continued

```
Tyr Leu Leu Ala Ala Leu Thr Val Ala Cys Thr Leu Ser Ala Cys Ser
            20                  25                  30

Gln Ala Ala Gly Gly Leu Ala Asp Gly Leu Leu Lys Pro Phe Asp Pro
            35                  40                  45

Lys Ala Lys Asp Trp Lys Gln Leu Thr Ile Ser Glu Ser Val Pro Asp
            50                  55                  60

Asn Gly Thr Leu Glu Leu Thr Asp Arg Gly Gly Lys Thr Gln Ile Leu
65                      70                  75                  80

Arg Lys Gly Gly Val Leu Asp Thr Gly His Leu Arg Ser Asp Lys Ile
                85                  90                  95

Ser Asp Tyr Asp Tyr Val Lys Lys Ile Asn Val Asn Gly Gln Ile Ile
                100                 105                 110

Glu Leu Glu Arg Gly Asp Phe Leu Ile Tyr Lys Gln Asn Asn Ser Ile
            115                 120                 125

Ile Ala Ala Thr Leu Ala Lys Gln Lys Thr Asn Ala Asp Gly Thr Arg
130                 135                     140

Ser Ser Ala Phe Asp Phe His Val Asn Glu Ile Gln Gly Arg Asp Ile
145                 150                 155                 160

Ala Phe Asn Asn Leu Pro Ala Ser Ser Gln Val Asn Tyr Arg Gly Ile
                165                 170                 175

Ala Phe Thr Gly Asp Asp Arg Arg Gly Arg Leu Ser Tyr Thr Ile Asp
                180                 185                 190

Phe Ala Lys Lys Gln Gly Ser Gly Arg Ile Ser Asp Leu Arg Gly Asp
            195                 200                 205

Tyr Asn Val Asp Leu Ala Gln Thr Asp Val Arg Ala Met Gly Asn Gly
            210                 215                 220

Ser Gly Leu Ser Gly Lys Ala Met Lys Asn Gly Val Glu Arg Gly Asn
225                 230                 235                 240

Tyr Thr Leu Lys Ile Phe Gly Asn Lys Ala Glu Glu Ile Ala Gly Lys
                245                 250                 255

Ala Glu Ile Lys Thr Gly Lys Gly Thr Gln Glu Ile Gly Leu Ala Gly
            260                 265                 270

Lys Lys Glu
        275
```

IMMUNOGENIC COMPOSITIONS CONTAINING BACTERIAL OUTER MEMBRANE VESICLES AND THERAPEUTIC USES THEREOF

This application is a U.S. national stage of PCT/EP2016/061031 filed on 17 May 2016, which claims priority to and the benefit of European Application No. 15168024.6 filed on 18 May 2015, the contents of which are incorporated herein by reference in their entireties.

The present invention provides means and products for the stimulation of an immune response against tumors in a subject in need thereof. More specifically the invention provides immunogenic compositions containing bacterial outer membrane vesicles loaded with tumor antigens, fusion proteins comprising a bacterial protein and a tumor antigen, and isolated bacterial outer membrane vesicles (OMVs) containing said fusion proteins. The fusion proteins, OMVs and immunogenic compositions according to the invention are used in the prevention and treatment of tumors.

BACKGROUND ART

Bacterial Outer Membrane Vesicles (OMVs)

More than 40 years ago, researchers made the observation that Gram-negative bacteria secrete Outer Membrane Vesicles (OMVs) (Beveridge T J (1999) *J Bacteriol.* 181: 4725-33; Mayrand D & Grenier D. (1989) *Can J Microbiol.* 35:607-13). However, the last 15 to 20 years have brought a greater understanding of the regulation and function of vesiculation. OMVs are closed spheroid particles of a heterogeneous size, 20-300 nm in diameter, generated through a "budding out" of the bacterial outer membrane. Consistent with that, the majority of OMV components are represented by LPS, glycerophospholipids, outer membrane proteins and periplasmic proteins (A. Kulp and Kuehn M. J. (2010) *Annu. Rev. Microbiol.* 64, 163-184; T. N. Ellis and Kuehen M. J. (2010) *Microbiol. Mol. Biol. Rev.* 74, 81-94).

OMVs represent a distinct secretory pathway with a multitude of functions, including inter and intra species cell-to-cell cross-talk, biofilm formation, genetic transformation, defense against host immune responses and toxin and virulence factor delivery to host cells (A. Kulp and Kuehn M. J. (2010) *Annu. Rev. Microbiol.* 64, 163-184). OMVs interaction to host cells can occur by endocytosis after binding to host cell receptors or lipid rafts. Alternatively, OMVs have been reported to fuse to host cell membrane, leading to the direct release of their content into the cytoplasm of the host cells (A. Kulp and Kuehn M. J. (2010) *Annu. Rev. Microbiol.* 64, 163-184; T. N. Ellis and Kuehen M. J. (2010) *Micrbiol. Mol. Biol. Rev.* 74, 81-94).

OMVs purified from several pathogens, including *Neisseria, Salmonella, Pseudomonas, Vibrio cholerae Burkholderia*, and *E. coli*, induce potent protective immune responses against the pathogens they derive from (B. S. Collins (2011) *Discovery Medicine*, 12, 7-15), and highly efficacious anti-*Neisseria* OMV-based vaccines are already available for human use (J. Holst et al. (2009) *Vaccine*, 27S, B3-B12). Such remarkable protection is attributed to three key features of OMVs.

First, they are readily phagocytosed by professional antigen-presenting cells which get activated and present OMV-derived peptides in the context of MHC molecules.

Second, they carry the proper immunogenic antigens which, in extracellular pathogens, usually reside on the surface and therefore are naturally incorporated in OMVs. Indeed, OMV immunization induces potent antibody responses against the major membrane-associated antigens. However, OMV immunogenicity is not restricted to antibody responses. For instance, mice immunized with *Salmonella* OMVs develop robust *Salmonella*-specific B and T cell responses, and OMVs stimulate IFN-γ production by a large proportion of CD4+ T cells from mice previously infected with *Salmonella*, indicating that OMVs are an abundant source of antigens recognized by *Salmonella*-specific CD4+ T cells (R. C. Alaniz et al., (2007) *J. Immunol.* 179, 7692-7701).

Third, and most importantly, OMVs carry most of the bacterial Pathogen-Associated-Molecular Patterns (PAMPs) which, by binding to pathogen recognition receptors (PRRs), play a key role in stimulating innate immunity and promoting adaptive immune responses. OMV-associated PAMPs include LPS which, in concert with MD-2 and CD14, binds TLR-4, lipoproteins whose acylpeptide derivatives interact with TLR-1/2 and 2/6 heterodimers, and peptidoglycan whose degradation products bind to intracellular NOD1/2 (A. Moshiri et al., *Hum. Vaccines. Immunother.* (2012) 8, 953-955; T. N. Ellis et al., (2010) *Inn. Immun.* 78, 3822-3831; M. Kaparakis et al., (2010) *Cell. Miocrobiol.* 12, 372-385). The engagement of this group of PPRs results in the activation of transcription factors (NF-kB) and the consequent expression of specific cytokines. Interestingly, LPS, lipoproteins and peptidoglycan can work synergistically, thus potentiating the built-in adjuvanticity of OMVs (D. J. Chen et al., (2010) *PNAS*, 107, 3099-3104).

An additional interesting property of OMVs is their capacity to induce protection at the mucosal level. Protection at the mucosal sites is known to be at least partially mediated by the presence of pathogen-specific IgAs and Th17 cells. In particular, a growing body of evidence suggests that Th17 cells have evolved to mediate protective immunity against a variety of pathogens at different mucosal sites. Interestingly, Th17 cells have recently also been shown to play a crucial role in the generation of vaccine-induced protective responses. For instance, it has been reported that in mice whole cell pertussis vaccines (Pw) induce Th17 cells and neutralization of IL-17 after vaccination reduces protection against a pulmonary challenge with *B. pertussis*. Similarly, in a CD4+ T cell dependent, antibody-independent model of vaccine-induced protection following *S. pneumoniae* challenge, treatment with IL-17-antibodies resulted in reduced immunity to pneumococcal colonization compared to the control serum treated mice (Malley R, et al. (2006) *Infect Immun.*, 74:2187-95).

Elicitation of IgAs and Th17 cells by OMVs has been well documented and this can explain mechanistically the good protective activities of OMVs against several mucosal pathogens. For instance, immunization with *Vibrio cholerae*-derived OMVs protects rabbits against *Vibrio cholerae* oral challenge (Roy N. et al. (2010) *Immunol. Clinical Microbiol.* 60, 18-27) and *Pasteurella multocida*-derived and *Mannheimia haemolytica*-derived OMVs protect mice from oral challenge with *P. multocida* (Roier S. et al., (2013) *Int. J. Med. Microbiol.* 303, 247-256). In addition, intranasal immunization with *Porphyromonas gingivalis* OMVs elicits potent IgA production at both serum and mucosal level and immunization with *Escherichia coli*-derived OMVs prevent bacteria-induced lethality. Protective effect of *Escherichia coli*-derived OMVs is primarily mediated by OMV-specific, IFN-γ and IL-17 producing, T cells (Kim O Y et al., (2013) *J. Immunol.* 190, 4092-4102).

Finally, a key feature of OMVs is the possibility to manipulate their protein content by genetic engineering. This feature was demonstrated for the first time by Kesty and Kuehn who showed that *Yersinia enterocolitica* outer membrane protein Ail assembled on OMVs surface when expressed in *E. coli*, and that the GFP fluorescence protein fused to the "twin arginine transport (Tat)" signal sequence was incorporated in the OMV lumen (N. C. Kesty and Kuhen M. J. (2004) *J. Biol. Chem.* 279, 2069-2076). Following the observation by Kesty and Kuehn, an increasing number of heterologous proteins have been successfully delivered to OMVs using a variety of strategies. For instance, heterologous antigens have been delivered to the surface of OMVs by fusing them to the β-barrel forming autotransporter ADA and to hemolysin ClyA, two proteins that naturally compartmentalized into *E. coli* OMVs (J. Schroeder and Aebischer T. (2009) *Vaccine*, 27, 6748-6754; D. J. Chen et al., (2010) *PNAS*, 107, 3099-3104). Recently, heterologous antigens from Group A *Streptococcus* and Group B *Streptococcus* were delivered to the lumen of *E. coli* vesicles by fusing their coding sequences to the leader peptide of *E. coli* OmpA. Interestingly, when the recombinant vesicles were used to immunize mice, they elicited high titers of functional antibodies against the heterologous antigens, despite their luminal location (Fantappiè et al., (2014) *Journal of Extracellular Vesicles*, 3, 24015).

Despite the many strategies successfully used to deliver heterologous antigens to the vesicle compartment, it has to be pointed out that a universal system working for any protein antigen has not been described yet. A strategy that is effective for one specific antigen in terms of level of expression and elicitation of immune responses can be inefficient with other antigens.

Therefore, the identification of novel strategies to deliver antigens to the OMV compartment is highly needed.

In general, the amount of OMV released by Gram-negative bacteria when grown under laboratory conditions is too low to allow the exploitation of OMVs in biotechnological applications. However, it has been shown that under stress conditions, such as high temperature, OMV release is substantially increased. Furthermore, a number of mutations have been described, many of them affecting the composition of the periplasmic and membrane compartments, that result in abundant vesicle production. For instance, in *Neisseria meningitidis*, a mutation in the gna33 gene, encoding a glucosyltransferase, has been shown to drive the release of several milligrams of vesicles per liter in the culture supernatant (Ferrari et al., (2006) *Proteomics*, 6, 1856-1866). Similar quantities of vesicles are obtained from *Escherichia coli* strains carrying deletions in the genes encoding the Tol/Pal system (a protein complex involved in the connection of the inner membrane with the outer membrane) (Bernadac A. et al., (1998)*J. Bacteriol.* 180, 4872-4878) and in the ompA gene, encoding one of the major outer membrane proteins of *E. coli* (Fantappiè et al., (2014) *Journal of Extracellular Vesicles*, 3, 24015). Such quantities make the production process of OMVs highly efficient and inexpensive thus making natural and engineered vesicles extremely attractive for vaccine purposes. A number of other mutations have been described that enhance the production of OMVs in several Gram negative bacteria, including *Salmonella* and *E. coli* (Deatherage B. L. et al. (2009) *Mol. Microbiol.* 72, 1395-1407; McBroom A. J. and Kuehen M. J. (2007) *Mol. Microbiol.* 63, 545-558), and such mutations are amenable to be exploited to develop scalable OMV production processes.

As far as the production of OMVs for industrial applications is concerned, a number of methods have been described. The first ones to be developed make use of mild detergents that promote the production of great yield of vesicles from biomass and decrease the level of toxicity by removing a substantial amount of LPS (Fredriksen J. H. et al, (1991) NIPH Ann. 14, 67-79). Although these processes have been proved to produce safe and effective vaccines designed to fight Meningococcal B epidemics (Granoff D. (2010), *Clin. Infect. Dis.* 50, S54-S65) their main drawback is that the detergent treatment favor bacterial cell lysis with the consequence that the OMV preparations are heavily contaminated with cytoplasmic proteins (Ferrari et al., (2006) *Proteomics*, 6, 1856-1866). This affect the immune response and can reduce the breath of protection. More recently, detergent-free methods for OMV production have been proposed. Such methods involve the separation of the bacterial culture supernatant from biomass and the purification of vesicles from the supernatant using tangential flow filtration (TFF) (Berlanda Scorza F. et al., (2012) *PlosOne* 7, e35616).

The yield of OMV production using centrifugation couple to TFF can exceed 100 mg/liter of culture and therefore the process is perfectly compatible with large scale production.

One of the potential issues encountered in using OMVs in vaccine applications is the presence of lipopolysaccharide (LPS), an endotoxin known to be reactogenic both in animals and humans. Possible strategies to reduce reactogenicity is to extract LPS from OMVs using mild detergents (Fredriksen J. H. et al, (1991) NIPH Ann. 14, 67-79) or to formulate OMVs with alum hydroxide which absorbs LPS and keeps it confined at the site of injection (Ferrari et al., (2006) *Proteomics*, 6, 1856-1866; Snape M. D. et al., (2010) *Pediatr. Infect. Dis. J.* 29, e71-e79). Another strategy is to genetically alter the LPS synthetic pathway of the strain used for OMV production so that the purified vesicles carry modified versions of LPS with reduced reactogenicity. For instance, in *Neisseria meningitidis* one promising mutant with attenuated endotoxin activity contains a deletion in the lpxL1 gene (also referred to as the msbB gene) (Fisseha M. et al., (2005) *Infect. Immun.*, 73:4070-4080). This mutation results in a LPS carrying a penta-acylated lipid A, which is poorly recognized by human Toll-like receptor 4 (Steeghs L. et al. (2008) *Infect. Immun.*, 76:3801-3807), instead of the more toxic hexa-acylated lipid A, which is present in the LPS produced by wild-type strains. The inactivation of msbB gene to produce less toxigenic OMVs has also been reported for *Shigella*, *Salmonella* and *E. coli* (Berlanda Scorza F. et al., (2012) *PlosOne* 7, e35616; Lee S-R et al., (2009) *J. Microb. Biotechnol.* 19, 1271-1279; Dong H. L. et al., (2011) *Vaccine*, 29, 8293-8301). In *E. coli* an additional mutation in the pagP gene has been described that, when combined with msbB mutation, results in the production of LPS with a fully penta-acylated lipid A which has a low reactogenicity property (Dong H. L. et al., (2011) *Vaccine*, 29, 8293-8301). Finally, by using Synthetic Biology, Needham and co-workers (Needham B. D. et al., (2013) *PNAS*, 110, 1464-1469) have created a collection of novel LPS synthetic pathways which lead to the synthesis of LPS carrying different modifications, each displaying distinct TLR4 agonist activities, cytokine induction and reactogenicity properties. OMVs purified from *E. coli* carrying such engineered LPS pathways have high potential for the design of vaccines with ad hoc modulated immunogenicity and adjuvanticity properties.

*Neisseria meningitidis* Factor H Binding Protein

Factor H binding protein (fHbp) is a 28 kDa surface-exposed lipoprotein of *Neisseria meningitidis* (F. Cantini et al., (2006), *J. Biol Chem.*, 281, 7220-7). fHbp is able to bind factor H (fH), the central regulator of the alternative complement pathway, and in this way it down-regulates complement activation (Lo H. et al., (2009) *Lancet Infect. Dis.* 9: 418-427) and impairs complement-mediated bacterial lysis by human plasma. fHbp is present on the surface of most meningococcal strains (Fletcher L. D. et al., (2004) *Infect. Immun.*, 72: 2088-2100) and high levels of fHbp expression have been found in hyper-virulent meningococcal strains (Masignani et al., (2003) *JEM* 6: 789-799). Sequence analysis has classified fHbp in 3 main variant groups (var1, var2 and var3) (Masignani V et al (2003) *JEM* 6: 789-799). To study the immunogenic and functional properties of the protein, fHbp variant 1 was initially divided for convenience into three regions, named "domain" A, B, and C (Giuliani M M et al (2005) *Infect Immun.* 2: 1151-1160). Domain A encompasses amino acids 27 to 119 of the lipoprotein unprocessed precursor, domain B starts from amino acid 120 and ends at residue 183, and finally domain C spans from amino acid 184 to the end (amino acid 274) (F. Cantini et al., (2006), *J Biol Chem.*, 281, 7220-7). More recent structural studies revealed that fHbp folds to form two β-barrels, with the amino-terminal barrel consisting of the A and part of the B regions and the carboxy-terminal barrel composed of the rest of the B and the C regions (Schneider M C et al., (2009) *Nature*, 458: 890-893; Faleri A et al, (2014) *FASEB J.* 4: 1644-53).

In the *E. coli* model Gram-negative bacterium, in which the lipoprotein sorting process has been well characterized, all outer membrane lipoproteins face the periplasmic space. They reach their final destination in two major steps (M. P. Bos et al. (2007) *Ann. Rev. Microbiol.*, 61: 191-214). First, the protein is synthesized as a precursor carrying at its N-terminal a leader peptide (LP) including a lipobox. This LP is recognized by Sec pathway and the protein crosses the cytoplasmic membrane. The first amino acid of mature lipoprotein is a cysteine. Processing into mature form takes place on the periplasmic side of the inner membrane, where the thiol group on the side chain of the cysteine residue is modified by the covalent attachment of a diacylglycerol moiety and an amide-linked acyl group is attached to the N-terminus. Both the diacylglyceryl group and the amino-terminal acyl group participate to the anchorage of the lipoprotein to the membrane. The second step consists in the translocation of the acylated protein from the inner membrane to the inner leaflet of the outer membrane. Translocation is mediated by the Lol system (Tokuda H. (2009) *Biosci. Biotechnol. Biochem.*, 73, 465-73). In *N. meningitidis* and other Gram-negative species, cell-surface exposed lipoproteins have been identified. The molecular mechanism responsible for the flipping out of fHbp and other surface lipoproteins from the inner to the outer leaflet of the outer membrane is not known.

fHbp is efficiently incorporated into OMVs released by *Neisseria meningitidis* and fHbp-containing OMVs have been shown to induce potent bactericidal antibodies against *Neisseria meningitidis*. Therefore, such engineered OMVs have been proposed as highly efficacious vaccines (EP 22 55 826 A2).

fHbp has been successfully expressed in *E. coli* and the protein accumulates in the membranes fraction and is efficiently lipidated. Whether or not the protein, when expressed in *E. coli*, is exposed on the surface as it is the case in *Neisseria meningitidis* has not been reported. If a specific flippase is involved in fHbp translocation, when expressed in *E. coli* the protein is expected to be anchored to the inner leaflet of the outer membrane but not surface-exposed. Lipidated fHbp has been shown to induce high titers of bactericidal antibodies and an anti-meningococcus B vaccine based on lipidated fHbp purified from a recombinant *E. coli* strain is close to registration in USA and Europe (L. D. Fletcher et al., (2004) *Inf. Immun.* 72, 2008-2100; Richmond P C, et al., (2012), *The Lancet Infectious Diseases,* 12, 597-607).

*Neisseria meningitidis* NHBA (*Neisseria Heparin* Binding Antigen)

*Neisseria* heparin binding antigen (NHBA) is a *Neisseria meningitidis* surface-exposed lipoproteins which play important roles in pathogenesis. NHBA carries an arginine-rich region responsible for heparin binding, which correlates with an increased survival of *N. meningtidis* in human serum. NHBA fold consists of an 8-strand β-barrel that closely resembles the C-terminal domain of Nm-fHbp suggesting that they derive from a common ancestor (Esposito, V. et al. *J Biol Chem,* 2011. 286(48), 4167-75.

Consistent with its biological role NHBA extend out of the bacterial surface and is accessible to antibodies with bactericidal activity.

*Aggregatibacter actinomycetemcomitans* Factor H Binding Protein (Aa-fHbp)

*A. actinomycetemcomitans* is a human pathogen associated with aggressive periodontitis and endocarditis (van Winkelhoff, A. J. and J. Slots, *Periodontol* 2000, 1999. 20, 122-35; Henderson, B., J. M. Ward, and D. Ready, *Periodontol* 2000, 2010. 54(1), 78-105).

The genome sequence of the pathogen revealed the presence of an Open Reading Frame (ORF) encoding a lipoprotein (Aa-fHbp) sharing 41% amino acid identity with Nm-fHbp var.1 (FIG. 24A). Recent proteomic analyses showed that Aa-fHbp localized in the culture supernatants and/or in OMVs of *A. actinomycetemcomitans* (Kieselbach, T., et al., *PLoS One,* 2015. 10(9), e0138591; Zijnge, V., T. Kieselbach, and J. Oscarsson, *PLoS One,* 2012. 7(7), e41662). Although no direct evidence has been reported so far on the localization of Aa-fHbp, its predicted Factor H binding capacity strongly suggests that the protein protrudes out of the outer membrane of *A. actinomycetemcomitans.*

*Escherichia coli* Maltose Binding Protein

The Maltose Binding Protein (MBP) is a periplasmic protein that specifically binds maltose and maltodextrins, with highest affinity for maltotriose (Schwartz et al., (1976) *Eur. J. Biochem.* 71, 167-170; Szmelcman et al., (1976) *Eur. J. Biochem.,* 65, 13-19; Wandersman et aL, (1979) *J. Bacteriol,* 140, 1-13). Studies on the binding specificity have suggested that the binding site recognizes the glycosidic bond linking the glucose moities of maltose. MBP can be purified in dimeric form from bacteria. Maltose induces the conversion of the protein dimers to monomers and upon binding of the substrate, the monomer undergoes a conformational change (Szmelcman et al., (1976) *Eur. J. Biochem.,* 65, 13-19; Zukin, S. (1979) *Biochemistry* 18, 2139-2145).

MBP is synthesized in large amounts. A fully induced cell may contain up to 40,000 monomers. Expression of the malE gene is activated by the MalT protein in the presence of maltose or maltodextrim and by the cyclic AMP receptor protein.

Like most outer membrane and periplasmic proteins, MBP is synthesized initially with an amino-terminal signal peptide which interacts with the cell secretory apparatus and is cleaved during the export process. The MBP precursor is active in binding maltose (Ferenci and Randall (1979) *J. Biol. Chem.* 254, 9979-9981). Interestingly, MBP is essential for the energy-dependent translocation of maltose and maltodextrins through the cytoplasmic membrane.

MBP is extensively used to express proteins in *E. coli* and to increase their solubility. Proteins of interest are usually expressed as MBP-fusions, and this has been shown to prevent aggregation through a mechanism that is not fully understood. MBP can itself be used as an affinity tag for purification of recombinant proteins. The fusion protein binds to amylose columns while all other proteins flow through. The MBP-protein fusion can be purified by eluting the column with maltose. Once the fusion protein is obtained in purified form, the protein of interest is often cleaved from MBP with a specific protease and separated from MBP by ion exchange chromatography.

Since MBP is a periplasmic protein, chimeric MBP carrying a heterologous protein at its C-terminus also accumulates in this bacterial compartment. However, the delivering of MBP chimera to OMVs and their exploitation as immunogens has never been tested.

OmpF

*Escherichia coli* expresses three major Outer Membrane Proteins (OMPs) OmpA, OmpC and OmpF.

OmpA is noncovalently anchored to peptidoglycan, and is constituted by eight β-barrel strands connected by four long loops at the outer membrane surface and three short periplasmic turns. The other two OMPs, OmpF and OmpC, are porins which serve as passive diffusion pores across the outer membrane. Expression of these two proteins is reciprocally regulated by medium osmolarity. OmpF is preferentially produced at low osmolarity, whereas OmpC is almost exclusively produced at high osmolarity. It has been proposed that the larger OmpF pore size is important for efficient nutrient uptake from nutritionally poor media, whereas the smaller OmpC pore size is important to exclude the passage of toxic bile salts across the outer membrane (Ferrario, M. et al., (1995) *J. Bacteriol.* 177, 103-1132).

*E. coli* has a highly sophisticated regulatory system to modulate the reciprocal expression of ompF and ompC. Both are controlled at the transcriptional level by the histidine kinase EnvZ, a transmembrane osmosensor, and the response regulator OmpR, a transcriptional factor (Hall, M. N., and Silhavy, T. J. (1981) *J. Mol. Biol.* 151, 1-15), and also at the translational level by antisense RNAs: micF for ompF mRNA (Mizuno, et al. (1984) *Proc. Natl. Acad. Sci. U.S.A* 81, 1966-1970) and micC for ompC mRNA (Chen, S., Zhang, A., Blyn, L. B., and Storz, G. (2004) *J. Bacteriol.* 186, 6689-66975).

When grown at 37° C. in rich media such as LB or in minimal media, such as M9 medium, supplemented with glycerol, *E. coli* BL21(D3) mostly produces OmpA and OmpF. The two proteins accumulate in the outer membrane vesicles (OMVs) released by the strain and when the ompA gene is inactivated OmpF constitutes more than 50% of total OMV proteins (Fantappiè et al., (2014) *Journal of Extracellular Vesicles*, 3, 24015).

Structurally, OmpF is characterized by the trimeric assembly of monomeric 16-stranded β-barrels, each containing its own hydrophilic pore. Each barrel essentially spans the thickness of the membrane. Except for the third loop that folds inward and constricts the channel opening, seven long loops connect adjacent pairs of β-strands on the extracellular side. Recently each OmpF loop has been systematically deleted with the aim of dissecting their role in pH and voltage sensitivity. Despite the fact that the study did not allow to completely clarify the contribution of the loops in OmpF activity, it nicely demonstrated that the protein can be mutilated in any of its external loop without appreciably effecting the level of expression, membrane integration and overall protein function (Basle et al., (2004) *Protein engineering, design & selection*, 9, 665-672).

No experimental evidence that OmpF-derived chimeras can be generated have been reported so far.

Cancer Vaccines

The notion that the immune system can recognize and mount a response against tumors was postulated in the late nineteenth century by Coley who demonstrated that attenuated bacteria or bacterial products injected into tumor-bearing patients in some cases resulted in tumor regression (Coley W B (1893) *Am. J. Med. Sci.* 105: 487-511). Nearly a century later, it was demonstrated that immunization of mice with mutated tumor cells could induce a protective anti-tumor immune response against non-immunogenic tumor (Van and Boon, (1982) *PNAS*, 79, 4718-4722). Together, these studies set a foundation for cancer immunotherapy research and demonstrated the therapeutic potential of strategies targeting immune modulation for tumor eradication and protection against tumor recurrences. Therefore, the development of cancer vaccines capable of generating an active tumor-specific immune response serves as a promising venue for cancer therapy.

Probably the best example that illustrates the potential of the immune system to fight cancer is given by Sipuleucel-T, the recently approved vaccine for prostate cancer patients. The vaccine is produced by isolating an individual patient's CD54+ white cells via leukapheresis, exposing the isolated cells ex vivo to PA2024, a protein antigen expressed in over 95% of prostate cancers, and infusing the vaccine back into the patient. Sipuleucel-T therefore consists of personalized primed APCs and of a mixed cell suspension containing also monocytes, macrophages, B and T cells, exposed to activated APCs (Lu C. et al. (2011) *Exp. Opin. Biol. Ther.* 11, 99-108). Although complicated and expensive to produce the vaccine clearly indicates that, if properly stimulated, the immune system can control tumor growth and progression.

Other promising cell-based vaccines are being developed by collecting Tumor Infiltrating Lymphocytes (TILs) from freshly dissected tumors, expanding them upon stimulation with tumor antigens (total tumor extracts or selected tumor antigens) and infusing TILs back into the patients (Restifo et al., (2012) *Nature Rev. Immunol.* 12, 269-281). Also this approach has shown to reduce tumor growth and to prolong overall survival.

A more practical way to develop cancer vaccines is to stimulate patient's immune system by injecting into patients specific cancer antigens formulated with proper adjuvants/ immune potentiators (Berinstein N L (2007) *Vaccine* 255, B72-B88). This approach has the great advantage to avoid the complication of collecting immune cells from each patient and of re-injecting them back after activation and/or amplification.

Several trials are ongoing exploiting this strategy. Among the most promising ones are two peptide-based vaccines, Her2-E75 (Nelipepimut-S) (Mittendorff E A et al., (2014) *Annals of Oncology* 25: 1735-1742) and EGFRvIII (Rindopepimut) (Del Vecchio C A et al. (2012), *Expert Rev. Vaccines* 11, 133-144) against Her2-positive breast cancer and glioblastoma, respectively. These vaccines, which are formulated with the immune stimulator GM-CSF, appear to have different mechanisms of action. The first primarily induces cytotoxic CD8+ T cells while the other mostly elicits humoral response.

However, despite demonstrated efficacy in various murine models, cancer vaccines have found little success in the clinic. Although several factors may contribute to the failure of therapeutic cancer vaccines in the clinic, the most important ones are i) the weak immunogenicity of Tumor Associated Antigens (TAAs), ii) central and peripheral immune tolerance to self TAAs, and iii) various immune evasion mechanisms employed by the progressing tumor.

Therefore, the success of therapeutic cancer vaccines may require formulations that induce potent immune responses that overcome immune tolerance to TAAs as well as reverse or inhibit tumor-mediated immune evasion mechanisms.

Human EGFRvIII

Glioblastoma multiforme (GBM) accounts for over 50% of primary brain tumors (Porter K R et al., (2010) *Neuro. Oncol.* 12, 520-527). Although gliomas often respond to radiotherapy, recurrence occurs in most of the patients with a median time to progression of 7 months (Grossman S A et al., (2004) *Semin. Oncol.* 31, 635-644). Tumor recurrence almost inevitably leads to death, the median overall survival of patients being only 15-16 months with surgical resection and combination chemo/radiation therapy (Vredenburgh J J et al. (2007) *J. Clin. Oncol.* 25, 4722-4729; Stupp R et al., (2005) *N. Engl. J. Med.* 352, 987-996).

Abnormal cell signaling by EGF receptor has been implicated in numerous cancers. Physiologically, EGF binds to the monomeric form of its receptor and this leads to receptor dimerization and autophosphorylation, which in turn triggers the downstream signal cascades (Salomon D S et al., (1995) *Crit. Rev. Oncol. Hematol.* 19, 183-232). In the majority of solid tumors, including breast, brain, head-and-neck, non-small-cell lung, renal, ovarian, prostate and colon cancer EGFR is overexpressed (Wong A J et al., (1992) *Proc. Natl Acad. Sci. USA* 89, 2965-2969; Gorgoulis V et al. (1992) *Anticancer Res.* 12, 1183-1187; Irish J C et al. (1993) *Laryngoscope* 103, 42-52; Korc M et al. (1986) *Proc. Natl Acad. Sci. USA* 83, 5141-5144; Moorghen M et al. (1990) *Anticancer Res.* 10, 605-611; Ishikawa J et al., (1990) *Int. J. Cancer* 45, 1018-1021; Zajchowski D et al., (1988) *Cancer Res.* 48, 7041-7047). EGFR overexpression leads to the enhancement of downstream signaling pathways stimulating growth and invasiveness of cancer cells. Furthermore, cell motility and VEGF-mediated angiogenesis is increased, while cell adhesion requirements are reduced.

In addition to overexpression, there is a naturally occurring variant of the EGF receptor called EGFRvIII. This variant was originally identified in GBM, and is now known to occur in up to 60% of primary GBM. EGFRvIII expression mainly occurs as a consequence of gene rearrangement and amplification even though alternative splicing event has also been implicated. Both gene rearrangement and alternative splicing result in an in-frame 801 base pair deletion of exons 2-7. This deletion gives rise to a truncated receptor that maintains its signal peptide, transmembrane, intracellular kinase and autophosphorylation domains, but lacks a significant portion of the extracellular ligand-binding domain, thus rendering EGFRvIII ligand independent and constitutively active. Other tumors have also been shown to express this variant, including lung, breast, ovarian and prostate cancer, but EGFRvIII is only rarely expressed in normal tissue (Moscatello D K et al., (1995) *Cancer Res.* 55, 5536-5539).

The in-frame deletion of the extracellular domain of EGFR creates a novel antigenic epitope which is exquisitely tumor-specific (Humphrey et al., (1990) PNAS, 87, 4207). Therefore, the newly generated epitope can be exploited in active and passive immunization. Indeed, a vaccine has been developed (Rindopepimut) which is based on a 14-amino acid peptide (LEEKKGNYVVTDHC, SEQ ID NO:126) spanning the new epitope conjugated to keyhole limpet hemocyanin (KLH) and formulated with GM-CSF. A number of Phase II clinical trials in EGRFvIII-positive GBM patients have demonstrated that vaccination with Rindopepimut resulted in significantly higher progression-free and overall survival times (Del Vecchio et al., (2012) *Exp. Rev.* 11, 133). The vaccine is highly promising, but it has margins for improvement. For instance, the immune responses could be optimized. In one clinical trial GMTs were below 910 ng/ml with 6 responders out of 14 patients, and in a second trial all 22 enrolled patients responded but after as many as eight vaccine injections. Furthermore, the vaccine production process is relatively complex (three components with a chemical conjugation). Therefore, the development of an easy-to-produce vaccine with enhanced immunogenicity properties is highly desirable.

Human FAT-1

Human FAT gene family is a subclass of the cadherin superfamily, composed of four giant proteins (FAT1-4) of 500-600 kDa sharing structural similarities from invertebrates to mammals. Human FAT1 is a type 1 transmembrane protein carrying 34 cadherin repeats, five EGF-like repeats, a laminin A-G domain in the extracellular region and a cytoplasmic tail (Dunne, J. et al., (1995) *Genomics* 30, 207-23). The protein undergoes a proteolytic cleavage by Furin and is predicted to be further cleaved by γ secretase so that its intracellular domain (ICD) can translocate into the nucleus and directly activate cell signaling. FAT1 ICD also interacts with Ena/VAPS and Scribble, promotes actin-mediated cell migration and inhibits YAP1-mediated cell proliferation (Moeller, M. J. et al., (2004) *The EMBO journal*, 23, 3769-79). In addition, FAT1 ICD also interacts with β-catenin and prevents its translocation to the nucleus (Morris, L. G. T. et al., (2013) *Nature Genetics* 45, 253-61).

Alteration of FAT1 expression and function has been clearly associated to several human cancers however its role in tumors is controversial.

Several publications provide evidence that in many tumors including oral cancer, astrocytoma, glioblastoma and ductal carcinoma FAT1 acts as a tumor suppressor (Chosdol, K. et al., (2009) *BMC Cancer*, 9, 5; Nakaya, K. et al., (2007) *Oncogene*, 26, 5300-8; Settakorn, J. et al., (2005) *Journal of Clinical Pathology*, 58, 1249-54). Indeed, it has been shown that FAT1 depletion leads to a significant stimulation of cell growth and proliferation, while its expression robustly suppresses tumor growth (Morris, L. G. T. et al., (2013) *Cell Cycle* (Georgetown, Tex.), 12, 1011-2; Morris, L. G. T. et al., (2013) *Nature Genetics* 45, 253-61). Furthermore, FAT1 gene falls within the genomic locus 4q35, a highly prevalent region of deletion in many types of human cancers. FAT1 deletion or loss of heterozygosity have been described in oral cancer (Nakaya, K. et al., (2007) *Oncogene*, 26, 5300-8), astrocytoma and glioblastoma (Chosdol, K. et al., (2009) *BMC Cancer*, 9, 5). Finally, in cholangiocarcinoma FAT1 shows a reduced plasma membrane localization (Settakorn, J. et al., (2005) *Journal of Clinical Pathology*, 58, 1249-54) and in invasive breast cancer is preferentially down-regulated (Kwaepila, N. et al., (2006) *Pathology*, 38, 125-31).

By contrast, in other cancers such as acute myeloid leukemia (AML), pre-B acute lymphoblastic leukemia (ALL) and T-ALL (De Bock, C. E. et al., (2012) *Leukemia*, 26, 918-26) FAT1 has been described to act as tumor promoter. FAT1 appears to be upregulated in hepatocarcinoma (Valletta, D. et al., (2014) *Carcinogenesis*, 35, 1407-15) and leukemia (de Bock et al. 2012). Furthermore, FAT1 up-regulation is an unfavorable prognostic factor for precursor B-cell acute lymphoblastic leukemia patients (De Bock, C. E. et al., (2012) *Leukemia*, 26, 918-26). Finally, recent studies in melanoma and pancreatic cancer have demonstrated that FAT1 undergoes an aberrant processing and an altered localization compared to normal cells (De Bock, C. E. et al., (2012) *Leukemia*, 26, 918-26).

Most recently, (PCT/EP2014/062419(Wo2014/198919) it was discovered that FAT1 is expressed in a large fraction of early and late stage CRCs. Moreover, a murine monoclonal antibody (mAb198.3) was isolated that selectively binds the surface of different FAT1-positive colon cancer cell lines and, upon binding, it is efficiently internalized. mAb198.3 also showed an intrinsic tumor-inhibiting activity in mouse models of human colon cancer xenografts.

mAb198.3 was shown to recognize an epitope present on cadherin domain 8 (D8) and cadherin domain 12 (D12), and antibody binding was efficiently abrogated in the presence of the synthetic peptide IQVEATDKDLGPNGHV-TYSIVTDTD (SEQ ID NO:6) designed on the basis of the amino acid sequence of D8 domain.

Overall, this study provides the proof of concept that mAb198.3 could be exploited as novel tools for the treatment of CRC and paves the way to the use of FAT1 as an anti-CRC vaccine component.

Human MUC-1

Human mucin 1 (MUC1) is a large glycoprotein expressed at relative low level on the apical surface of healthy ductal epithelial cells. A peculiar characteristic of MUC1 is the presence of a region of variable number of tandem repeats (VNTR) in its extracellular domain. In particular, the VNTR region is constituted by a 20-amino acid sequence (PDTRPAPGSTAPPAHGVTSA SEQ ID NO:127) that repeats an average 20-150 times. In healthy epithelia, the VNTR is highly glycosylated on serines and threonines with long and branched O-linked carbohydrates.

During tumorigenesis, MUC1 loses polarity and its expression is highly upregulated. Furthermore, in tumor cells MUC1 is aberrantly hypoglycosylated. This is due to the downregulation of glycosyltransferases and the upregulation of sialyltransferases in tumor cells resulting in premature termination of glycosylation and expression of novel carbohydrate structures. This aberrant MUC1 expression is found in diverse kinds of human cancers including colon, lung, pancreas, breast, ovarian, prostate, kidney, stomach and head and neck (Ho S B et al., (1993) *Cancer Res* 53, 641-51; Baldus S E et al., (2002) *Histopathology* 40, 440-9; Rabassa M E et al. (2006) *BMC Cancer* 6, 253).

Abnormal expression and reduced glycosylation make MUC1 immunogenic. Cytotoxic T lymphocytes (CTLs) specific for VNTR epitopes have been found in pancreatic, breast and ovarian cancer patients Barnd, D. L. et al. (1989) *Proc. Natl. Acad. Sci. USA* 86, 7159-7163; Jerome, K. R. et al. (1991) *Cancer Res.* 51: 2908-2916; Ioannides, C. G. et al. (1993) *J. Immunol.* 151: 3693-3703). Interestingly, it has been found that peptide epitopes as well as novel truncated glycopeptide epitopes are presented by MHCI and induce MHC-restricted, MUC1-specific CTLs (Vlad, A. M. et al. (2002) *J. Exp. Med.* 196: 1435-1446). Furthermore, MUC1-specific antibodies have been found in cancer patients and have been associated to a survival benefit in breast, pancreatic, and ovarian cancer patients (vonMensdorff-Pouilly, S. et al. (2000) *J. Clin. Oncol.* 18: 574-583; Hamanaka, Y. et al. (2003) *Int. J. Cancer.* 103: 97-100; Pinheiro, S. P. et al. (2010) *Cancer Epidemiol. Biomarkers Prev.* 19: 1595-1601).

Since its first characterization as a human tumor-associated antigen recognized by T cells MUC1 has been studied as a highly promising antigen for passive (adoptive transfer of antibodies or T cells) and active (vaccines) immunotherapy of multiple human cancers (Kimura T. and Finn O J (2013) *Expert Opin. Biol. Ther.* 13: 35-49). However, the numerous clinical trials conducted over the last twenty years to demonstrate the potential of MUC1 in immunotherapy were somehow disappointing. Some protection was clearly observed but below the expectations and a MUC1-based cancer immunotherapy still needs substantial optimization before being considered as a valid therapeutic option for the treatment of cancer.

DISCLOSURE OF THE INVENTION

The inventors have found that bacterial Outer Membrane Vesicles (OMVs) loaded with tumor antigens fused to suitable bacterial proteins, are able to induce potent antigen-specific immune response. In particular it was observed that the following bacterial proteins: Factor H Binding Protein (fHbp), Maltose Binding Protein (MBP) and Outer Membrane Protein-F (Omp-F), are able to deliver the tumor antigen to the outer membrane compartment and correctly expose the antigen on the vesicular surface.

Accordingly, the invention provides a fusion protein comprising a bacterial protein selected from Factor H Binding Protein (fHbp), Maltose Binding Protein (MBP), Outer Membrane Protein-F (Omp-F), *Neisseria* heparin binding antigen (NHBA) and *Aggregatibacter actinomycetemcomitans* Factor H binding protein (Aa-fHbp), which is fused to one or more copies of a tumor antigen protein.

Preferably, in the fusion protein, the carboxyl end of the bacterial protein is linked to the amino terminus of the tumor antigen, directly or by interposition of a peptide linker. When the bacterial protein is OmpF, the tumor antigen can be inserted in—or replace—any of its external loops.

The fusion protein can contain one or more copies, preferably up to 10 copies, of tumor antigens, optionally separated by a peptide linker. As herein intended, the term "linker" designates any peptide sequence containing from 1 to 20 aa and preferably 2 to 4 aa.

The Factor H Binding Protein (fHbp) according to the invention includes the full-length protein or its domain A.

In preferred embodiments, the bacterial proteins are selected from the group consisting of: fHbp, SEQ ID NO:1; fHbpDomA, SEQ ID NO:2; OMP, SEQ ID NO:3 and MBP, SEQ ID NO:4; NHBA, SEQ ID NO:109; Aa-fHbp, SEQ ID NO:110.

Any tumor antigen can be potentially used to construct the fusion protein according to the invention and particularly the following:

(a) cancer-testis antigens including NY-ESO-1, SSX2, SCP1 as well as RAGE, BAGE, GAGE and: AGE family polypeptides, for example, GAGE-1 GAGE-2, MAGE-1, MAGE-2, MAGE-3, MAGE-4, MAGE-5, MAGE-6, and MAGE-12, which can be used, for example, to address melanoma, lung, head and neck. NSCLC, breast, gastrointestinal, and bladder tumours; (b) mutated antigens, including p53, associated with various solid tumours, e.g., colorectal, lung, head and neck cancer; p21/Ras associated with, e.g., melanoma, pancreatic cancer and colorectal cancer; CDK4, associated with, e.g., melanoma; MUM1 associated with, e.g., melanoma; caspase-8 associated with, e.g., head and neck cancer; CIA 0205 associated with, e.g., bladder cancer; HLA-A2-R1.701, beta catenin associated with, e.g., melanoma; TCR associated with, e.g., T-cell non-Hodgkin lymphoma; BCR-abl associated with, e.g., chronic myelogenous leukemia; triosephosphate isomerase; MA 0205; CDC-27, and LDLR-FUT; (c) over-expressed antigens, including, Galectin 4 associated with, e.g., colorectal cancer; Galectin 9 associated with, e.g., Hodgkin's disease; proteinase 3 associated with, e.g., chronic myelogenous leukemia; WT 1 associated with, e.g., various leukemias; carbonic anhydrase associated with, e.g., renal cancer;

aldolase A associated with, e.g., lung cancer; FRAME associated with, e.g., melanoma; HER-2/neu associated with, e.g., breast, colon, lung and ovarian cancer; mammaglobin, alpha-fetoprotein associated with, e.g., hepatoma; KSA associated with, e.g., colorectal cancer; gastrin associated with; e.g., pancreatic and gastric cancer; telomerase catalytic protein; MUC-1 associated with; e.g., breast and ovarian cancer; G-250 associated with, e.g., renal cell carcinoma; p53 associated with, e.g., breast, colon cancer; and carcinoembryonic antigen associated with, e.g., breast cancer, lung cancer, and cancers of the gastrointestinal tract such as colorectal cancer; (d) shared antigens, including melanoma-melanocyte differentiation antigens such as MART-1; Melan A; gplOO; MC1R; melanocyte-stimulating hormone receptor; tyrosinase; tyrosinase related protein-1/TRP1 and tyrosinase related protein-2/TRP2 associated with, e.g., melanoma; (e) prostate associated antigens including PAP, PSA, PSMA, PSM-P1, PSM-P2, associated with e.g., prostate cancer; (f) immunoglobulin idiotypes associated with myeloma and B cell lymphomas. In certain embodiments, the one or more TAA can be selected from pi 5, Hom/Mel-40, H-Ras, E2A-PRL, F14-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, pl85erbB2, pl 80erbB3-3, c-met, mn-23H1, TAG-72-4, CA 19-9, CA 72-4, CAM 17.1, NuMa, K-ras, pi 6, TACE, PSCA, CT7, 43-9F, 5T4, 791 Tgp72, beta-HCG, BCA225, BTAA, CA 125, CA 15-3 (CA 27.29\13CAA), CA 195. CA 242, CA-50, CAM43, CD68\KP1, CO-029, FGF-5, Ga733 (EpCAM), 175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS.

Preferably the tumor antigen is the entire sequence, a portion of it, or specific immunogenic epitopes of one of the following human proteins: TCTN1 (Gene ID: ENSG00000204852), TCTN2 (Gene ID: ENSG00000168778), TCTN3 (Gene ID: ENSG00000119977), HIGD2A (Gene ID: ENSG00000146066), HIGD2B (Gene ID: ENSG00000175202), C4ORF32 (Gene ID: ENSG00000174749), FAM62A (E-SYT1, Gene ID: ENSG00000139641), COLEC11 (Gene ID: ENSG00000118004), FSTL5 (Gene ID: ENSG00000168843), FAM82A2 (Gene ID: ENSG00000137824), SCARA5 (Gene ID: ENSG00000168079), VSTM1 (Gene ID: ENSG00000189068), RNF5 (Gene ID: ENSG00000183574), UNQ6126 (Gene ID: gi|169216088), DPY19L3 (Gene ID: ENSG00000178904), SLC39A10 (gene ID: ENSG00000196950), GPR107 (Gene ID: ENSG00000148358), COL20A1 (Gene ID: ENSG00000101203), GLT25D2 (Gene ID: ENSG00000198756), SYTL3 (Gene ID: ENSG00000164674), DENND1B (Gene ID: ENSG00000162701), C6orf98 (Gene ID: EG: 387079), FAM69B (Gene ID: ENSG00000165716), EMID1 (Gene ID: OTTHUMG00000030824), KLRG2 (GENE ID: ENSG00000188883), ERMP1 (GENE ID: ENSG00000099219), VMO1 (Gene ID: ENSG00000182853), C9orf46 (Gene ID: ENSG00000107020), FLJ37107 (Gene ID: ENSG00000177990), YIPF2 (Gene ID: ENSG00000130733), TRYX3 (PRSS58, ENSG00000258223.2), C14orf135 (Gene ID: ENSG00000126773), ANGPTL7 (Gene ID: ENSG00000171819), TPCN2 (Gene ID: ENSG00000162341), C18orf19 (Gene ID: ENSG00000177150), OLFML1 (Gene ID: ENSG00000183801), LYPD4 (Gene ID: ENSG00000101203), MEGF8 (Gene ID: ENSG00000105429), FLJ42986 (Gene ID: ENSG00000196460), SLC46A1 (Gene ID: ENSG00000076351), FAM180A (Gene ID: ENSG00000189320), CRISP-3 (GENE ID: ENSG00000096006)

These tumor antigens are disclosed in WO2010/086162, WO2010/086163, WO2011/051278, WO2011/051276, WO2011/051277, WO2011/051280, WO2011/051271, WO2011/135068, WO2014/198919, all in the applicant's name, the content of which is herein incorporated by reference.

More preferably the tumor antigen is selected from hEGFRvIII, hFAT-1 and hMUC-1, or an immunogenic fragment thereof. In preferred embodiments, the immunogenic fragments are selected from the following peptide sequences: LEEKKGNYVVTDH (EGFRvIII, SEQ ID NO:5), IQVEATDKDLGPNGHVTYSIVTDTD (hFAT-1, SEQ ID NO:6), GVTSAPDTRPAPGSTAPPAH (hMUC-1, SEQ ID NO:7).

In preferred invention embodiments the fusion protein is selected from the group consisting of NOs:8 through 25, SEQ ID NOs:111 and 112.

The invention also provides an isolated bacterial outer membrane vesicle (OMV) loaded with a fusion protein as above defined. The isolated OMV can contain a fusion protein carrying one species of tumor antigen or a plurality of fusion proteins carrying different tumor antigens.

The OMV can be isolated and purified from Gram-negative bacteria, including species from any of genera *Escherichia, Shigella, Neisseria, Moraxella, Bordetella, Borrelia, Brucella, Chlamydia, Haemophilus, Legionella, Pseudomonas, Yersinia, Helicobacter, Salmonella, Vibrio*, etc. For example, the vesicles may be from *Bordetella pertussis, Borrelia burgdorferi, Brucella melitensis, Brucella ovis, Chlamydia psittaci, Chlamydia trachomatis, Moraxella catarrhalis, Escherichia coli* (including extraintestinal pathogenic strains), *Haemophilus influenzae* (including non-typeable stains), *Legionella pneumophila, Neisseria gonorrhoeae. Neisseria meningitidis, Neisseria lactamica, Pseudomonas aeruginosa, Yersinia enterocolitica, Helicobacter pylori, Salmonella enterica* eluding serovar typhi and typhimurium), *Vibrio cholerae, Shigella dysenteriae, Shigella flexneri, Shigella boydii* or *Shigella sonnei*.

*N. meningitidis* OMVs have a proven safety record in humans and so they are a preferred choice. Another useful choice is *E. coli* vesicles, for example the BL21(DE3) strain (see Methods).

OMVs are prepared artificially from bacteria, and may be prepared using detergent treatment (e.g. with deoxycholate), or by non-detergent means (e.g. see WO2004/019977). Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc.) at a pH sufficiently high not to precipitate the detergent (WO01/91788). Other techniques may be performed substantially in the absence of detergent (WO2004/019977) using techniques such as sonication, homogenisation, microfluidisation, cavitation, osmotic shock, grinding, French press, blending, etc. Methods using no or low detergent can retain useful antigens (WO2004/019977), Thus a method may use an OMV extraction buffer with about 0.5% deoxycholate or lower e.g. about 0.2%, about 0.1%, <0.05% or zero.

Bacterial vesicles can conveniently be separated from whole bacterial culture by filtration e.g. through a 0.22 μm filter. Bacterial filtrates may be clarified by centrifugation, for example high-speed centrifugation {e.g. 20,000×g for about 2 hours). Another useful process for OMV preparation is described in WO2005/004908 and involves ultrafiltration on crude OMVs, instead of high-speed centrifugation. The process may involve a step of ultracentrifugation after the ultrafiltration takes place. A simple process for purifying bacterial vesicles is described in WO2011/036562, comprising: (i) a first filtration step in which the vesicles are separated from the bacteria based on their different sizes, with the vesicles passing into the filtrate e.g. using a function (Basle et al., (2004) *Protein engineering, design & selection*, 9, 665-672).

In a further embodiment, the invention provides an immunogenic composition comprising a bacterial outer membrane vesicle as herein disclosed, together with pharmaceutical acceptable vehicles and excipients. The immunogenic composition may contain a mixture of outer membrane vesicles differing from each other for the type of tumor antigen, for the bacterial protein, or both.

The compositions of the invention for administration to subjects are preferably vaccine compositions. Vaccines according to the invention may either be prophylactic {e.g. to prevent cancer) or therapeutic {e.g. to treat cancer). Pharmaceutical compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated {e.g. non-human primate, primate, etc.), the capacity of the individual's immune system to stimulate antibody production, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the amount of protein per dose. The amount of OMVs in compositions of the invention may generally be between 10 and 500 μg, preferably between 25 and 200 μg, and more preferably about 50 μg or about 100 μg.

Compositions of the invention may be prepared in various liquid forms. For example, the compositions may be prepared as injectables, either as solutions or suspensions. The composition may be prepared for pulmonary administration e.g. by an inhaler, using a fine spray. The composition may be prepared for nasal, aural or ocular administration e.g. as spray or drops, and intranasal vesicle vaccines are known in the art. Injectables for intramuscular administration are typical. injection may be via a needle (e.g. a hypodermic needle), but needle-free injection may alternatively be used.

The OMVs and the immunogenic compositions according to the invention are conveniently used for the stimulation of an immune response against tumor in a subject in need thereof. Particularly they can be used for the prevention or treatment of different types of tumor, including but not limited tobronchogenic carcinoma, nasopharyngeal carcinoma, laryngeal carcinoma, small cell and non-small cell lung carcinoma, lung adenocarcinoma, hepatocarcinoma, pancreatic carcinoma, bladder carcinoma, colon carcinoma, breast carcinoma, cervical carcinoma, ovarian carcinoma, or lymphocytic leukaemias, prostate cancer.

In a preferred embodiment, the isolated bacterial outer membrane vesicles or the immunogenic composition are used in the prevention or treatment of tumors selected from breast, brain, head-and-neck, non-small cell lung, renal, ovarian, kidney, stomach, prostate and colon cancer, oral cancer, astrocytoma, glioblastoma, ductal carcinoma, cholangiocarcinoma, hepatocarcinoma, acute myeloid leukemia, acute lymphoblastic leukemia, melanoma, pancreatic cancer and prostate cancer.

DISCLOSURE OF PREFERRED EMBODIMENTS

In one embodiment, the DNA coding sequence of a selected tumor antigen is fused to the 3' end of the gene coding for the full length *Neisseria meningitidis* Factor H Binding Protein (fHbp) (SEQ ID NO:85) and such gene fusion is inserted into an appropriate plasmid expression vector in order to drive the expression of a fusion protein constituted by fHbp carrying the foreign antigen at its carboxyl terminus. Because of the presence of the fHbp leader sequence and lipidation site the fusion protein is delivered to the bacterial outer membrane and subsequently incorporated into OMVs. It was surprisingly found that tumor antigens fused to the C-terminus of fHbp are exposed to the surface of *E. coli* cells and of its derived OMVs.

In another embodiment, the DNA coding sequence of a selected tumor antigen is fused to the 3' end of the gene coding for the domain A of fHbp (fHbpDomA, SEQ ID NO:86) and such gene fusion is inserted into an appropriate plasmid expression vector in order to drive the expression of a fusion protein constituted by fHbp carrying the foreign antigen at its carboxyl terminus. Because of the presence of the fHbp leader sequence and lipidation site the fusion protein is delivered to the bacterial outer membrane and subsequently incorporated into OMVs. It has been surprisingly found that when expressed in *E. coli*, fHbpDomA is delivered to the outer membrane and tumor antigens fused to the C-terminus of fHbpDomA are exposed to the surface of *E. coli* cells and of its derived OMVs.

In another embodiment, the DNA coding sequence of a selected tumor antigen is fused to the 3' end of the full length gene coding for the *Neisseria meningitidis* NHBA (SEQ ID NO:113) and such gene fusion is inserted into an appropriate plasmid expression vector in order to drive the expression of a fusion protein constituted by NHBA carrying the foreign antigen at its carboxyl terminus. Because of the presence of the NHBA leader sequence and lipidation site the fusion protein is delivered to the bacterial outer membrane and subsequently incorporated into OMVs. It has been surprisingly found that when expressed in *E. coli*, NHBA is delivered to the outer membrane and tumor antigens fused to the C-terminus of NHBA are exposed to the surface of *E. coli* cells and of its derived OMVs.

In another embodiment, the DNA coding sequence of a tumor antigen of interest is fused to the 3' end of the gene coding for the *E. coli* Maltose Binding Protein (MBP, SEQ ID NO:100). Such gene fusion is inserted into an appropriate plasmid expression vector in order to drive the expression of a fusion protein constituted by MBP carrying the foreign antigen at its carboxyl terminus. It has surprisingly been found that such fusion protein can be efficiently incorporated into OMVs.

In another embodiment, the DNA coding sequence of a selected tumor antigen is inserted into coding sequence of ompF in correspondence of DNA regions coding for the external loops of the protein. Such gene fusions are inserted into appropriate plasmid expression vectors in order to drive the expression of engineered OmpF in which any of the external loop is replaced with the foreign antigen. It has surprisingly been found that the engineered OmpF are efficiently integrated into the *E. coli* outer membrane and the tumor antigen is efficiently exposed on the bacterial surface, and that the engineered OmpF is also efficiently incorporated into OMVs.

In a further embodiment, the tumor antigen is the EGFRvIII peptide LEEKKGNYVVTDH (SEQ ID NO:5). The DNA sequence coding for one or more copies of the EGFRvIII peptide is ligated at the 3' end of gene encoding the full length fHbp in order to generate gene chimeras encoding fHbp with one or more copies of EGFRvIII peptide fused at their C-terminus. A relevant aspect of this invention is that when the gene chimera are expressed in *E. coli* the hybrid proteins are efficiently delivered to the outer membrane and incorporated into OMVs. Remarkably, OMVs carrying fHbp-EGFRvIII peptide fusions induce potent anti-EGFRvIII peptide immune responses.

In another embodiment, the DNA sequence coding for one or more copies of the EGFRvIII peptide is ligated at the 3' end of gene encoding fHbpDomA (SEQ ID NO:86) in order to generate gene chimera encoding fHbp with one or more copies of EGFRvIII peptide fused at its C-terminus. A relevant aspect of this invention is that when the gene chimera are expressed in *E. coli* the hybrid proteins are efficiently delivered to the outer membrane and incorporated into OMVs. Remarkably, OMVs carrying fHbpDomA-EGFRvIII peptide fusions induce potent anti-EGFRvIII peptide immune responses.

In another embodiment, the DNA sequence coding for one or more copies of the EGFRvIII peptide is ligated at the 3' end of gene encoding the full length NHBA (SEQ ID NO: 113) in order to generate gene chimeras encoding NHBA with one or more copies of EGFRvIII peptide fused at their C-terminus. A relevant aspect of this invention is that when the gene chimera are expressed in *E. coli* the hybrid proteins are efficiently delivered to the outer membrane and incorporated into OMVs.

In yet another embodiment, the DNA sequence coding for one copy of the EGFRvIII peptide is ligated at the 3' end of gene encoding MBP (SEQ ID NO:100) in order to generate a gene chimera encoding MBP with one copy of EGFRvIII peptide fused at its C-terminus. A relevant aspect of this invention is that when the gene chimera is expressed in *E. coli* the hybrid protein is efficiently incorporated into OMVs. Remarkably, OMVs carrying MBP-EGFRvIII peptide fusion induce potent anti-EGFRvIII peptide immune responses.

In a further embodiment, the DNA sequence coding for one or more copies of EGFRvIII peptide is inserted into coding sequence of ompF in correspondence of DNA regions coding for the external loops of the proteins. A relevant aspect of this invention is that when the gene chimeras are expressed in *E. coli* the hybrid proteins are efficiently delivered to the outer membrane and incorporated into OMVs. Remarkably, OMVs carrying OmpF-EGFRvIII peptide fusions expose the EGFRvIII peptide to the surface of OMVs and are accessible to anti-EGFRvIII antibody binding.

In another embodiment, the foreign antigen is the FAT1-derived peptide IQVEATDKDLGPNGHVTYSIVTDTD (SEQ ID NO:6). The DNA sequence coding for one or more copies of FAT1 peptide is ligated at the 3' end of gene encoding the full length fHbp in order to generate gene chimeras encoding fHbp with one or more copies of FAT1 peptide fused at their C-terminus. A relevant aspect of this invention is that when the gene chimeras are expressed in *E. coli* the hybrid proteins are efficiently delivered to the outer membrane and incorporated into OMVs. Remarkably, OMVs carrying fHbp-FAT1 peptide fusions induce potent anti-FAT1 peptide immune responses.

In yet another embodiment, the DNA sequence coding for one or more copies of the FAT1 peptide is ligated at the 3' end of gene encoding fHbpDomA (SEQ ID NO:86) in order to generate gene chimeras encoding fHbp with one or more copies of FAT1 peptide fused at their C-terminus. A relevant aspect of this invention is that when the gene chimeras are expressed in *E. coli* the hybrid proteins are efficiently delivered to the outer membrane and incorporated into OMVs. Remarkably, OMVs carrying fHbpDomA-FAT1 peptide fusions induce potent anti-FAT1 peptide immune responses.

In another embodiment, the DNA sequence coding for one or more copies of the FAT1 peptide is ligated at the 3' end of the gene encoding MBP (SEQ ID NO:100) in order to generate gene chimeras encoding fHbp with one or more copies of FAT1 peptide fused at their C-terminus. A relevant aspect of this invention is that when the gene chimeras are expressed in *E. coli* the hybrid proteins are efficiently delivered to the periplasm and incorporated into OMVs. Remarkably, OMVs carrying MBP-FAT1 peptide fusions induce potent anti-EGFRvIII peptide immune responses.

In a further embodiment, the foreign antigen is the MUC1-derived peptide GVTSAPDTRPAPGSTAPPAH (SEQ ID NO:7). The DNA sequence coding for one or more copies of MUC1 peptide is ligated at the 3' end of gene encoding the full length fHbp (SEQ ID NO:85) in order to generate gene chimeras encoding fHbp with one or more copies of MUC1 peptide fused at their C-terminus. A relevant aspect of this invention is that when the gene chimeras are expressed in *E. coli* the hybrid proteins are efficiently delivered to the outer membrane and incorporated into OMVs. Remarkably, OMVs carrying fHbp-MUC1 peptide fusions induce potent anti-MUC1 peptide immune responses.

In a further embodiment, the DNA sequence coding for one or more copies of the MUC1 peptide is ligated at the 3' end of gene encoding fHbpDomA (SEQ ID NO:86) in order to generate gene chimeras encoding fHbpDomA with one or more copies of MUC1 peptide fused at their C-terminus. A relevant aspect of this invention is that when the gene chimeras are expressed in *E. coli* the hybrid proteins are efficiently delivered to the outer membrane and incorporated into OMVs. Remarkably, OMVs carrying fHbpDomA-MUC1 peptide fusions induce potent anti-MUC1 peptide immune responses.

In another embodiment, the DNA sequence coding for one or more copies of MUC1 peptide is ligated at the 3' end of gene encoding MBP (SEQ ID NO:100) in order to generate gene chimeras encoding MBP with one or more copies of MUC1 peptide fused at their C-terminus. A relevant aspect of this invention is that when the gene chimeras are expressed in *E. coli* the hybrid proteins are efficiently delivered to the periplasm and incorporated into OMVs. Remarkably, OMVs carrying MBP-MUC1 peptide fusions induce potent anti-MUC1 peptide immune responses.

In another embodiment, the DNA sequence encoding for the *Aggregatibacter actinomycetemcomitans* factor H binding protein (Aa-fHbp, SEQ ID NO:116) gene was cloned in E. coli and used to decorate OMVs. A relevant aspect of this invention is that when the gene is cloned in E. coli the protein is efficiently expressed, delivered to the external side of the outer membrane and incorporated into OMVs.

DESCRIPTION OF THE FIGURES

FIGS. 2A-2B Amino acid and nucleotide sequences of single and triple copy EGFRvIII. (A) Amino acid and nucleotide sequences of single copy EGFRvIII peptide (vIII) (SEQ ID NOs: 146 and 145, respectively). (B) Amino acid and nucleotide sequences of triple copy EGFRvIII peptide (vIIIx3) (SEQ ID NOs: 148 and 147, respectively). Three copies of EGFRvIII are separated and flanked by short linker sequences. To minimize the possibility of recombination between EGFRvIII coding DNA fragments, three different vIII nucleotide sequences were generated, taking advantage of codon degeneracy but considering E. coli BL21 codon usage.

(FIG. 4A) The DNA fragment coding for the tripeptide vIIIx3 was subcloned in pUC plasmid, generating plasmid pUC-vIIIx3. To fuse three copies of EGFRvIII to fHbp full length (FIG. 4B), fHbpDomA (FIG. 4C) and NHBA (FIG. 4D), pET-fHbp, pET-fHbpDomA and pET-NHBA plasmids were PCR-amplified using primers nohisflag/fHbp R2, nohisflag/fHbp A rev2 and NHBA-vIII-3x-v-f/NHBA-vIII-3x-v-r, respectively (Table 1), while the vIIIx3 insert was PCR-amplified from pUC-vIIIx3 using primers vIII-triple fh-wt for /vIII-triple rev, vIII-triple fh-domA for /vIII-triple rev and NHBA-vIII-3x-i-f/NHBA-vIII-3x-i-r, respectively. Finally, the PCR products were used to transform E. coli HK100 cells to allow the recombination of complementary ends, obtaining plasmids pET-fHbpvIIIx3, pET-fHbpDomAvIIIx3 and pET-NHBAvIIIx3. LS: leader sequence; LP: lipobox; A: fHbp domain A; B: fHbp domain B; C: fHbp domain C.

BL21(DE3)/ΔompA (pET-fHbp-FAT1) and BL21(DE3)/ΔompA (pET-fHbpDomA-FAT1) *E. coli* strains were grown in 10 ml LB medium at 37° C. and when the cultures reached $OD_{600}$=0.6, the expression of the fusion proteins was induced by addition of 1 mM IPTG. After 2 hours growth bacteria were collected by centrifugation and incubated with 50 μl of an appropriate dilution of anti-FAT1 mAb198.3 or, as negative controls, with PBS containing 1% BSA or with an unrelated mAb. After 1 hour, bacterial cells were washed with PBS containing 1% BSA and subsequently incubated for 30 minutes on ice with goat anti-mouse antibodies added at a final dilution of 1:200. Finally, after 2 wash steps, pellets were re-suspended in 200 μl of PBS and analyzed with FACS CANTOII. Collected data were analyzed with FlowJo software.

Figure 21:
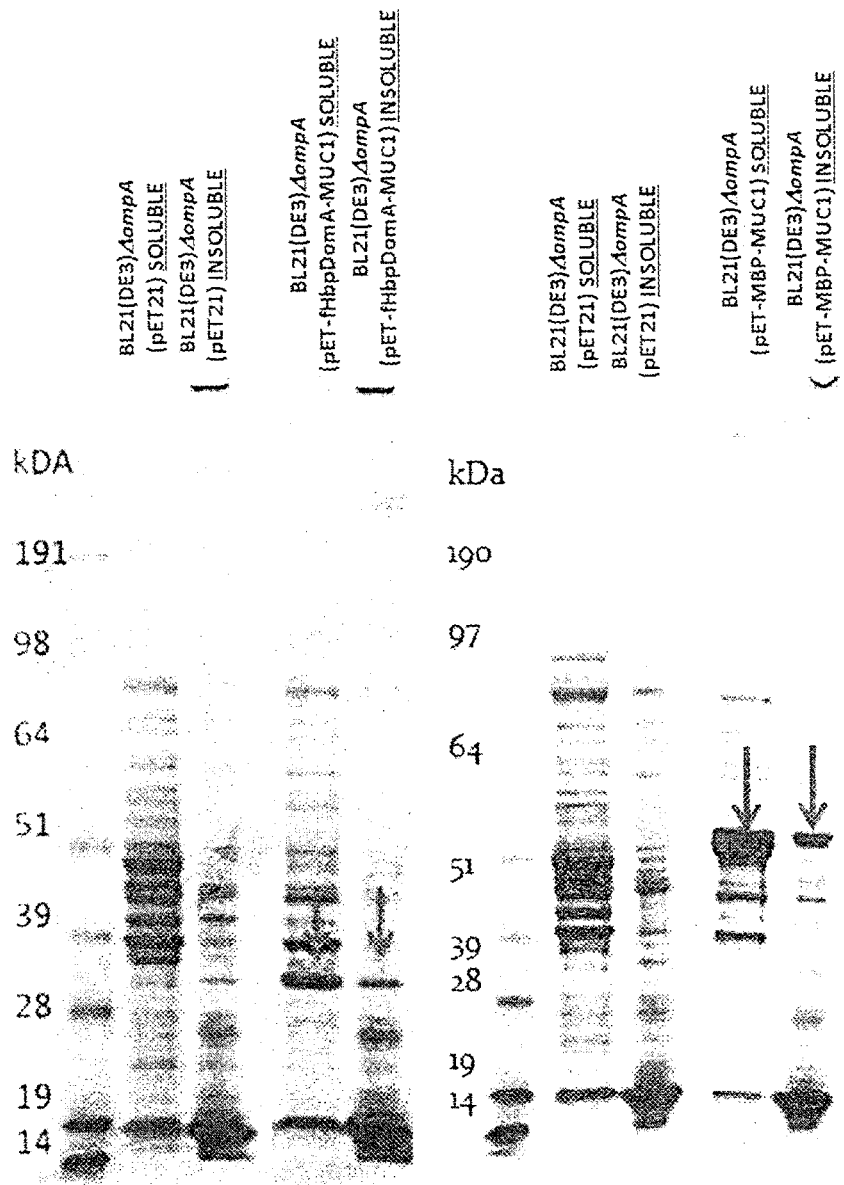

FIG. 21. SDS-PAGE analysis of protein preparations from BL21(DE3)ΔompA recombinant strains expressing fHbpDomA-MUC1 and MBP-MUC1 fusion proteins. Recombinant clones were grown in LB at 37° C. and when the cultures reached OD600=0.6, the expression of the fusion proteins was induced by addition of 1 mM IPTG. After 2 hours growth, the equivalent in volume of 1 OD600 of each bacterial culture was collected, centrifuged at 13,000×g for 5 minutes and pellets were lysed in 200 μl of Bacterial Protein Extraction Reagent (Life Technologies), Lysozime 1 mg/ml, DNAase 10 U/ml and 0.1 mM MgCl2 for 30 minutes. The samples were centrifuged at 13,000×g for 20 minutes to separate the supernatants (soluble fraction) from the pellets (insoluble fraction). The soluble fractions were collected (200 μl) and diluted with 100 μl of 4× SDS-PAGE loading buffer while the pellets were re-suspended in 300 μl of 2× loading buffer. 20 □l of each sample were analyzed by SDS-PAGE. As a negative control, soluble and insoluble protein fractions were also prepared from BL21(DE3)ΔompA strain carrying pET21 cloning vector.

Figure 22:
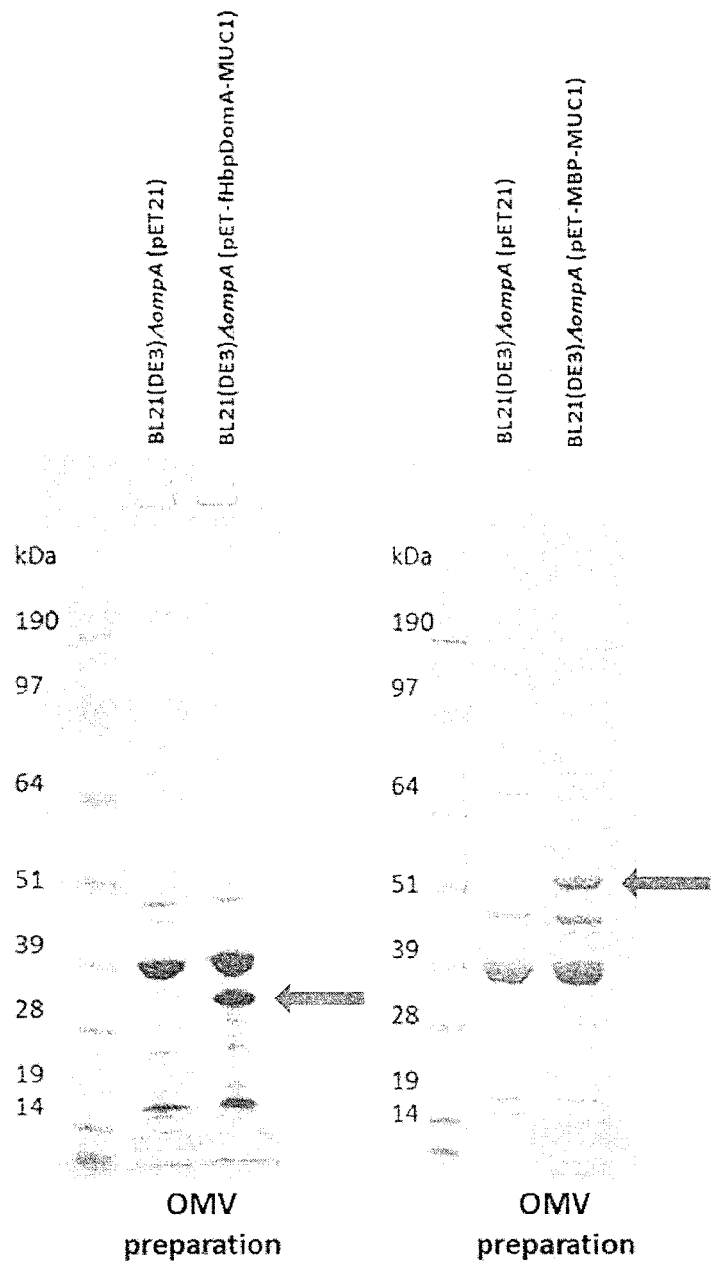

FIG. 22. SDS-PAGE analysis of OMV preparations purified from BL21(DE3)ΔompA recombinant strains expressing fHbpDomA-MUC1 and MBP-MUC1 fusions proteins. BL21(DE3)/ΔompA (pET-fHbpDomA-MUC1) and BL21(DE3)/ΔompA (pET-MBP-MUC1) strains were grown in LB and when the cultures reached an OD600=0.6 1 mM IPTG was added. OMVs were purified from the culture supernatants by using ultrafiltration coupled to ultracentrifugation. 10 μg of total proteins of each OMV preparation were analyzed by SDS-PAGE. As a negative control, OMVs were also prepared from BL21(DE3)ΔompA strain carrying pET21 cloning vector.

Figure 23:
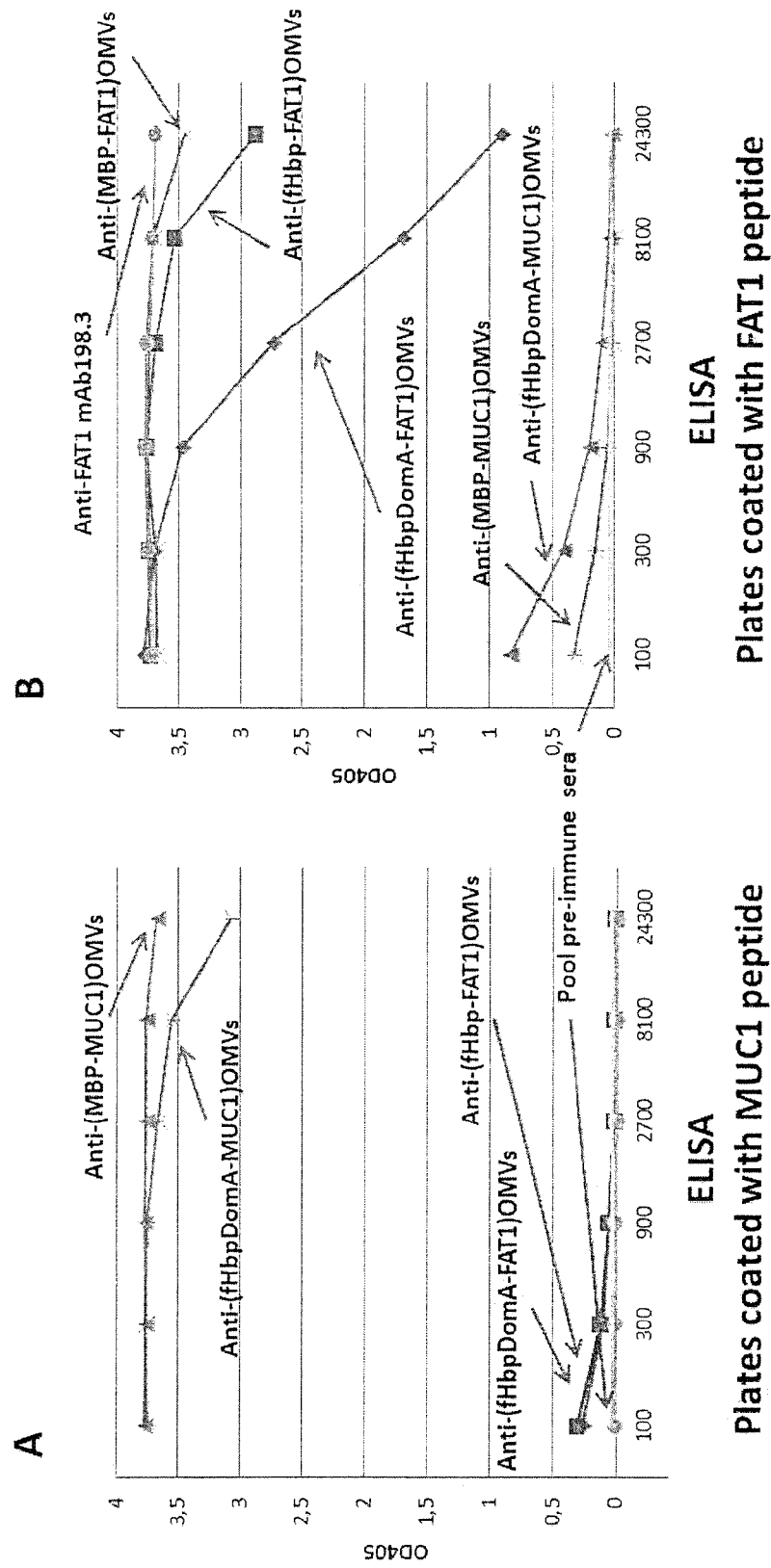

FIG. 23A-23B. Antibody titers elicited in mice immunized with engineered OMVs carrying FAT1 and MUC1 fusion proteins. Engineered OMVs (20 μg) were used to i.p. immunize CD1 mice (5 mice per group) three times at two-week intervals and after two weeks from the third immunization, sera were collected and pooled to analyze anti-MUC1 and anti-FAT1 antibody titers by ELISA. Plates were coated with the synthetic MUC1 peptide GVTSAP-DTRPAPGSTAPPAH (A, SEQ ID NO:7) and synthetic FAT1 peptide IQVEATDKDLGPNGHVTYSIVTDTD (B, SEQ ID NO:6) and different dilutions of pooled sera were incubated at 37° C. for 2 hours. After three washes in PBST, 100 μl of goat anti-mouse antibodies conjugated to alkaline phosphatase (SouthernBiotech, Cat. 1030-04, 1:2.000 dilution) were added to each well and incubated at 37° C. for 1 hour. Finally, after three washes, the phosphatase substrate (4-Nitrophenyl phosphate disodium salt) was added to each well at a concentration of 1 mg/ml (100 μl/well) and after 30 minutes incubation at room temperature in the dark, substrate hydrolysis was measured spectrophotometrically at 405 nm.

FIGS. 24A-24E. Expression, compartmentalization and surface localization of Aa-fHbp in BL21A ompA and derived OMVs.

(FIG. 24A) Protein sequence alignment of Nm-fHbp (SEQ ID NO: 149) and Aa-fHbp (SEQ ID NO: 150). (FIG. 24B) SDS-PAGE analysis of total cell extracts (TL) and OMVs isolated from BL21ΔompA (pET_Aa-fHbp). (FIG. 24C) Western blot analysis of OMVs purified from BL21ΔompA (pET_Aa-fHbp). (FIG. 24D) Assessment of Aa-fHbp localization by FACS analysis. Aa-fHbp detection was carried out using anti-His-tag antibodies. (FIG. 24E) Assessment of Aa-fHbp localization by proteinase K surface shaving.

DETAILED DESCRIPTION OF THE INVENTION

Engineered OMVs Expressing EGFRvIII Peptide

Figure 1:
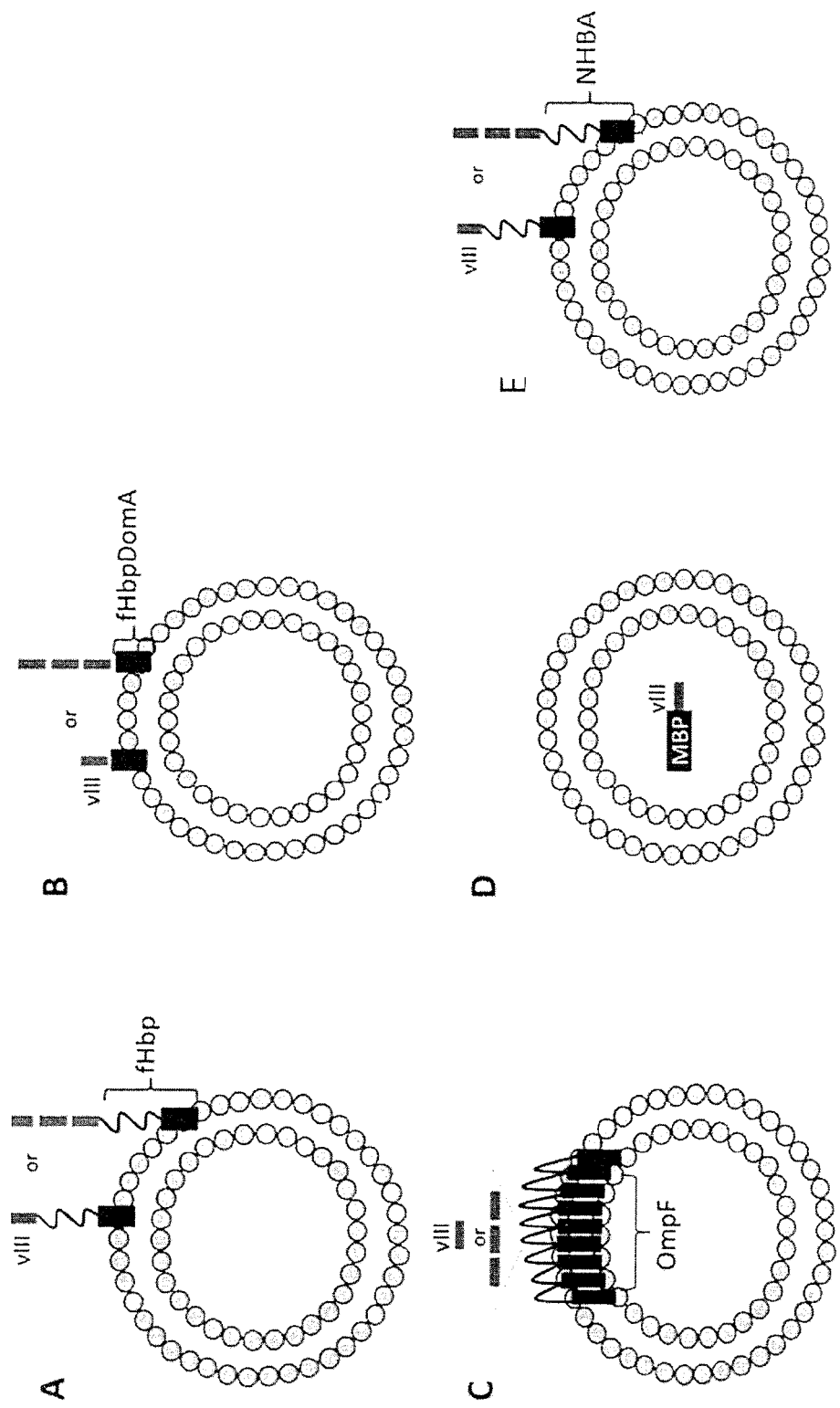
FIGS. 1A-1E. Strategies for decorating bacterial OMVs with the EGFRvIII peptide. (A) A peptide containing one or three copies of EGFRvIII is fused to the C-terminus of factor H binding protein (fHbp) from N. meningitidis MC58. (B) A peptide containing one or three copies of EGFRvIII is fused to the C-terminus of a truncated form of fHbp, lacking domains B and C (fHbpDomA). (C) A peptide containing one or three copies of EGFRvIII replaces one of OmpF external loops. (D) A peptide containing one copy of EGFRvIII is fused to the C-terminus of Maltose Binding Protein (MBP) from E. coli K12-MG1655. (E) A peptide containing one or three copies of EGFRvIII is fused to the C-terminus of neisseria heparin binding antigen (NHBA) from N. meningitidis MC58.

FIG. 1 schematizes the different approaches used to decorate bacterial OMVs with the EGFRvIII peptide. Three different strategies were used. Four strategies were designed to deliver the vIII peptide to the membrane compartment of OMVs. The rationale was that since fHbp, NHBA and OmpF are efficiently incorporated into OMVs they could serve as chaperones for the vIII peptide. To fuse the peptide to fHbp and NHBA, a DNA fragment encoding one copy (vIII) or three copies (vIIIx3) of LEEKKGNYVVTDH vIII peptide (FIG. 2, SEQ ID NO:5) was cloned at the 3' end of the full length fHbp gene, full length NHBA gene and at the 3' end of the sequence coding for fHbp lacking domains B and C (fHbpDomA), thus generating chimeric proteins carrying the vIII peptide at their C-terminus (FIG. 1A, 1B, 1E). To fuse the vIII peptide to OmpF, the DNA coding for OmpF extracellular loops was replaced with synthetic DNA coding for one or three copies of the vIII peptide (FIG. 1C). Finally, the fifth strategy was designed to deliver the vIII peptide into the lumen of OMVs. To this aim, the synthetic DNA coding for one copy of the vIII peptide was fused to the 3' end of malE, the gene coding for MBP, to create an in frame C-terminal fusion (FIG. 1D).

The detailed description of the construction of the protein chimeras and the preparation of the engineered OMVs decorated with the different protein fusions are reported below.

OMV Engineering with fHBPvIII

Construction of pET-fHbpvIII and pET-fHbpDomAvIII Plasmids

Figures 3, 3A:
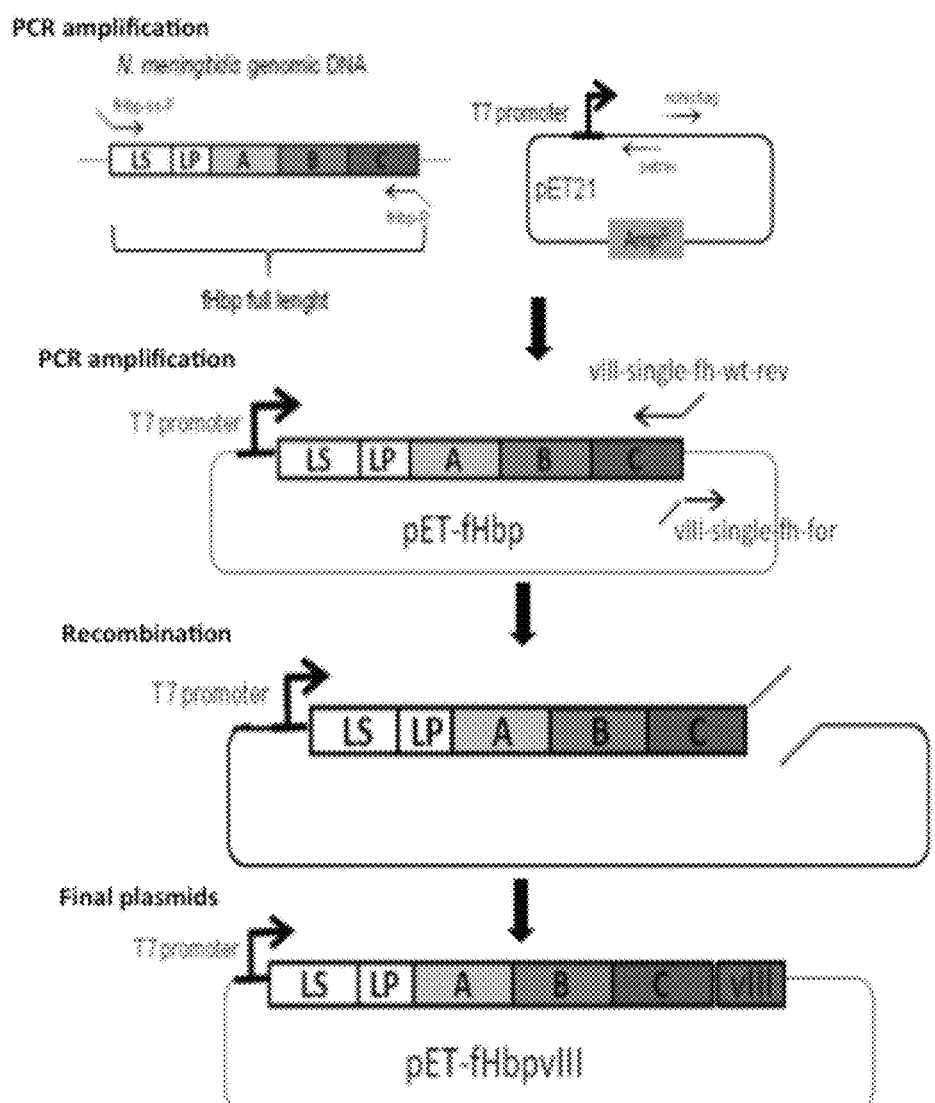
FIGS. 3A-3C. Cloning strategy used to fuse one copy of the EGRFvIII peptide to fHbp full length (FIG. 3A), fHbpDomA (FIG. 3B) and NHBA (FIG. 3C). To generate pET-fHbp, pET-fHbpDomA and pET-NHBA plasmids the sequence coding for fHbp full length, fHbpDomA or NHBA was amplified by PCR from N. meningitidis MC58 genomic DNA using primers fHbp-ss-F/fHbp R, fHbp-ss-F/fHbp A rev and NHBA-F/NHBA-R, respectively to generate extremities complementary to pET21 expression vector linear DNA, amplified with primers petrev/nohisflag (Table 1), using the polymerase incomplete primer extension (PIPE) cloning method (Klock et al, 2009). To clone one copy of the EGFRvIII peptide in translational fusion to fHbp, fHbpDomA and NHBA, pET-fHbp, pET-fHbpDomA and pET-NHBA plasmids were PCR amplified using primers vIII-single fh for /vIII-single fh-wt rev, vIII-single fh for /vIII-single fh-domA rev and NHBA_VIII_1XF/ NHBA_VIII_1X_R, respectively. Each couple of primers carries partially complementary 5' tails which, when annealed, reconstitute the nucleotide sequence coding for the EGFRvIII peptide. PCR-amplification followed by E. coli HK-100 transformation generated pET-fHbpvIII, pET-fHbpDomAvIII and pET-NHBAvIII plasmids encoding chimeric proteins carrying one copy of EGFRvIII peptide fused to the C-terminus of fHbp, fHbpDomA and NHBA, respectively. LS: leader sequence; LP: lipobox; A: fHbp domain A; B: fHbp domain B; C: fHbp domain C.
Figures 3, 3B:
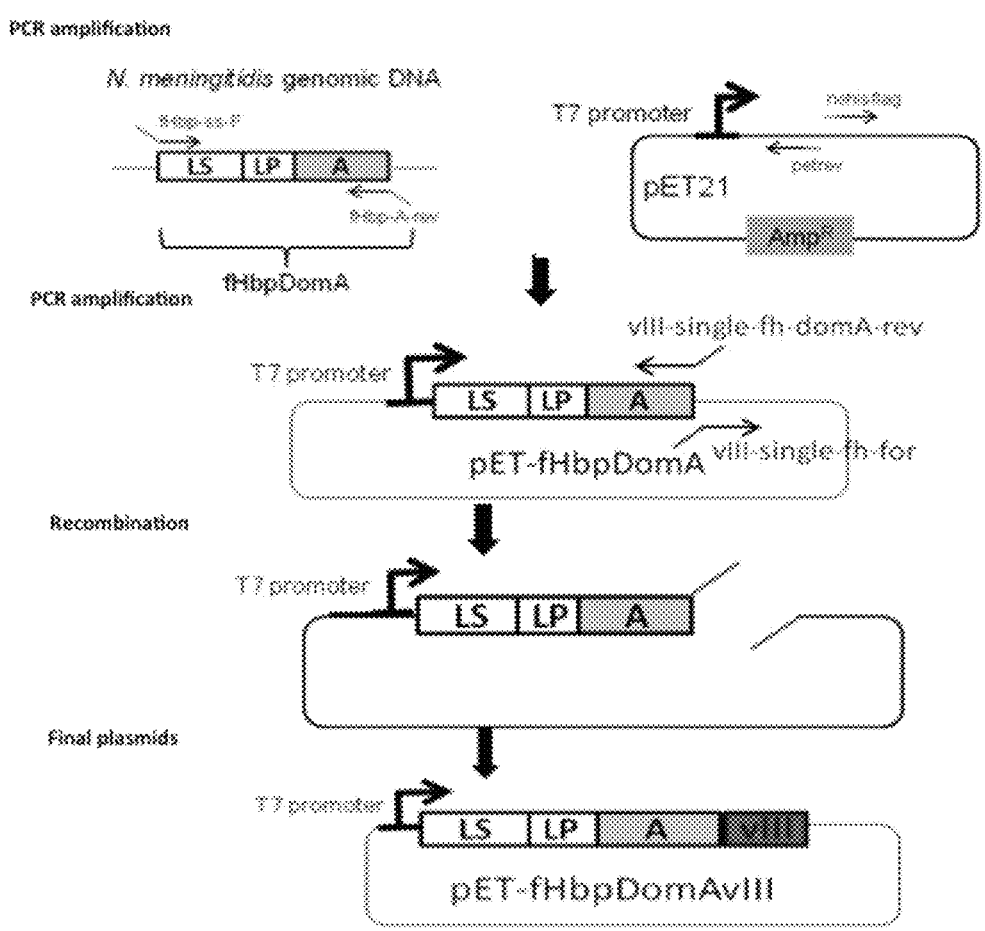

In an attempt to express and deliver the EGFRvIII peptide to the membrane compartment of E. coli OMVs the Neisseria meningitidis fHbp lipoprotein was used as a carrier. To this purpose one or three copies of the EGFRvIII peptide were fused to the 3' end of either the full length fHbp or fHbpDomA. The first step to achieve this was to amplify the sequence coding for full length fHbp (fHbpFL) and fHbpDomA and to clone the amplified sequences into pET21 plasmid. fHbpFL and fHbpDomA coding sequences (SEQ ID NOs:85 and 86) were amplified by PCR from N. meningitidis MC58 genomic DNA using primers fHbp-ss-F/fHbp R and fHbp-ss-F/fHbp A rev, respectively (Table 1 and FIG. 3), to generate extremities complementary to pET21 expression vector linear DNA, amplified with primers petrev/nohisflag (Table 1), using the polymerase incomplete primer extension (PIPE) cloning method (Klock H. E. and Lesley S. A (2009) Methods Mol. Biol. 498, 91-103). Primer fHbp-ss-F was designed to include at the 5' end of the amplified products the sequence coding for the leader peptide for secretion and the lipobox. PCR products were then mixed together and used to transform E. coli HK-100 strain, generating plasmids pET-fHbp and pET-fHbpDomA. The correctness of the cloning of fHbp and fHbpDomA was verified by sequence analysis (SEQ ID NOs:85 and 86). To clone the EGFRvIII peptide as translational fusion to the C-terminus of fHbp and fHbpDomA, the polymerase incomplete primer extension (PIPE) cloning method was used. In particular, to fuse one copy of the EGFRvIII peptide, pET-fHbp and pET-fHbpDomA plasmids were PCR amplified using primers vIII-single fh for /vIII-single fh-wt rev and vIII-single fh for /vIII-single fh-domA rev respectively (Table 1). Each couple of primers carries partially complementary 5' tails which when annealed reconstitute the nucleotide sequence coding for the EGFRvIII peptide. PCR-amplification followed by *E. coli* HK-100 transformation generated pET-fHbpvIII and pET-fHbpDomAvIII plasmids encoding chimeric proteins carrying one copy of EGFRvIII peptide fused to the C-terminus of fHbp and fHbpDomA, respectively (FIG. 3). The correctness of the cloning of fHbp-vIII and fHbpDomA-vIII fusions was verified by sequence analysis (SEQ ID NOs: 87 and 88). To fuse three copies of the EGFRvIII peptide to the C-termini of full length fHbp and fHbpDomA, the strategy schematized in FIG. 4 was used. In brief, a DNA fragment, named vIIIx3, coding for three copies of vIII separated by the GlySer dipeptide and carrying single stranded 3' protruding ends complementary to the protruding single stranded 3' ends generated by EcoRI and BamHI restriction sites was chemically synthesized (FIG. 2) and cloned in pUC plasmid cut with EcoRI and BamHI. The synthetic DNA and the linear pUC were in vitro ligated and the ligation mixture was used to transform *E. coli* HK-100, thus generating plasmid pUC-vIIIx3. Subsequently, pET-fHbp and pET-fHbpDomA plasmids were PCR amplified using primers nohisflag/fHbp R2 and nohisflag/fHbp A rev2, respectively (Table 1), while the vIIIx3 insert was PCR-amplified from pUC-vIIIx3 using primers vIII-triple fh-wt for /vIII-triple rev and vIII-triple fh-domA for /vIII-triple rev, respectively (Table 1). Finally, the PCR products were mixed together and used to transform HK-100 competent cells, obtaining plasmids pET-fHbpvIIIx3 and pET-fHbpDomAvIIIx3. The correctness of the cloning of fHbp-vIIIx3 and fHbpDomA-vIIIx3 fusions was verified by sequence analysis (SEQ ID NOs: 89 and 90).

Figure 5:
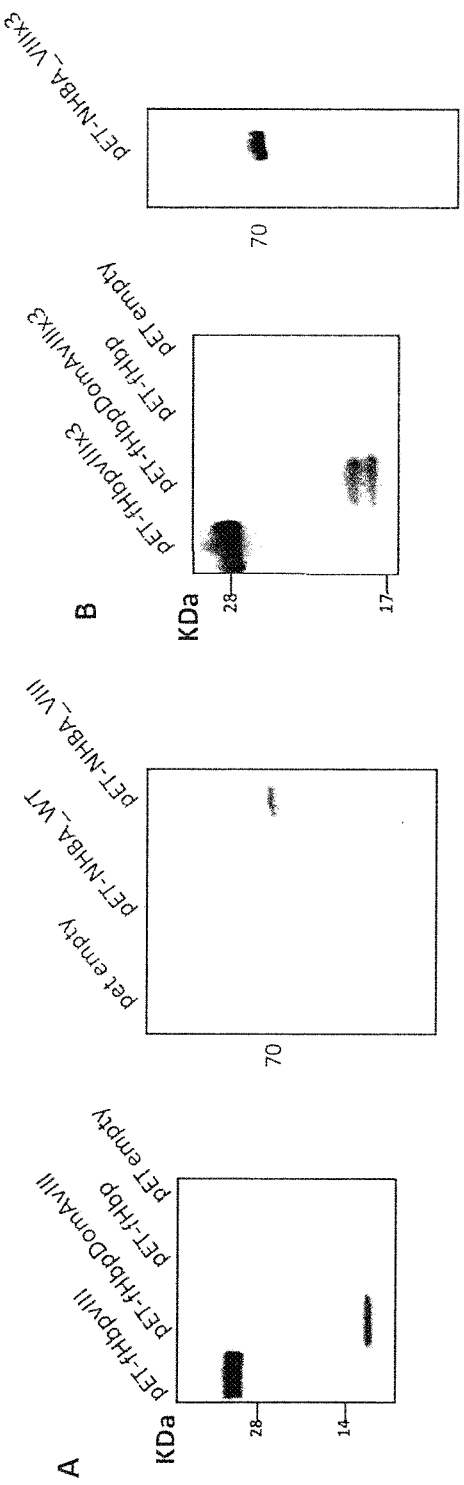
FIGS. 5A-5B. Analysis of EGFRvIII expression in total lysates of BL21(DE3)/ΔompA strain transformed with pET-fHbpvIII, pET-fHbpDomAvIII and pET-NHBAvIII. Total extracts from recombinant clones expressing fHbpvIII, fHbpDomAvIII and pET-NHBAvIII in single (A) or in triple (B) copy were separated by SDS-PAGE and analysed by Western blot. Proteins were transferred from the gel to nitrocellulose membrane and analyzed with anti-EGFRvIII rabbit polyclonal antibody. Strains transformed with pET empty vector and pET-fHbp were used as negative controls.

Expression of the fHbpvIII and fHbpDomAvIII Heterologous Proteins in *E. coli* BL21(DE3)/ΔompA Strain The four recombinant plasmids encoding fHbp and fHbpDomA fused to one copy and three copies of the EGFRvIII peptide were used to transform *E. coli* strain BL21(DE3)/ΔompA. Four recombinant strains were obtained: BL21(DE3)/ΔompA(pETfHbpFL-vIII), BL21(DE3)/ΔompA(pETfHbpFLvIIIx3), BL21(DE3)/ΔompA (pETfHbpDomAvIII) and BL21(DE3)/ΔompA (pETfHbpDomAvIIIx3). Each strain was grown in LB medium and when cultures reached an $OD_{600}$ value of 0.6, IPTG was added at 1 mM final concentration. After two additional hours of growth at 37° C., cells were collected and total protein extracts were analyzed by Western Blot. To this aim, 25 μg of total proteins from each strain were separated by SDS-PAGE and proteins were transferred to nitrocellulose filters. The filters were blocked overnight at 4° C. by agitation in blocking solution (10% skimmed milk and 0.05% TWEEN in PBS), followed by incubation for 90 minutes at 37° C. with a 1:1,000 dilution of rabbit anti-vIII polyclonal antibodies in 3% skimmed milk and 0.05% TWEEN in PBS. After 3 washing steps in PBS-TWEEN, the filters were incubated in a 1:2,000 dilution of peroxidase-conjugated anti-rabbit immunoglobulin (Dako) in 3% skimmed milk and 0.05% TWEEN in PBS for 1 hour, and after 3 washing steps, bound conjugated IgGs were detected using the Super Signal West Pico chemo-luminescent substrate (Pierce). As shown in FIG. 5A and FIG. 5B, all four fusion proteins were found expressed in the cell lysates. No immune reactive bands were detected in total lysates from *E. coli* cells carrying either pET-fHbp expressing full length fHbp or empty pET21 plasmid.

Analysis of fHbpvIII and fHbpDomAvIII Expression in OMVs

Figure 6:
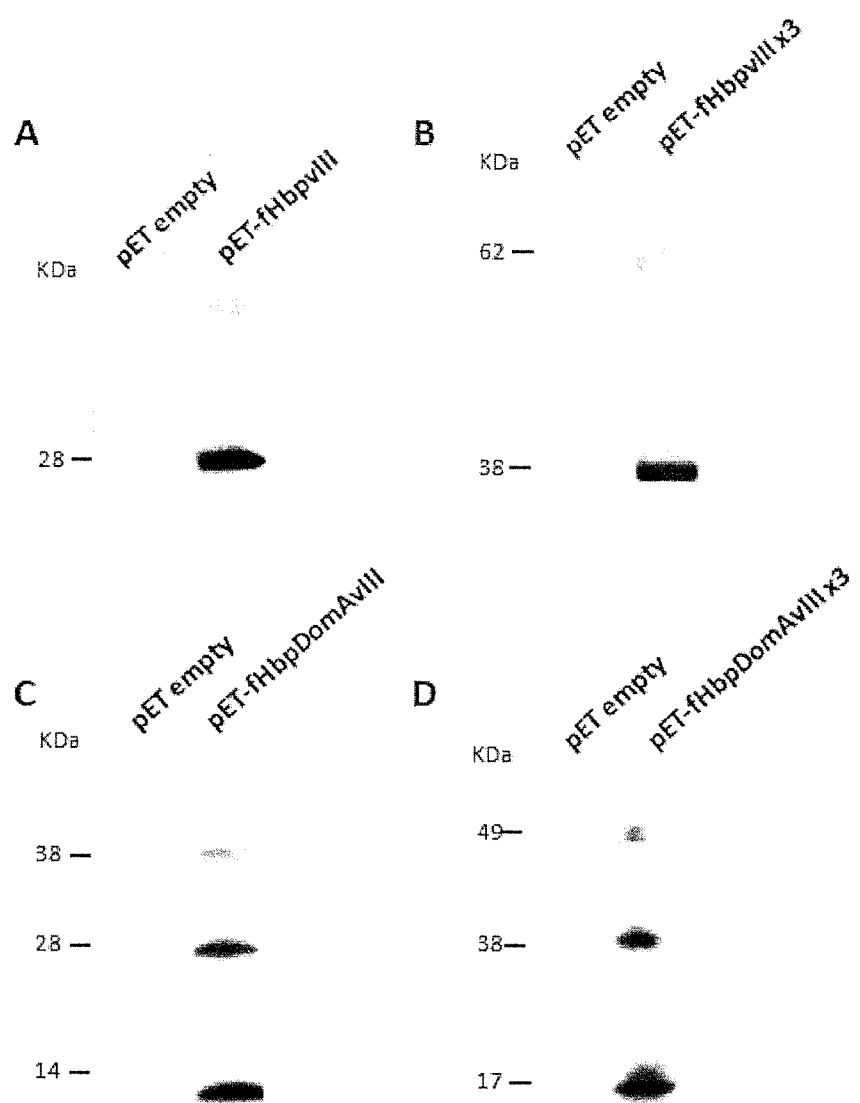
FIGS. 6A-6D. Western blot analysis of fHbpvIII and fHbpDomAvIII expression in OMVs. OMVs were purified by ultrafiltration and ultracentrifugation from the supernatants of recombinant strains transformed with pET-fHbpvIII (A), pET-fHbpvIIIx3 (B), pET-fHbpDomAvIII (C) and pET-fHbpDomAvIIIx3 (D) constructs. OMVs were collected from cultures induced with 1 mM IPTG for 2 hours. Vesicles were subjected to SDS-PAGE and Western Blot analysis using anti-EGFRvIII rabbit polyclonal antibody.

Having demonstrated that the four fusion proteins were expressed in *E. coli* BL21(DE3)/ΔompA strain, the presence of the antigens in the OMV fraction was analyzed. The four recombinant strains BL21(DE3)/ΔompA(pETfHbpFL-vIII), BL21(DE3)/ΔompA(pETfHbpFLvIIIx3), BL21(DE3)/ΔompA (pETfHbpDomAvIII) and BL21(DE3)/ΔompA (pETfHbpDomAvIIIx3) were grown in LB medium and when the cultures reached an $OD_{600}$ value of 0.6, IPTG was added at 1 mM final concentration. After two additional hours of growth at 37° C., vesicles were purified from culture supernatants by using ultrafiltration coupled to ultracentrifugation. More specifically, OMVs were collected from culture supernatants by filtration through a 0.22 μm pore size filter (Millipore) and by high-speed centrifugation (200.000×g for 2 hours). Pellets containing OMVs were finally suspended in PBS. The presence of the antigens in OMVs preparations was verified by Western Blot analysis as described in the previous section (FIG. 6). Data indicate that both fHbp and fHbpDomA carrying either one or three copies of vIII peptide were incorporated into OMVs. The presence of high molecular weight bands seem to suggest that when fused to vIII peptide fHbp and fHbpDomA can also form stable homo-oligomers which did not easily dissociate even if OMV preparations were treated at 100° C. in the presence of 1% SDS and reducing agent (FIG. 6B, C, D).

TABLE 1

Oligonucleotide primers used for generation of pET-fHbpvIII, pET-fHbpDomAvIII, pET-OmpFvIII, pET-MalEvIII, pET-NHBA-1x-vIII, pET-NHBA-3x-vIII and pET-Aa_fhbp_HIS8 constructs

| | |
|---|---|
| vIII-triple rev | GTGATGGTGATGTTATTAGCCGGAATGGTCGGTAACCAC (SEQ ID NO: 26) |
| vIII-triple fh-domA for | CCAAGTATACAAACAAGGTTCCCTGGAAGAAAAGAAGGG (SEQ ID NO: 27) |
| vIII-triple fh-wt for | CTTGCCGCCAAGCAAGGTTCCCTGGAAGAAAAGAAGGG (SEQ ID NO: 28) |
| vIII-single fh-domA rev | AACGTAGTTACCTTTTTTTTCTTCCAGTTGTTTGTATACTTGGA ACTCTCCACTCTC (SEQ ID NO: 29) |

TABLE 1-continued

Oligonucleotide primers used for generation of pET-fHbpvIII, pET-fHbpDomAvIII, pET-OmpFvIII, pET-MalEvIII, pET-NHBA-1x-vIII, pET-NHBA-3x-vIII and pET-Aa_fhbp_HIS8 constructs

| | |
|---|---|
| vIII-single fh-wt rev | TTAAACGTAGTTACCTTTTTTTTCTTCCAGTTGCTTGGCGGCAAGGC (SEQ ID NO: 30) |
| vIII-single fh for | AAAGGTAACTACGTTGTTACCGACCACTAACATCACCATCACCATCACGATTACAAAGA (SEQ ID NO: 31) |
| fHbpA rev | GTGATGGTGATGTTATTGTTTGTATACTTGGAACTCTCCACTCTC (SEQ ID NO: 32) |
| fHbp-R | GTGATGGTGATGTTATTATTGCTTGGCGGCAAGGC (SEQ ID NO: 33) |
| fHbp-R2 | TTATTGCTTGGCGGCAAGGC (SEQ ID NO: 34) |
| fHbpA rev2 | TTGTTTGTATACTTGGAACTCTCCACTCTC (SEQ ID NO: 35) |
| fHbp-SS-F | GGAGATATACATATGGTGAATCGAACTGCCTTCTGCTGCC (SEQ ID NO: 36) |
| petrev | CATATGTATATCTCCTTCTTAAAGTTAAAC (SEQ ID NO: 37) |
| nohisflag | TAACATCACCATCACCATCACGATTACAAAGA (SEQ ID NO: 38) |
| NdI-MalEf | ggaattccatatgAAAATAAAAACAGGTGCACGCATC (SEQ ID NO: 39) |
| R1-MalEr | ccttttttttcttccagCTTGGTGATACGAGTCTGCG (SEQ ID NO: 40) |
| R2-MalEr | taacaacgtagttaCCTTTTTTTTCTTCCAGCTTGGTGA (SEQ ID NO: 41) |
| XhI-R3-MalEr | ccccgctcgagttagtggtcggTAACAACGTAGTTACCTTTTTTTTCTTCC (SEQ ID NO: 42) |
| pET21-MalEf | ggagatatacatatgAAAATAAAAACAGGTGCACGCATC (SEQ ID NO: 43) |
| pET21-R3-MalEr | gtgatggtgatgttagtggtcggTAACAACGTAGTTACCTTTTTTTTCTTCC (SEQ ID NO: 44) |
| NdI-OmpFf | ggaattccatatgATGAAGCGCAATATTCTGGC (SEQ ID NO: 45) |
| XM-OmpFr | ccccgctcgagTTAGAACTGGTAAACGATACCCAC (SEQ ID NO: 46) |
| pET21OmpFf | ggagatatacatatgATGAAGCGCAATATTCTGGC (SEQ ID NO: 47) |
| pET21OmpFr | gtgatggtgatgttaGAACTGGTAAACGATACCCAC (SEQ ID NO: 48) |
| Loop1Vf | aaaggtaactacgttgttaccgaccacGGCGACATGACCTATGCCC (SEQ ID NO: 49) |
| Loop1Vr | aacgtagttaccttttttttcttccagAAAATAATGCAGACCAACAGCTTTACCG (SEQ ID NO: 50) |
| Loop2Vf | aaaggtaactacgttgttaccgaccacGGTAACAAAACGCGTCTGGC (SEQ ID NO: 51) |
| Loop2Vr | aacgtagttaccttttttttcttccagGTTACCCTGGAAGTTATATTCCCAC (SEQ ID NO: 52) |
| Loop4Vf | aaaggtaactacgttgttaccgaccacAACGGCGACGGTGTTGGC (SEQ ID NO: 53) |

TABLE 1-continued

Oligonucleotide primers used for generation of pET-fHbpvIII, pET-fHbpDomAvIII, pET-OmpFvIII, pET-MalEvIII, pET-NHBA-1x-vIII, pET-NHBA-3x-vIII and pET-Aa_fhbp_HIS8 constructs

| Name | Sequence |
|---|---|
| Loop4Vr | aacgtagttaccttttttttcttccagGTTTTTACCCAGGTACTGAACAGC (SEQ ID NO: 54) |
| Loop6Vf | aaaggtaactacgttgttaccgaccacGCCAACAAAACGCAAGACGTTCTG (SEQ ID NO: 55) |
| Loop6Vr | aacgtagttaccttttttttcttccagCGTAGCGTTACGGGTTTCACC (SEQ ID NO: 56) |
| Loop7Vf | aaaggtaactacgttgttaccgaccacGTGAACTACTTTGAAGTGGGCG (SEQ ID NO: 57) |
| Loop7Vr | aacgtagttaccttttttttcttccagTTTCGCTTTAGATTTGGTGTAAGCGAT (SEQ ID NO: 58) |
| Loop8Vf | aaaggtaactacgttgttaccgaccacACCGTTGCTGTGGGTATCGTT (SEQ ID NO: 59) |
| Loop8Vr | aacgtagttaccttttttttcttccagCTGGTTGATGATGTAGTCAACATAGG (SEQ ID NO: 60) |
| L1_3x_If | GGTCTGCATTATTTTGGTTCCCTGGAAGAAAAGAAGGG (SEQ ID NO: 61) |
| L1_3x_Ir | GGTCATGTCGCCGCCGGAATGGTCGGTAACCAC (SEQ ID NO: 62) |
| L4_3x_If | GGGTAAAAACGGTTCCCTGGAAGAAAAGAAGGG (SEQ ID NO: 63) |
| L4_3x_Ir | CCGTCGCCGTTGCCGGAATGGTCGGTAACCAC (SEQ ID NO: 64) |
| L1_3x_Vf | GGCGACATGACCTATGCCCG (SEQ ID NO: 65) |
| L1_3x_Vr | AAAATAATGCAGACCAACAGCTTTACCG (SEQ ID NO: 66) |
| L4_3x_Vf | AACGGCGACGGTGTTGGCGG (SEQ ID NO: 67) |
| L4_3x_Vr | GTTTTTACCCAGGTACTGAACAGC (SEQ ID NO: 68) |
| NHBA-F | GGAGATATACATATGTTTAAACGCAGCGTAATC (SEQ ID NO: 128) |
| NHBA-R | GTGATGGTGATGTTATCAATCCTGCTCTTTTTTG (SEQ ID NO: 129) |
| NHBA_VIII_1X R | aacgtagttaccttttttttcttccagATCCTGCTCTTTTTTGCCGG (SEQ ID NO: 130) |
| NHBA_VIII_1X F | Aaaggtaactacgttgttaccgaccac TAA CAT CAC CAT CAC CAT CAC GAT TAC AAA GA (SEQ ID NO: 117) |
| NHBA-VIII-3X-i-F | CCGGCAAAAAAGAGCAGGAT ggttccctggaagaaaagaaggg (SEQ ID NO: 118) |
| NHBA-VIII-3X-i-R | GTGATGGTGATGTTA gccggaatggtcggtaaccac (SEQ ID NO: 119) |
| NHBA-VIII-3x v-R | ATCCTGCTCTTTTTTGCCGG (SEQ ID NO: 120) |
| NHBA-VIII-3x-v-f | TAACATCACCATCACCATCACGATTACAAAGA (SEQ ID NO: 121) |
| Ag_fHbp-F | Gaaggagatatacat ATG GTT TAC CCT GTT ATA ACG (SEQ ID NO: 122) |
| Ag_fHbp-R | ATGGTGATGGTGATGTTCTTT TTTACCTGCCAAACC (SEQ ID NO: 123) |

TABLE 1-continued

Oligonucleotide primers used for generation of pET-fHbpvIII, pET-fHbpDomAvIII, pET-OmpFvIII, pET-MalEvIII, pET-NHBA-1x-vIII, pET-NHBA-3x-vIII and pET-Aa_fhbp_HIS8 constructs

| | |
|---|---|
| pET 2-R | CATATGTATATCTCCTTCTTAAAGTTAAACaaaattatttc (SEQ ID NO: 124) |
| pET HIS-F | catcaccatcaccatcacTAAGATTACAAAGACGATGATGACAAGtga (SEQ ID NO: 125) |

Figure 7:
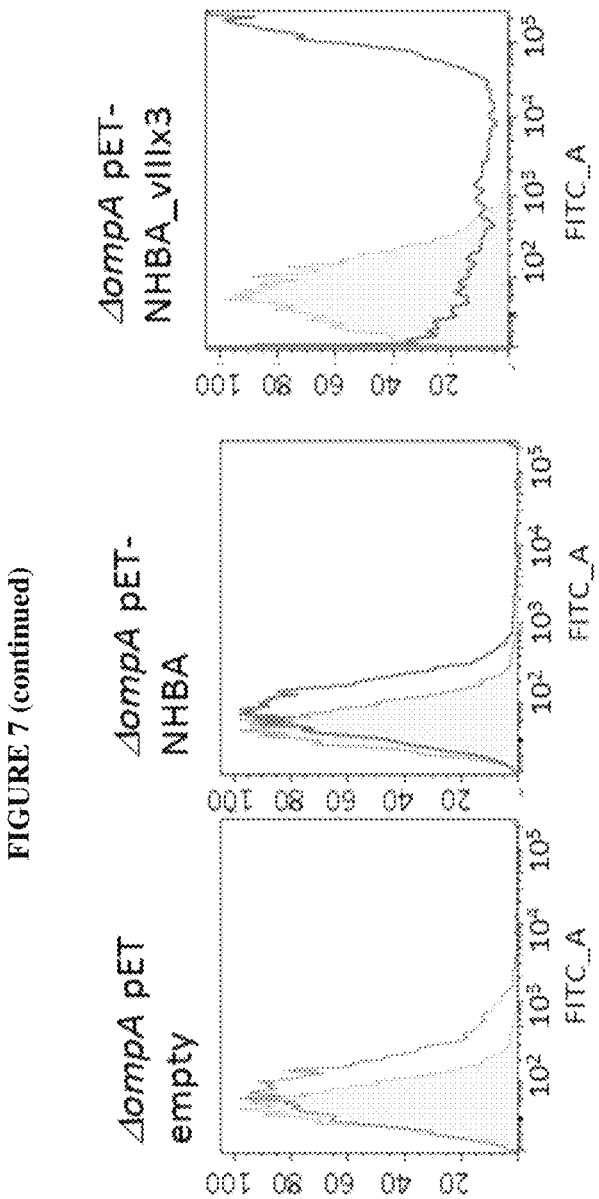
FIGS. 7A-7B. Analysis of surface exposition of EGFRvIII in fHbpvIII, fHbpvIIIx3 (A), NHBAvIII and NHBAvIIIx3 (B) recombinant strains, evaluated by Fluorescence Activating Cell Sorting. EGFRvIII surface expression was evaluated on bacterial cells after 2 h induction with 1 mM IPTG. Cells were stained with anti-vIII polyclonal antibody followed by anti-rabbit-FITC secondary antibody. BL21(DE3)/ΔompA strain caning pET21 empty plasmid was used as a negative control.

Analysis of cellular localization of fHbpvIII and fHbpvIIIx3 The localization of recombinant fHbpvIII and fHbpvIIIx3 fusion proteins was evaluated by flow cytometry. To this aim, recombinant E. coli strains BL21 (DE3)/ΔompA (pETfHbpFL-vIII), BL21 (DE3)/ΔompA (pETfHbpFLvIIIx3) and E. coli BL21(DE3)/ΔompA (pET21), as negative control, were grown at 37° C. under agitation. When cultures reached an $OD_{600}$ value of 0.6, IPTG was added at a final concentration of 1 mM and bacteria were grown for 2 additional hours. Subsequently, bacteria cells corresponding to those contained in 1 ml culture at $OD_{600}$=1 were collected by centrifugation at 13,000×g for 5 minutes and pellets were re-suspended in 50 ml of PBS containing 1% BSA. 50 µl of cell suspensions were incubated with 50 µl of an appropriate dilution of anti-vIII rabbit polyclonal antibodies raised against the vIII peptide conjugated to Keyhole Limpet Hemocyanin (KLH) or with 50 µl of PBS containing 1% BSA as negative control. After 1 hour, 100 µl of PBS containing 1% BSA were added and the suspensions were centrifuged at 3,000×g for 10 minutes and supernatants discarded. Pellets were washed with 200 µl of PBS containing 1% BSA and bacteria subsequently incubated for 30 minutes on ice with goat anti-rabbit antibodies (Alexa flour488, Life Technology) added at a final dilution of 1:2,000. Finally, After 2 wash steps, pellets were re-suspended in 200 µl of PBS and analyzed with FACS CANTOII evaluating collected data with FlowJo software. As shown in FIG. 7A, in the presence of anti-vIII antibodies, a clear shift in fluorescence intensity was observed in a substantial fraction of bacterial cells expressing both fHbpvIII and fHbpvIIIx3. No difference in fluorescence intensity was observed when E. coli BL21 (DE3)/ΔompA were incubated with anti-vIII antibodies. These data indicate not only that fHbvIII and fHbpvIIIx3 were expressed in E. coli BL21(DE3)/ΔompA and localized in OMVs, but also that the fused proteins associated to the outer membrane, with their C-terminal portion carrying the vIII peptide exposed to the extracellular compartment.

Engineered OMVs Carrying Recombinant fHbpvIII and fHbpDomAvIII Fusion Proteins Induce High Antibodies Titers in Immunized Mice To test whether OMVs purified from fHbpvIIIx3 and fHbpDomAvIIIx3 recombinant strains were capable of inducing vIII-specific antibody responses, CD1 mice were i.p. immunized three times at two-week intervals with 10 µg of OMVs formulated in Alum. Blood samples were collected nine days after second dose (post2) and seven days after third dose (post3) administration and anti-vIII IgGs were detected by using plates coated in each well with 0.5 µg of synthetic vIII peptide conjugated to Keyhole limpet hemocyanin (vIII-KHL). Serum deriving from mice immunized with empty OMVs was used as negative control. More specifically, coating was carried out by incubating plates overnight at 4° C. with 100 µl of conjugated peptide (5 µg/ml). Subsequently, wells were washed three times with PBST (0.05% TWEEN 20 in PBS, pH 7.4), incubated with 100 µl of 1% BSA in PBS for 1 h at room temperature and washed again three times with PBST. Serial dilutions of serum samples in PBST containing 1% BSA were added to the plates, incubated 2 h at 37° C., and washed three times with PBST. Then 100 µl/well of 1:2.000 diluted, alkaline phosphatase-conjugated goat anti-mouse IgGs were added and left for 2 h at 37° C. After triple PBST wash, bound alkaline phosphatase-conjugated antibodies were detected by adding 100 µl/well of 3 mg/ml para-nitrophenyl-phosphate disodium hexahydrate (Sigma-Aldrich) in 1M diethanolamine buffer (pH 9.8). After 10 minute incubation at room temperature, the reaction was stopped with 100 µl 7% EDTA and substrate hydrolysis was analyzed at 405 nm in a microplate spectrophotometer.

Figure 8:
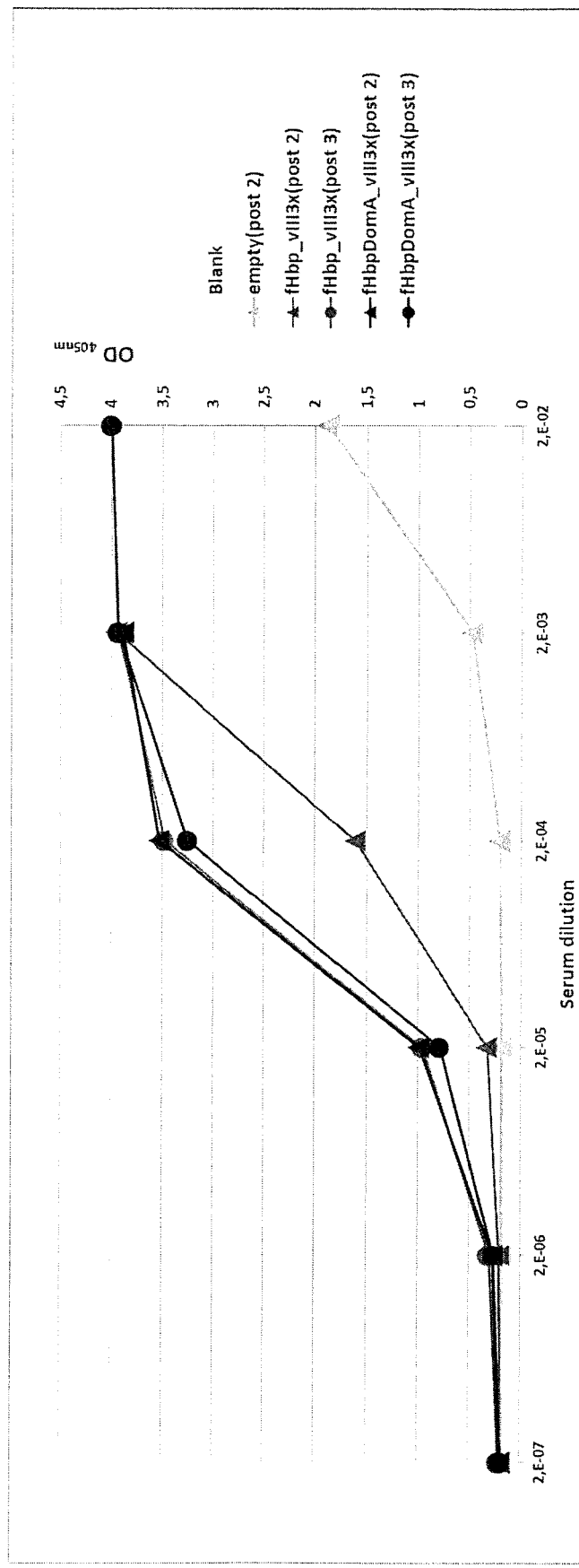
FIG. 8. Analysis of vIII-specific IgG induced in mice immunized with fHbpvIIIx3 and fHbpDomAvIIIx3 OMVs. Antigen-specific IgG were measured by ELISA in sera from mice immunized with two (post2) or three (post3) doses of OMVs. As a control, antibody titers from mice immunized with "empty" OMVs were tested. Anti-mouse IgGs conjugated to alkaline phosphatase were used as secondary antibody. OD405 was measured for each serum dilution.

As shown in FIG. 8, OMVs carrying fHbpvIIIx3 and fHbpDomAvIIIx3 fusion proteins were able to induce high anti-vIII IgG titers in mice. In particular, OMV carrying fHbpDomA3xvIII induced maximum antibody responses even after only two immunizations.

OMV Engineering with NHBAvIII

Construction of pET-NHBAvIII Plasmids

Figures 3, 3C:
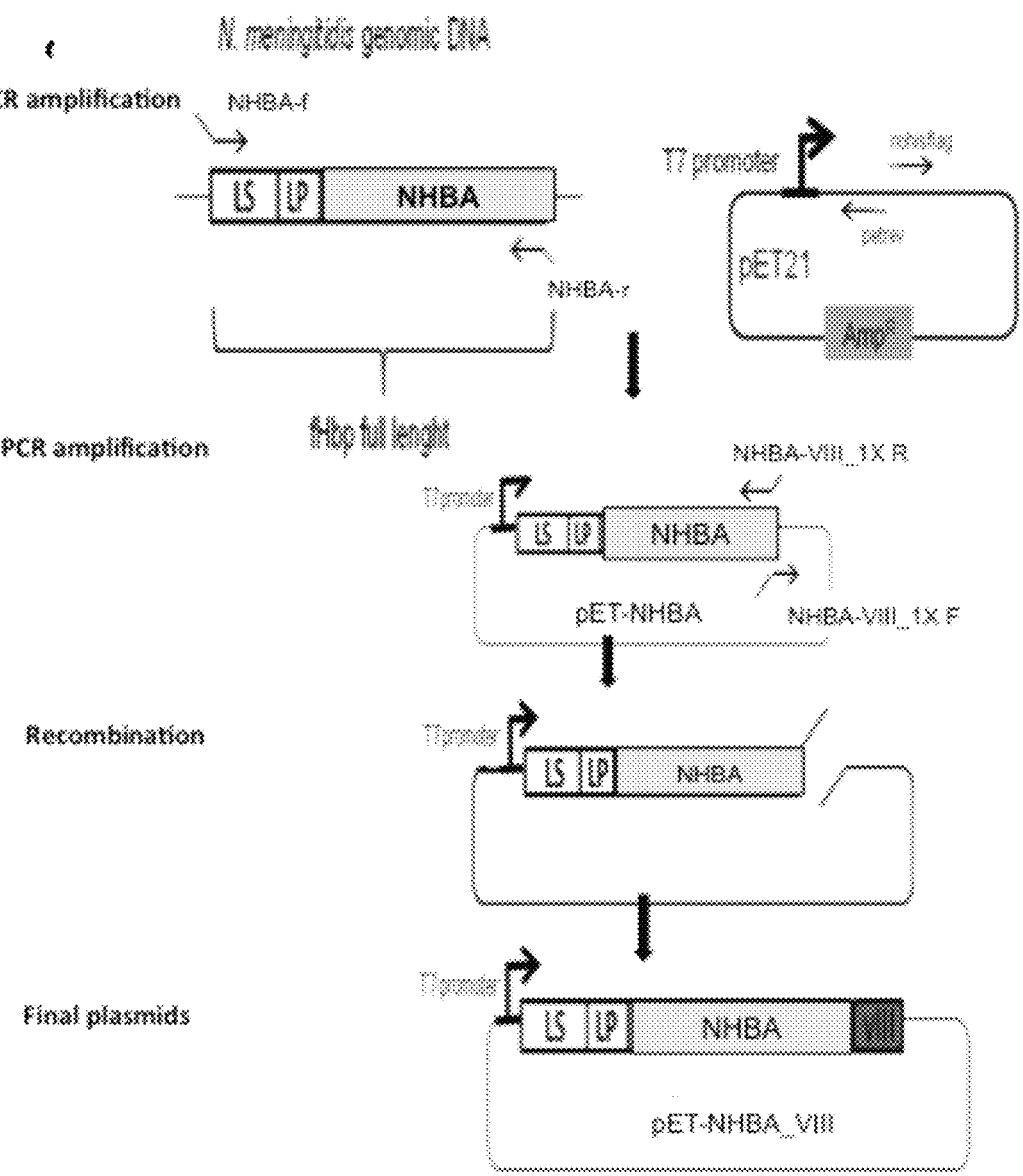
Figures 4, 4A:
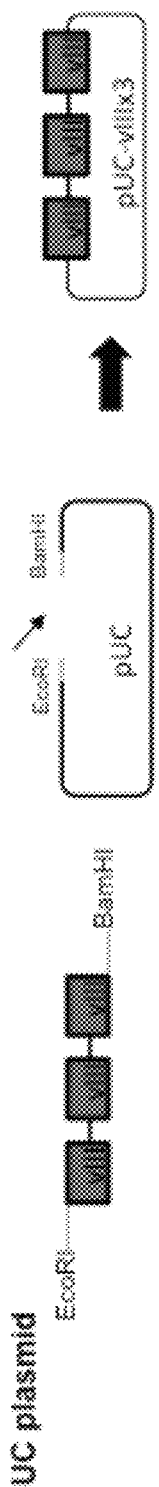
FIGS. 4A-4D. Cloning strategy to fuse three copies of the EGRFvIII peptide to fHbp full length, fHbpDomA and NHBA.
Figures 4, 4B:
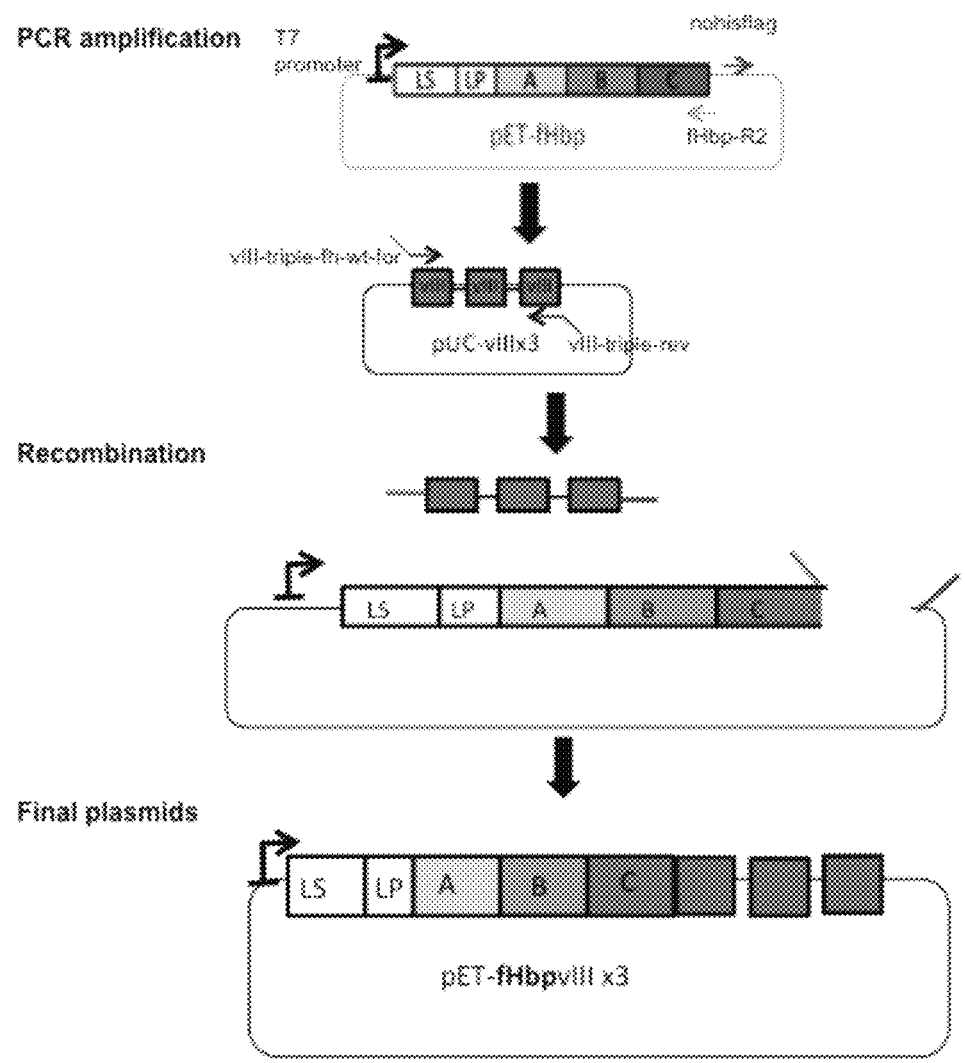
Figures 4, 4C:
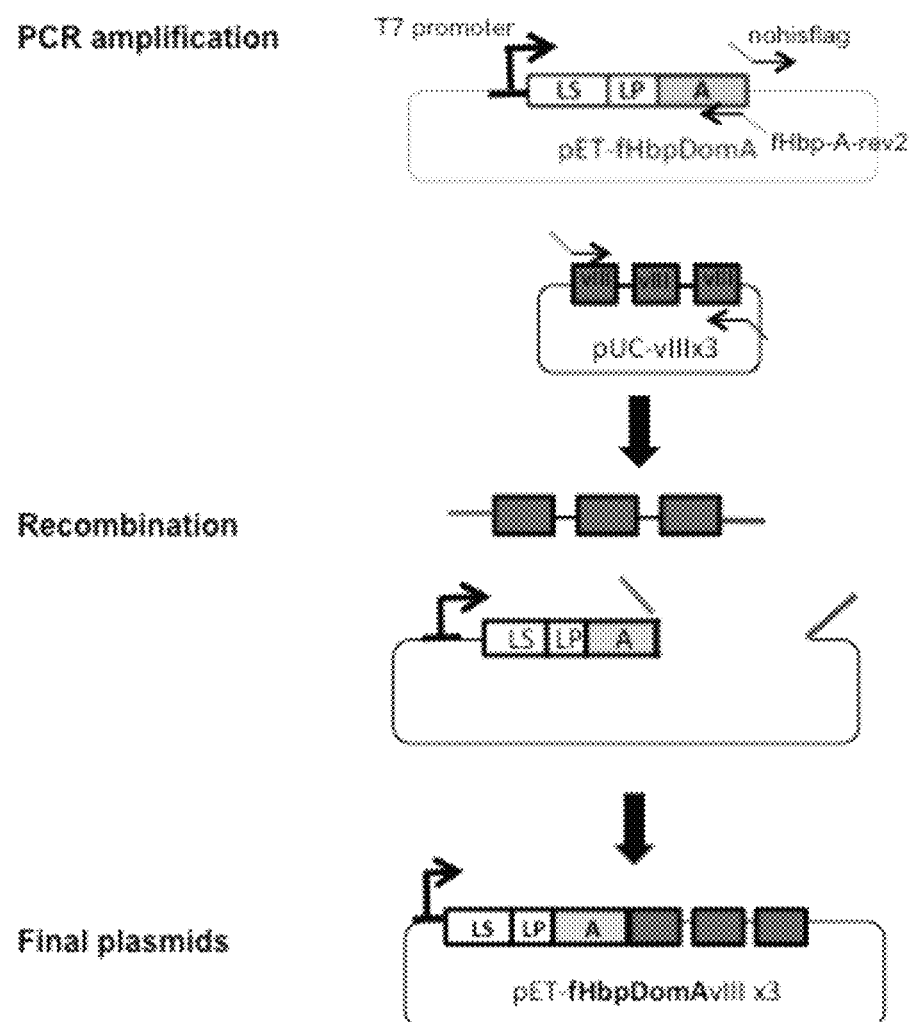
Figures 4, 4D:
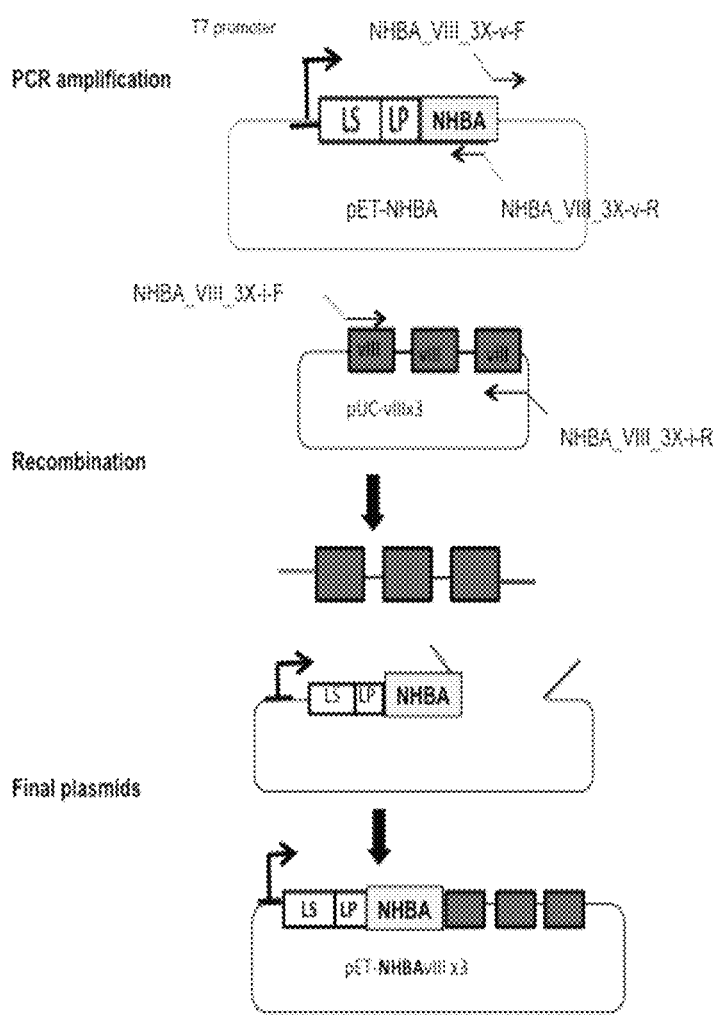

In order to express and deliver the EGFRvIII peptide to the membrane compartment of E. coli OMVs the Neisseria meningitidis NHBA lipoprotein was used as a carrier. To this purpose one or three copies of the EGFRvIII peptide were fused to the 3' end of the full length NHBA. The first step to achieve this was to amplify the sequence coding for full length NHBA and to clone the amplified sequences into pET21 plasmid. NHBA coding sequences (SEQ ID NO:113) were amplified by PCR from N. meningitidis MC58 genomic DNA using primers NHBA-F/NHBA-R (Table 1 and FIG. 3C), to generate extremities complementary to pET21 expression vector linear DNA, amplified with primers petrev/nohisflag (Table 1), using the polymerase incomplete primer extension (PIPE) cloning method (Klock H. E. and Lesley S. A (2009) Methods Mol. Biol. 498, 91-103). Primer NHBA-F was designed to include at the 5' end of the amplified products the sequence coding for the leader peptide for secretion and the lipobox. PCR products were then mixed together and used to transform E. coli HK-100 strain, generating plasmids pET-NHBA. The correctness of the cloning of NHBA was verified by sequence analysis (SEQ ID NO:113). To clone the EGFRvIII peptide as translational fusion to the C-terminus of NHBA the polymerase incomplete primer extension (PIPE) cloning method was used. In particular, to fuse one copy of the EGFRvIII peptide, pET-NHBA plasmid was PCR amplified using primers NHBA_VIII_1XF/NHBA_VIII_1X_R (Table 1). These primers carries partially complementary 5' tails which when annealed reconstitute the nucleotide sequence coding for the EGFRvIII peptide. PCR-amplification followed by E. coli HK-100 transformation generated pET-NHBAvIII plasmid encoding chimeric proteins carrying one copy of EGFRvIII peptide fused to the C-terminus of NHBA (FIG. 3C). The correctness of the cloning of NHBA-vIII fusion was verified by sequence analysis (SEQ ID NO:114). To fuse three copies of the EGFRvIII peptide to the C-termini of full length NHBA, was used the strategy schematized in FIG. 4. In brief, a DNA fragment, named vIIIx3, coding for three copies of vIII separated by the GlySer dipeptide and carrying single stranded 3' protruding ends complementary to the protruding single stranded 3' ends generated by EcoRI and BamHI restriction sites was chemically synthesized and cloned in pUC plasmid cut with EcoRI and BamHI. The synthetic DNA and the linear pUC were in vitro ligated and the ligation mixture was used to transform E. coli HK-100, thus generating plasmid pUC-vIIIx3 (FIG. 4A). Subsequently, pET-NHBA plasmid was PCR amplified using primers NHBA-vIII-3x-v-f/NHBA-vIII-3x-v-r (Table 1), while the vIIIx3 insert was PCR-amplified from pUC-vIIIx3 using primers NHBA-vIII-3x-i-f/NHBA-vIII-3x-i-r (Table 1). Finally, the PCR products were mixed together and used to transform HK-100 competent cells, obtaining plasmids pET-NHBAvIIIx3 FIG. 4D). The correctness of the cloning of NHBA-vIIIx3 fusion was verified by sequence analysis (SEQ ID NO:115).

Expression of the NHBAvIII Heterologous Protein in E. coli BL21(DE3)/ΔompA Strain The two recombinant plasmids encoding NHBA fused to one copy and three copies of the EGFRvIII peptide were used to transform E. coli strain BL21(DE3)/ΔompA. Two recombinant strains were obtained: BL21(DE3)/ΔompA (pET-NHBA-vIII) and BL21(DE3)/ΔompA(pET-NHBAvIIIx3). Each strain was grown in LB medium and when cultures reached an $OD_{600}$ value of 0.6, IPTG was added at 1 mM final concentration. After two additional hours of growth at 37° C., cells were collected and total protein extracts were analyzed by Western Blot. To this aim, 25 µg of total proteins from each strain were separated by SDS-PAGE and proteins were transferred to nitrocellulose filters. The filters were blocked overnight at 4° C. by agitation in blocking solution (10% skimmed milk and 0.05% TWEEN in PBS), followed by incubation for 90 minutes at 37° C. with a 1:1,000 dilution of rabbit anti-vIII polyclonal antibodies in 3% skimmed milk and 0.05% TWEEN in PBS. After 3 washing steps in PBS-TWEEN, the filters were incubated in a 1:2,000 dilution of peroxidase-conjugated anti-rabbit immunoglobulin (Dako) in 3% skimmed milk and 0.05% TWEEN in PBS for 1 hour, and after 3 washing steps, bound conjugated IgGs were detected using the Super Signal West Pico chemo-luminescent substrate (Pierce). As shown in FIG. 5A and FIG. 5B, both fusion proteins were found expressed in the cell lysates. No immune reactive bands were detected in total lysates from E. coli cells carrying either pET-NHBA expressing full length NHBA or empty pET21 plasmid.

Analysis of Cellular Localization of NHBAvIII and NHBAvIIIx3

The localization of recombinant NHBAvIII and NHBAvIIIx3 fusion proteins was evaluated by flow cytometry. To this aim, recombinant E. coli strains BL21 (DE3)/ΔompA (pET-NHBAvIII), BL21 (DE3)/ΔompA (pET-NHBAvIIIx3) and E. coli BL21(DE3)/ΔompA(pET21), as negative control, were grown at 37° C. under agitation. When cultures reached an $OD_{600}$ value of 0.6, IPTG was added at a final concentration of 1 mM and bacteria were grown for 2 additional hours. Subsequently, bacteria cells corresponding to those contained in 1 ml culture at $OD_{600}=1$ were collected by centrifugation at 13,000×g for 5 minutes and pellets were re-suspended in 50 ml of PBS containing 1% BSA. 50 µl of cell suspensions were incubated with 50 µl of an appropriate dilution of anti-vIII rabbit polyclonal antibodies raised against the vIII peptide conjugated to Keyhole Limpet Hemocyanin (KLH) or with 50 µl of PBS containing 1% BSA as negative control. After 1 hour, 100 µl of PBS containing 1% BSA were added and the suspensions were centrifuged at 3,000×g for 10 minutes and supernatants discarded. Pellets were washed with 200 µl of PBS containing 1% BSA and bacteria subsequently incubated for 30 minutes on ice with goat anti-rabbit antibodies (Alexa flour488, Life Technology) added at a final dilution of 1:2,000. Finally, After 2 wash steps, pellets were re-suspended in 200 µl of PBS and analyzed with FACS CANTOII evaluating collected data with FlowJo software. As shown in FIG. 7B, in the presence of anti-vIII antibodies, a clear shift in fluorescence intensity was observed in a substantial fraction of bacterial cells expressing both NHBAvIII and NHBAvIIIx3. No difference in fluorescence intensity was observed when E. coli BL21(DE3)/ΔompA were incubated with anti-vIII antibodies. These data indicate not only that NHBAvIII and NHBAvIIIx3 were expressed in E. coli BL21(DE3)/ΔompA and that the fused proteins are associated to the outer membrane with their C-terminal portion carrying the vIII peptide exposed to the extracellular compartment.

OMV Engineering with OmpFvIII

Construction of pET-OmpFvIII Plasmids

With the aim of expressing EGFRvIII peptide on the OMVs surface, the fusion of vIII peptide to Outer Membrane Protein F (OmpF) was attempted. OmpF is a protein embedded in the outer membrane with eight loops (L) exposed to the extracellular compartment (FIG. 1C). Therefore, if extracellular loops are removed and replaced with vIII peptide, the peptide should theoretically be delivered to the membrane surface. To test this hypothesis, the coding sequence of the extracellular loops L1, L2, L4, L6, L7, L8 was substituted with the nucleotide sequence coding for the 13 amino acid EGFRvIII peptide (FIG. 2A), thus generating six constructs, each construct having one loop substituted. The first step to obtain the six engineered OmpF constructs was to clone the OmpF gene into pET21 plasmid. To this aim, the entire OmpF coding sequence was amplified from E. coli K12-MG1655 genomic DNA using primers NdI-OmpFf/XhI-OmpFr (Table 1). Then, the resulting fragment was re-amplified with primers pET21 OmpFf/pET21 OmpFr (Table 1) to make the extremities complementary to pET21 expression vector which was amplified with primers petrev/nohisflag (Table 1), using the polymerase incomplete primer extension (PIPE) method. The two linear DNAs were mixed together and used to transform the highly competent E. coli strain HK-100, to obtain the pET-OmpF plasmid. The correctness of the cloning of the ompF gene in pET21 was verified by sequence analysis (SEQ ID NO:91).

To substitute loops L1, L2, L4, L6, L7 and L8 with EGFRvIII, the polymerase incomplete primer extension (PIPE) cloning method was used. pET-OmpF was amplified by PCR using the primer couples Loop1Vf/Loop1Vr, Loop2Vf/Loop2Vr, Loop4Vf/Loop4Vr, Loop6Vf/Loop6Vr, Loop7Vf/Loop7Vr and Loop8Vf/Loop8Vr, respectively (Table 1). Each couple was designed to anneal to the flanking regions of a selected loop and to carry complementary tails that when annealed reconstituted the sequence coding for vIII peptide. PCR-amplification followed by E. coli HK100 transformation resulted in replacement of the loop with the DNA sequence coding for EGFRvIII. Plasmids pET-OmpFvIII_L1, pET-OmpFvIII_L2, pET-OmpFvIII_L4, pET-OmpFvIII_L6, pET-OmpFvIII_L7 and pET-OmpFvIII_L8 were obtained. The correctness of the replacement of each loop coding sequence with the small fragment coding for the vIII peptide was verified by sequence analysis (SEQ ID NOs:92, 94, 95, 97, 98 and 99).

In an attempt to maximize the exposure of the peptide to the extracellular milieu two other constructs were generated, in which L1 or L4 were substituted with three copies of EGFRvIII (FIG. 2B). To obtain pET-OmpFvIIIx3_L1, the vIIIx3 coding sequence was amplified from pUC-vIIIx3 (see previous section) using primers L1_3x_If/L1_3x_Ir (Table 1). The primers carried 5' ends complementary to the sequences preceding and following the region coding for L1. In parallel, pET-OmpF plasmid was amplified using primers L1_3x_Vf/L1_3x_Vr. The two DNA fragments were mixed together and used to transform E. coli HK-100 competent cells, thus obtaining a clone carrying plasmid pET-OmpFvIIIx3_L1. A similar strategy was used to obtain pET-OmpFvIIIx3_L4 plasmid. The vIIIx3 coding sequence was amplified from pUC-vIIIx3 (see previous section) using primers L4_3x_If/L4_3x_Ir (Table 1). The primers carried 5' ends complementary to the sequences preceding and following the region coding for L4. In parallel, pET-OmpF plasmid was amplified using primers L4_3x_Vf/L4_3x_Vr (Table 1). The two DNA fragments were mixed together and used to transform E. coli HK-100 competent cells, thus obtaining a clone carrying plasmid pET-OmpFvIIIx3_L4. The correctness of the replacement of Loop 1 and Loop4 with the small fragment coding for three copies of the vIII peptide was verified by sequence analysis (SEQ ID NOs: 93 and 96).

Figure 9:
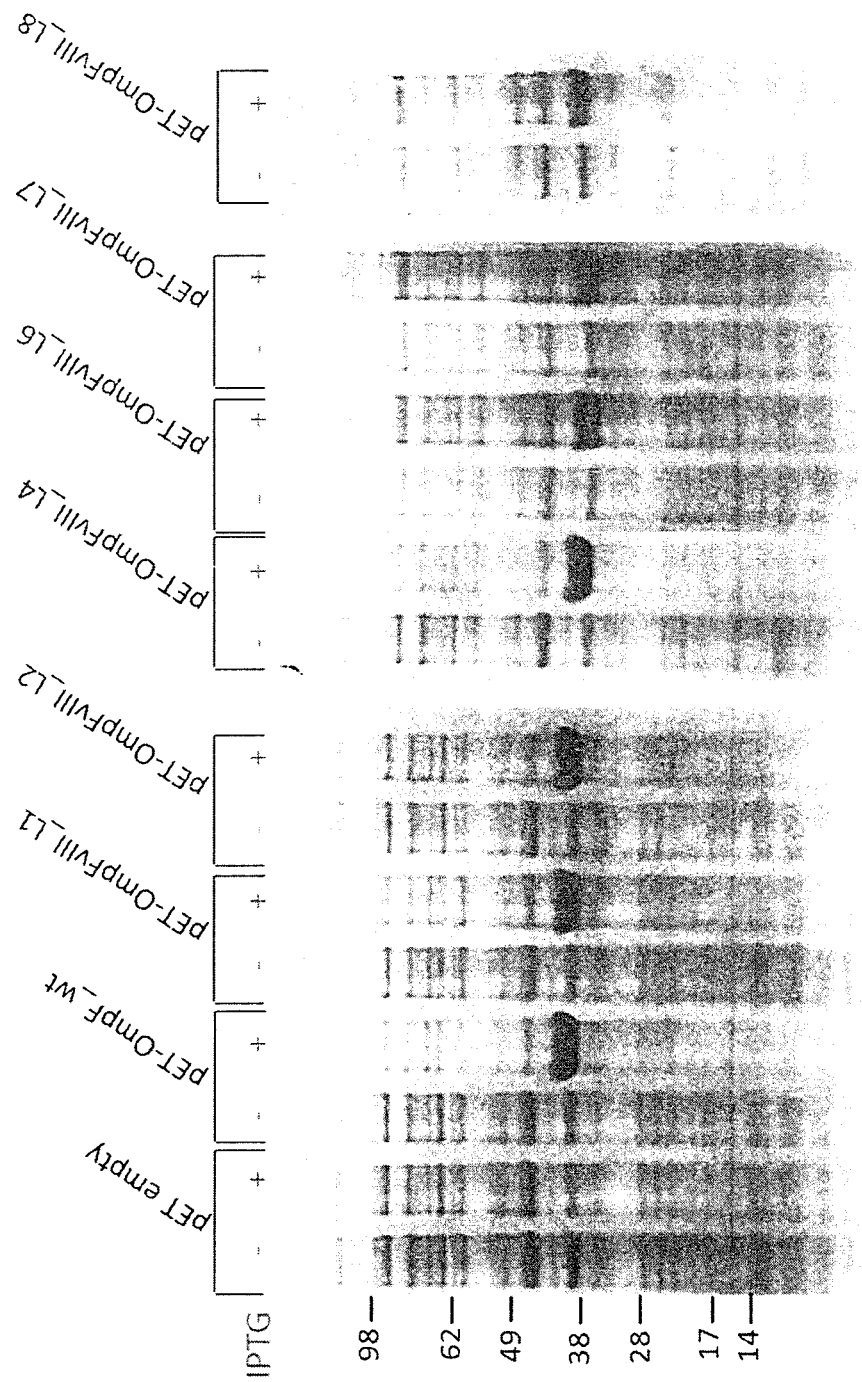
FIG. 9. Analysis of antigen expression in total lysates of BL21(DE3)/ΔompA strain transformed with pET-OmpFvIII constructs. Total extracts from recombinant clones expressing OmpFvIII were separated by SDS-PAGE and analyzed by COOMASSIE blue staining. Protein expression was induced by addition of 1 mM IPTG to the culture supernatants and extracts were prepared by collecting bacteria after 3 h induction.
Figure 10:
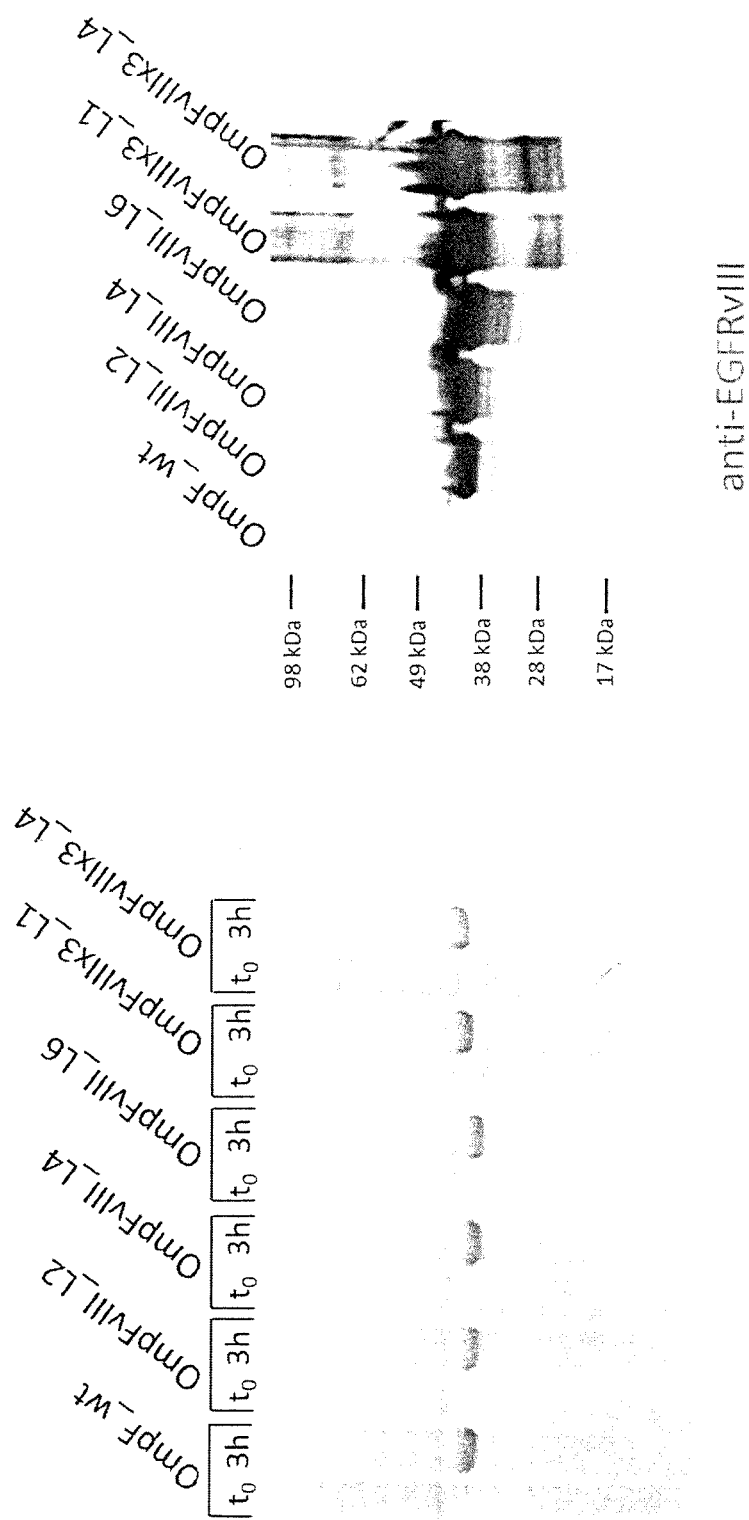
FIG. 10. Analysis of antigen expression in total lysates of BL21(DE3)/ΔompA strain transformed with pET-OmpFvIIIx3 constructs. Total extracts from recombinant clones expressing OmpFvIIIx3 were separated by SDS-PAGE and analysed by COOMASSIE blue staining (A) and Western blot (B). Protein expression was induced by addition of 1 mM IPTG to the culture supernatants and extracts were prepared by collecting bacteria after 3 h induction. Strain expressing OmpF wt was used as a negative control. A few strains expressing vIII in single copy were used to compare induction levels.

Expression of OmpFvIII and OmpFvIIIx3 Heterologous Proteins in E. coli BL21(DE3)/ΔompA The eight plasmids: pET-OmpFvIII_L1, pET-OmpFvIII_L2, pET-OmpFvIII_L4, pET-OmpFvIII_L6, pET-OmpFvIII_L7, pET-OmpFvIII_L8, pET-OmpFvIIIx3_L1 and pET-OmpFvIIIx3_L4 were used to transform E. coli strain BL21(DE3)/ΔompA. Expression of engineered OmpF carrying the vIII peptide in each loop was analyzed in bacterial lysates by SDS-PAGE and Western Blot. E. coli BL21(DE3)/ΔompA strains carrying each plasmid encoding engineered OmpF were grown in LB medium and when cultures reached an $OD_{600}$ value of 0.6, IPTG was added at 1 mM final concentration. After two additional hours of growth at 37° C., cells were collected and 25 µg of total protein extracts were analyzed by SDS-PAGE. As shown in FIG. 9 and FIG. 10A, a protein band with the electrophoretic mobility similar to OmpF accumulated in all protein extracts prepared after IPTG induction. In the case of the two strains carrying plasmid pET-OmpFvIIIx3_L1 and plasmid pET-OmpFvIIIx3_L4, respectively, the bands had an electrophoretic mobility slightly higher than OmpF, in line with the fact that three copies of vIII were used to replace Loop 1 and Loop 4, respectively. Western Blot of total cell extracts was also carried out to confirm the expression of the engineered OmpF proteins in strains carrying plasmids pET-OmpFvIII_L2, pET-OmpFvIII_L4, pET-OmpFvIII_L6, pET-OmpFvIIIx3_L1 and pET-OmpFvIIIx3_L4. To this aim, 13 µg of total proteins from each strain were separated by SDS-PAGE and proteins were transferred to nitrocellulose filters. The filters were blocked overnight at 4° C. by agitation in blocking solution (10% skimmed milk and 0.05% TWEEN in PBS), followed by incubation for 90 minutes at 37 C with a 1:1.000 dilution of rabbit anti-vIII polyclonal antibodies in 1% skimmed milk and 0.05% TWEEN in PBS. After 3 washing steps in PBS-TWEEN, the filters were incubated in a 1:5.000 dilution of peroxidase-conjugated anti-mouse immunoglobulin (Dako) in 1% skimmed milk and 0.05% TWEEN in PBS for 1 hour at room temperature, and after 3 washing steps, bound conjugated IgGs were detected using the Super Signal West Pico chemo-luminescent substrate (Pierce). As shown in FIG. 10B intense immune reactive bands with electrophoretic mobility identical to the corresponding engineered OmpF proteins visible in SDS-polyacrylamide gel stained with COOMASSIE Blue were detected.

Figure 11:
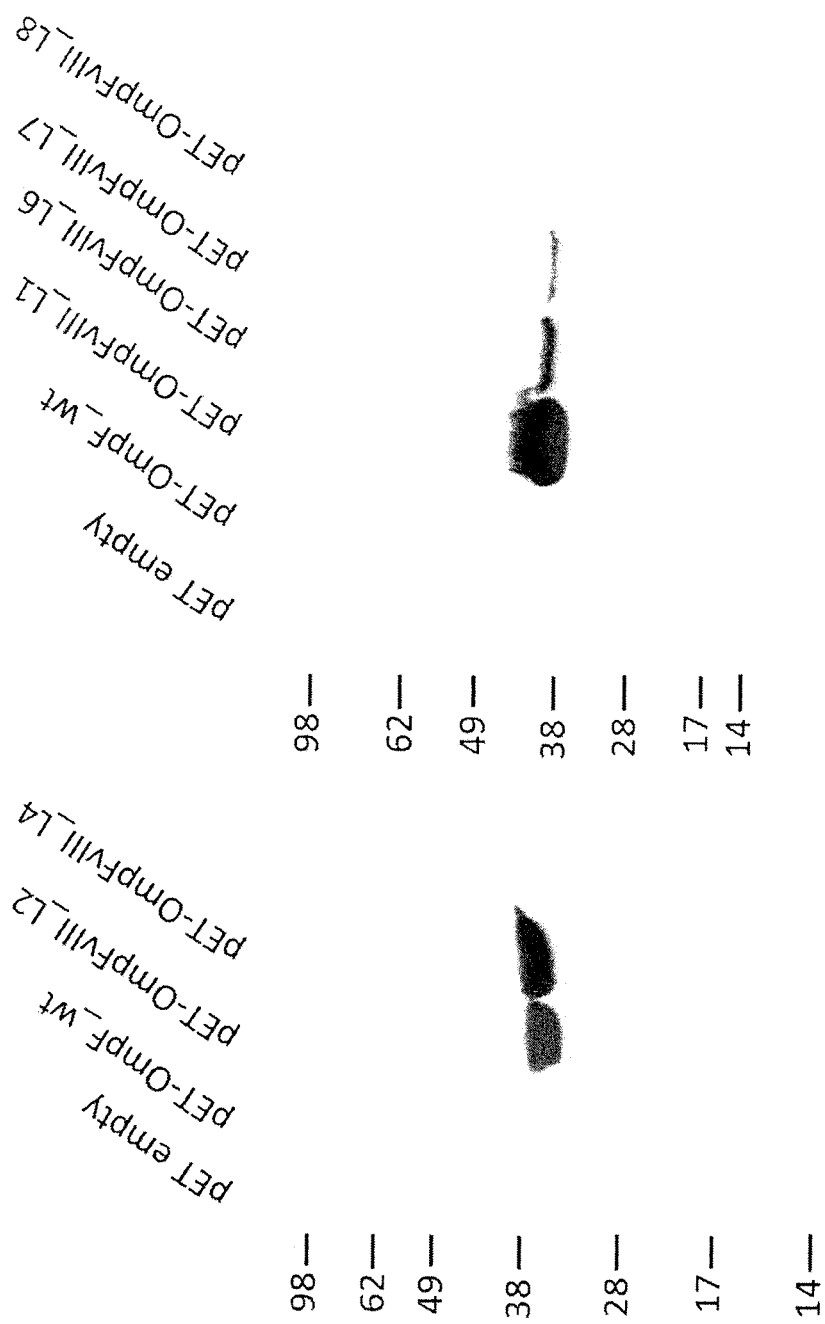
FIG. 11. Western blot analysis of OmpFvIII expression in OMVs. OMVs were purified by ultrafiltration and ultracentrifugation from the supernatants of recombinant strains transformed with pET-OmpFvIII constructs. OMVs were collected from cultures induced with 1 mM IPTG for 2 hours. OMVs were loaded on SDS-polyacrylamide gel and analyzed by Western blot using rabbit polyclonal antibody against purified synthetic EGFRvIII peptide. Strains transformed with empty pET vector and with pET-OmpF_wt plasmid were used as negative controls.
Figure 12:
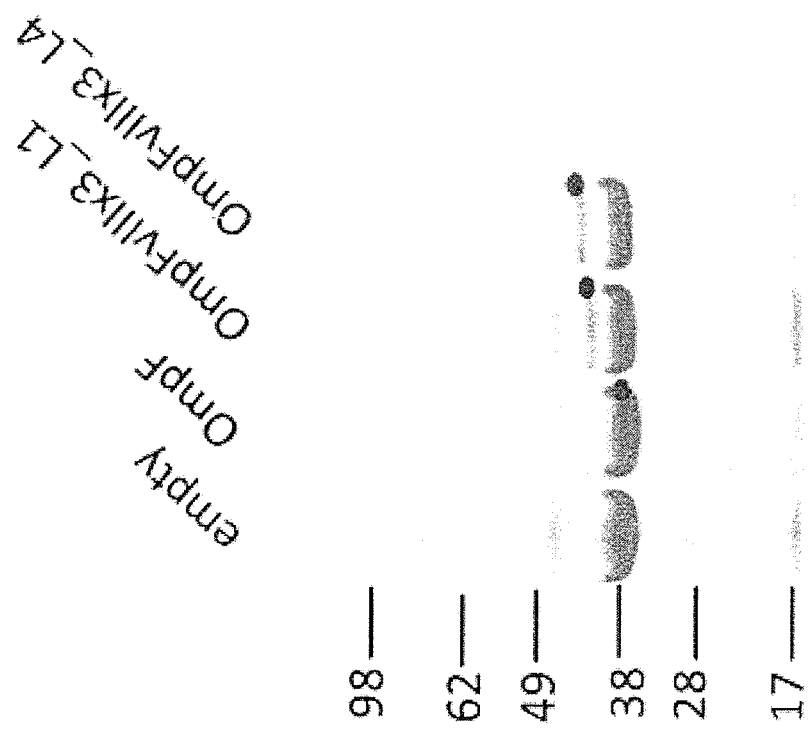
FIG. 12. SDS-PAGE analysis of OmpFvIIIx3 expression in OMVs. OMVs were purified by ultrafiltration and ultracentrifugation from the supernatants of recombinant strains transformed with pET-OmpFvIIIx3 constructs. OMVs were collected from cultures induced with 1 mM IPTG for 2 hours. OMVs were loaded on SDS-polyacrylamide gel and analyzed by COOMASSIE blue staining. Strains transformed with empty pET vector and with pET-OmpF_wt plasmid were used as negative controls.

Expression of OmpFvIII and OmpFvIIIx3 Heterologous Proteins into OMVs Having demonstrated that engineered OmpF carrying one or three copies of vIII peptide in correspondence of one of the OmpF external loops were expressed in E. coli BL21(DE3)/ΔompA, the presence of engineered OmpF in the OMV fraction was analyzed. To this aim, the recombinant strains BL21(DE3)/ΔompA(pET-OmpFvIII_L1), BL21(DE3)/ΔompA (pET-OmpFvIII_L2), BL21(DE3)/ΔompA (pET-OmpFvIII_L4), BL21 (DE3)/ΔompA (pET-OmpFvIII_L6), BL21 (DE3)/ΔompA (pET-OmpFvIII_L7), and BL21(DE3)/ΔompA (pET-OmpFvIII_L8) were grown in LB medium and when the cultures reached an $OD_{600}$ value of 0.6, IPTG was added at 1 mM final concentration. After two additional hours of growth at 37° C., vesicles were purified from culture supernatants by using ultrafiltration coupled to ultracentrifugation. More specifically, OMVs were collected from culture supernatants by filtration through a 0.22 µm pore size filter (Millipore) and by high-speed centrifugation (200,000×g for 2 hours). Pellets containing OMVs were finally suspended in PBS. The presence of the engineered OmpF proteins in each OMV preparation was verified by Western Blot analysis as already described using anti-vIII polyclonal antibodies. As shown in FIG. 11, all OMVs purified from the supernatants of the six recombinant strains carried the respective engineered OmpF proteins. In particular, the OmpF proteins carrying the vIII peptide in place of Loop 1, Loop 2 and Loop 4 appear to accumulate in OMVs with remarkably high efficiency. As far as the two engineered OmpF proteins carrying three copies of vIII peptide in loop 1 and 4 are concerned, their presence in OMVs was verified by SDS-PAGE. BL21(DE3)/ΔompA (pET-OmpFvIIIx3_L1), and BL21(DE3)/ΔompA (pET-OmpFvIIIx3_L4) strains were grown in LB medium and when the cultures reached an $OD_{600}$ value of 0.6, IPTG was added at 1 mM final concentration. After two additional hours of growth at 37° C., vesicles were purified from culture supernatants by using ultrafiltration coupled to ultracentrifugation as described above. 25 µg of OMVs were separated on an SDS-polyacrylamide gel and after protein separation the gel was stained with COOMASSIE Blue. As shown in FIG. 12, a protein band with an apparent molecular weight slightly higher than OmpF was clearly visible in both OMV preparations. The simultaneous presence of both wild type and engineered OmpF in OMVs was in line with the fact that both protein species were expressed in the strains, the wild type OmpF being encoded by the chromosomal DNA while the engineered OmpF being encoded by the recombinant plasmid.

Figure 13:
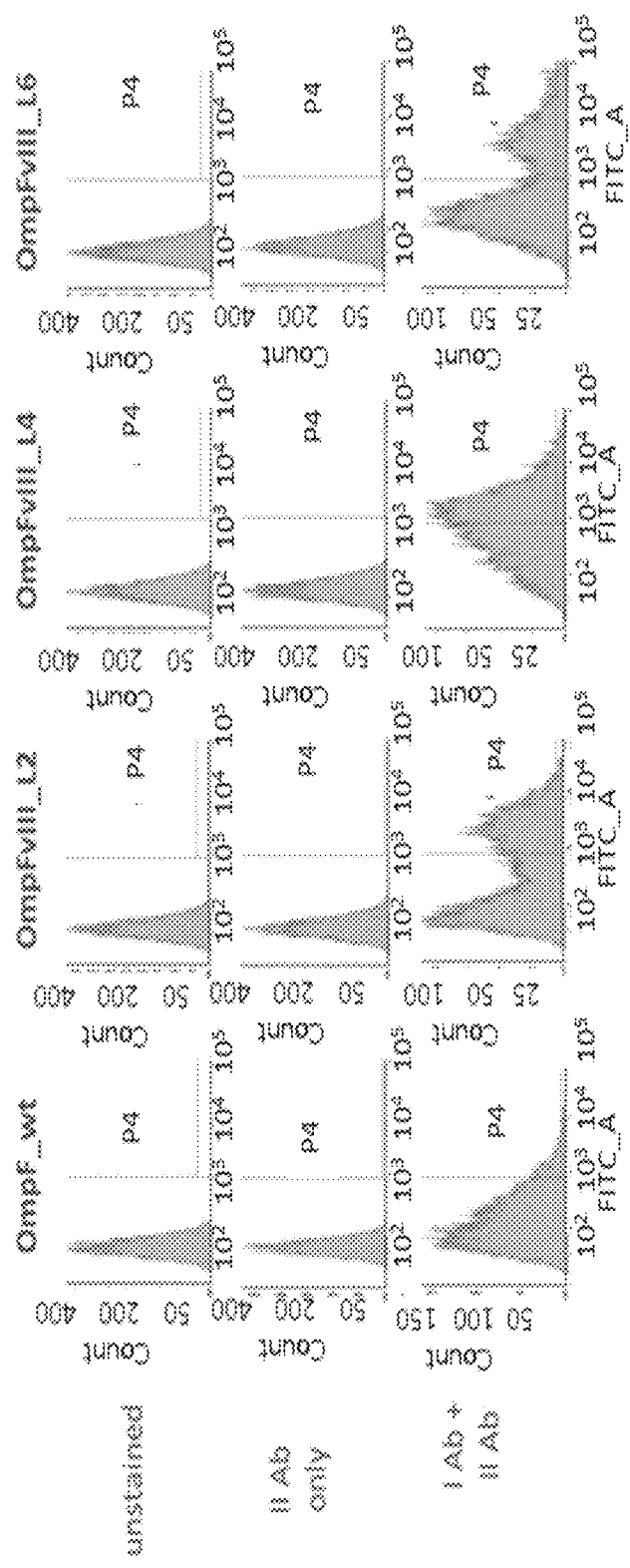
FIGS. 13A-13B. Analysis of surface exposition of vIII in OmpFvIII recombinant strains. Surface expression was evaluated on bacterial cells after 3 h induction with 1 mM IPTG. Cells were stained with 50 µg/ml anti-vIII polyclonal antibody followed by anti-rabbit-FITC secondary antibody. BL21(DE3)/ΔompA strain overexpressing OmpF_wt was used as a negative control. (A) Analysis of vIII surface exposition in strains overexpressing OmpFvIII_L2, OmpFvIII_L4 and OmpFvIII_L6. (B) Analysis of vIII surface exposition in strains overexpressing OmpFvIIIx3_L1 and OmpFvIIIx3_L4.
Figure 13:
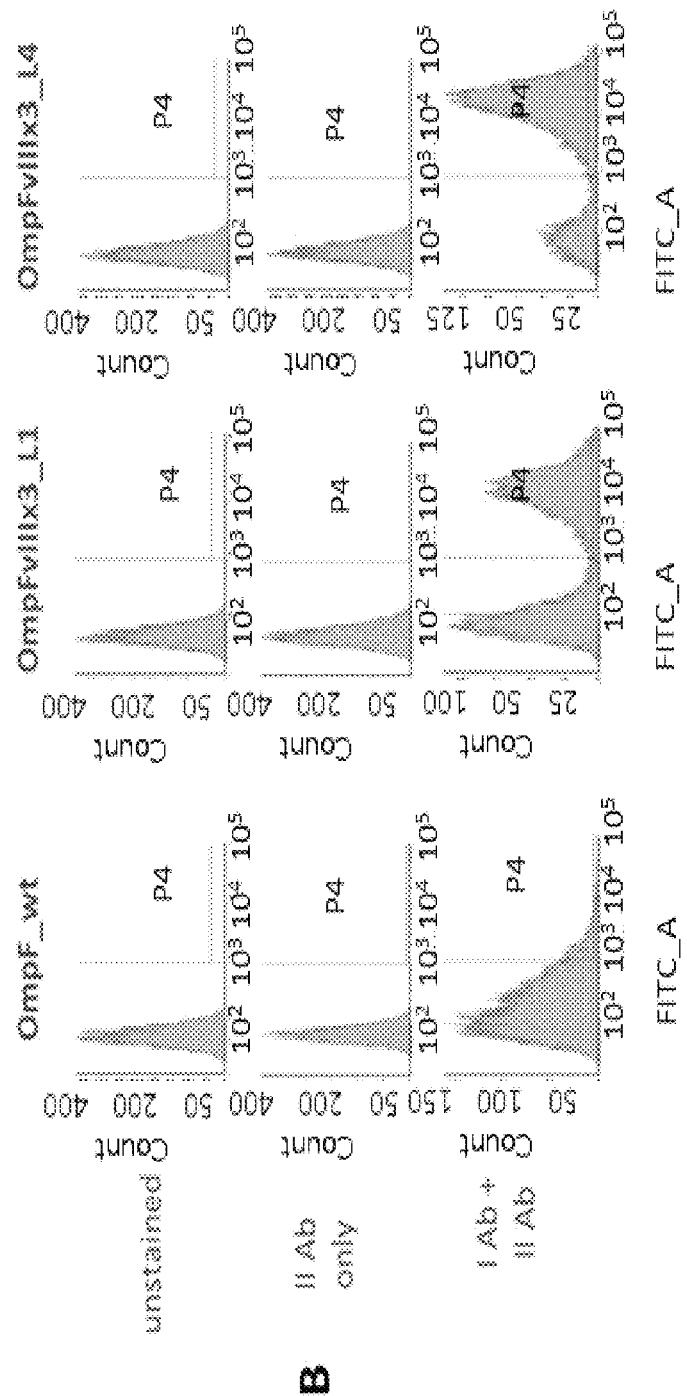
Figure 14:
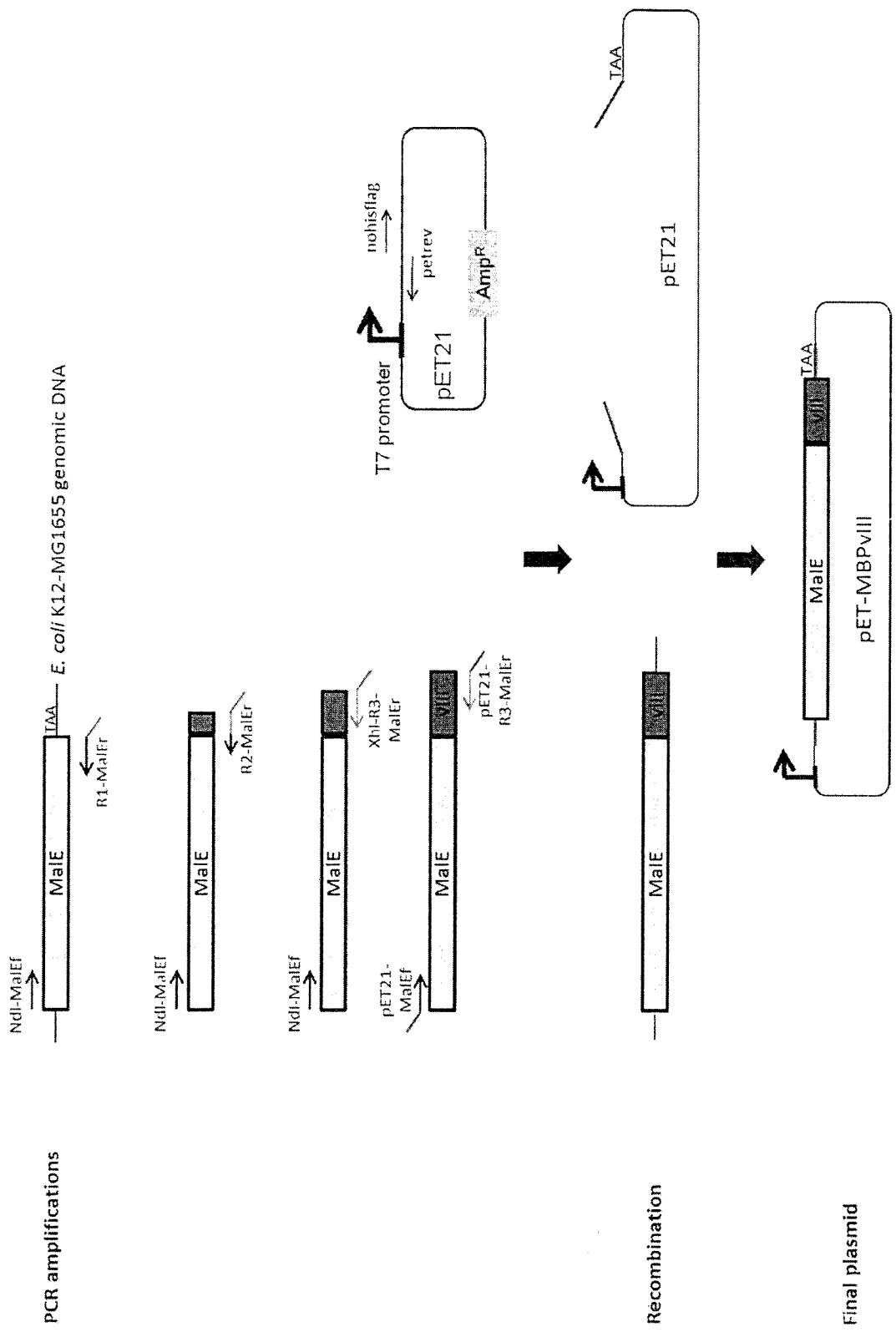
FIG. 14. Cloning strategy used to fuse one copy of the EGRFvIII peptide to MBP. The DNA sequence coding for MBP was amplified by PCR from *E. coli* K12-MG1655 genomic DNA using primers NdI-MalEf/R1-MalEr. The forward primer (NdI-MalEf) anneals to the 5' end of malE; the reverse primer (R1-MalEr) anneals to the 3' end of malE (excluding the stop codon) and its 5' tail contains nucleotides 1-17 of the vIII sequence. Then, in order to complete the vIII coding sequence at the 3' of malE, a second and a third polymerase chain reactions were performed using the same forward primer (NdI-MalEf) but different reverse primers. The reverse primer used in the second amplification step (R2-MalEr) anneals to a region containing the 3' end of malE and nucleotides 1-17 of the vIII sequence; its 5' tail contains nucleotides 18-31 of the vIII sequence. The reverse primer used in the third amplification step (XhI-R3-MalEr) anneals to nucleotides 2-31 of the vIII sequence; its 5' tail contains nucleotides 32-39 of the vIII sequence and the TAA stop codon. With the aim of cloning the fusion gene coding for MBPvIII in pET21 expression vector the PIPE cloning method was used (Klock and Lesley, 2009). Briefly, pET21 was amplified using primers petrev/nohisflag and the fusion gene coding for MBPvIII was reamplified using primers pET21-MalEf/pET21-R3-MalEr, which have 5' tails that generate extremities complementary to pET21 expression vector linear DNA. *E. coli* HK100 transformation leads to the generation of pET-MBPvIII plasmid.
Figure 15:
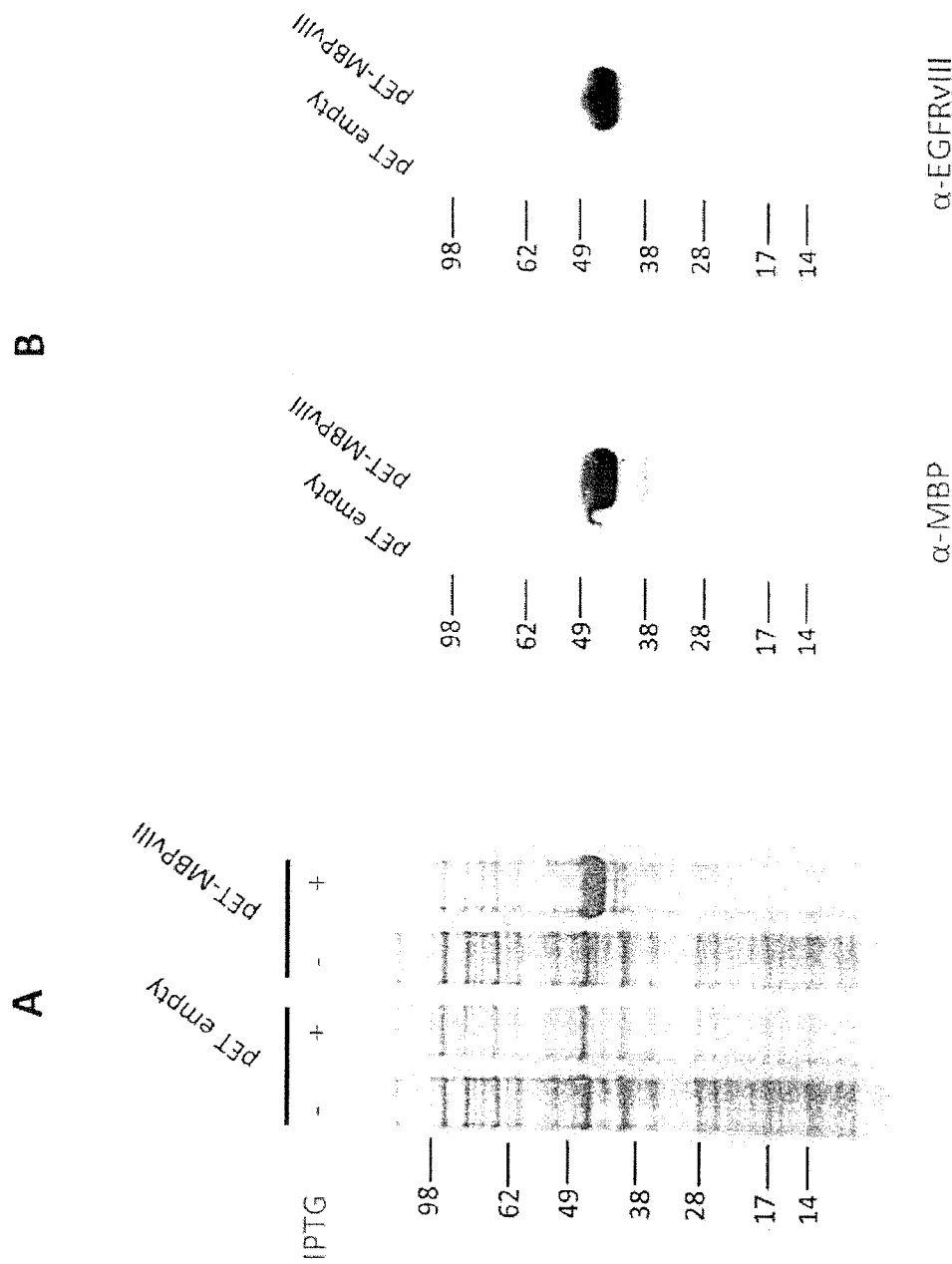
FIGS. 15A-15B. Analysis of antigen expression in total lysates of BL21(DE3)/ΔompA strain transformed with pET-MBPvIII. Total extracts from bacterial cells after induction with 1 mM IPTG were separated by SDS-PAGE and analysed by COOMASSIE blue staining (A) and by Western blot (B). For Western Blot analysis, proteins were transferred from the gel to nitrocellulose membrane and analyzed with anti-MBP mouse monoclonal antibody and anti-EGFRvIII rabbit polyclonal antibody raised against purified synthetic vIII peptide.
Figure 16:
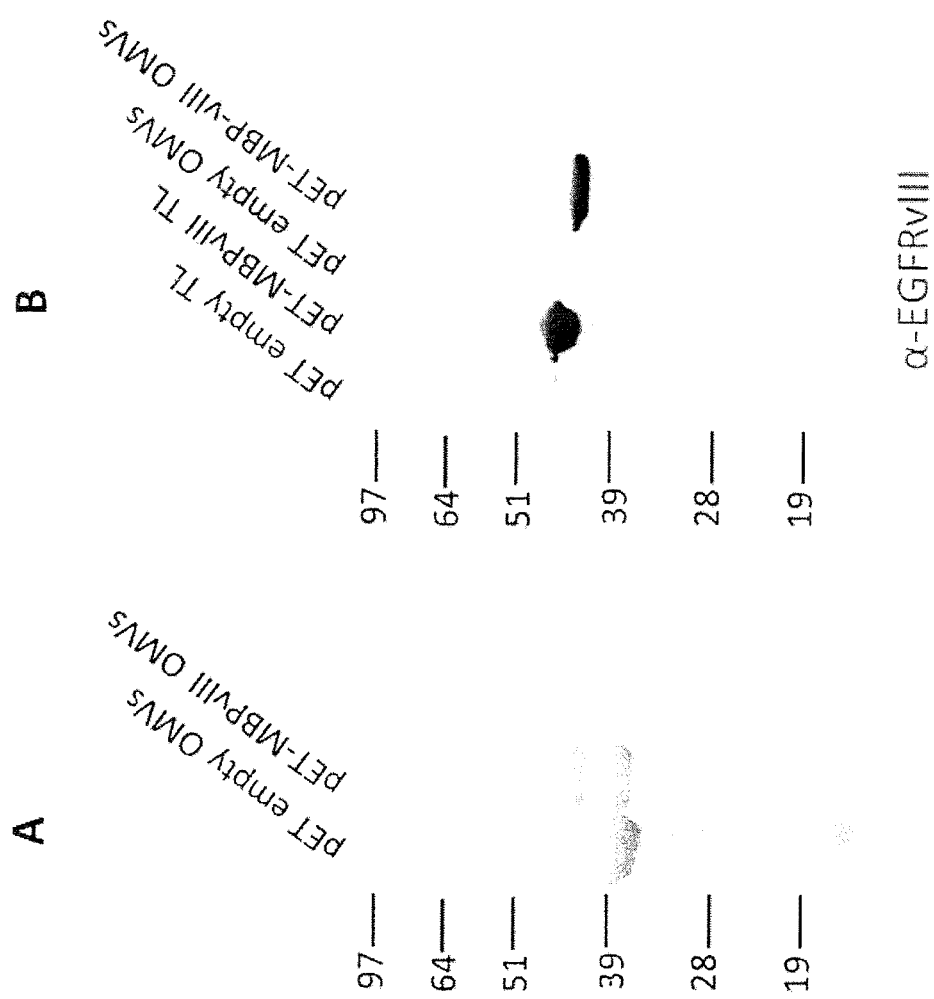
FIGS. 16A-16B. Analysis of MBPvIII expression in OMVs. (A) OMVs were purified by ultrafiltration and ultracentrifugation from the supernatants of a recombinant strain transformed with pET-MBPvIII. OMVs were collected from cultures induced with 1 mM IPTG for 2 hours. 13 µg of OMVs were loaded on SDS-polyacrylamide gel and analyzed by COOMASSIE blue staining. (B) The same OMVs preparations were analyzed by Western blot using rabbit polyclonal antibody against purified synthetic vIII peptide. TL, total lysates; OMVs, outer membrane vesicles.

Analysis of vIII Expression on the Surface of OmpFvIII and OmpFvIIIx3 Recombinant Strains Finally, the surface expression of the vIII peptide was analyzed by Flow Cytometry in BL21(DE3)/ΔompA(pET-OmpFvIII_L2), BL21(DE3)/ΔompA (pET-OmpFvIII_L4), BL21(DE3)/ΔompA (pET-OmpFvIII_L6), BL21(DE3)/ΔompA (pET-OmpFvIIIx3_L1), and BL21(DE3)/ΔompA (pET-OmpFvIIIx3_L4), strains. Bacterial cultures were grown at 37° C. under agitation. When cultures reached an OD600 value of 0.6, IPTG was added at a final concentration of 1 mM and bacteria were grown for 3 additional hours. Subsequently, 1 ml bacteria cells were collected by centrifugation at 5,000×g for 5 minutes. After a wash in 1% BSA/PBS bacteria were resuspended in 5 ml 1% BSA/PBS. 50 μl of cell suspensions were incubated with 5 μl of an appropriate dilution of rabbit anti-vIII polyclonal antibodies raised against the vIII peptide conjugated to Keyhole Limpet Hemocyanin (KLH) or, as negative control, with 5 μl of PBS containing 1% BSA. After 1 hour, the suspensions were centrifuged at 5.000×g for 5 minutes and supernatants discarded. Pellets were washed with 100 μl of PBS containing 1% BSA and bacteria subsequently incubated for 1 hour at 4° C. with goat anti-rabbit antibodies (Alexa flour488, Life Technology) added at a final dilution of 1:200. Finally, after a wash step, pellets were fixed with 100 μl 4% formaldehyde/PBS, re-suspended in 100 μl of PBS and analyzed with FACS CANTOII evaluating collected data with FlowJo software. As shown in FIG. 13, in the presence of anti-vIII antibodies, a clear shift in fluorescence intensity was observed in a substantial fraction of bacterial cells expressing the engineered OmpF proteins. No difference in fluorescence intensity was observed when *E. coli* BL21 (DE3)/ΔompA expressing OmpF wt was incubated with anti-vIII antibodies. These data indicate that when used to replace the OmpF external loops, vIII peptide appeared on the surface of bacteria expressing the engineered OmpF proteins. Surface exposition was particularly pronounced when three copies of vIII peptide were used to replace the L1 and L4 loops of OmpF.

Figure 17:
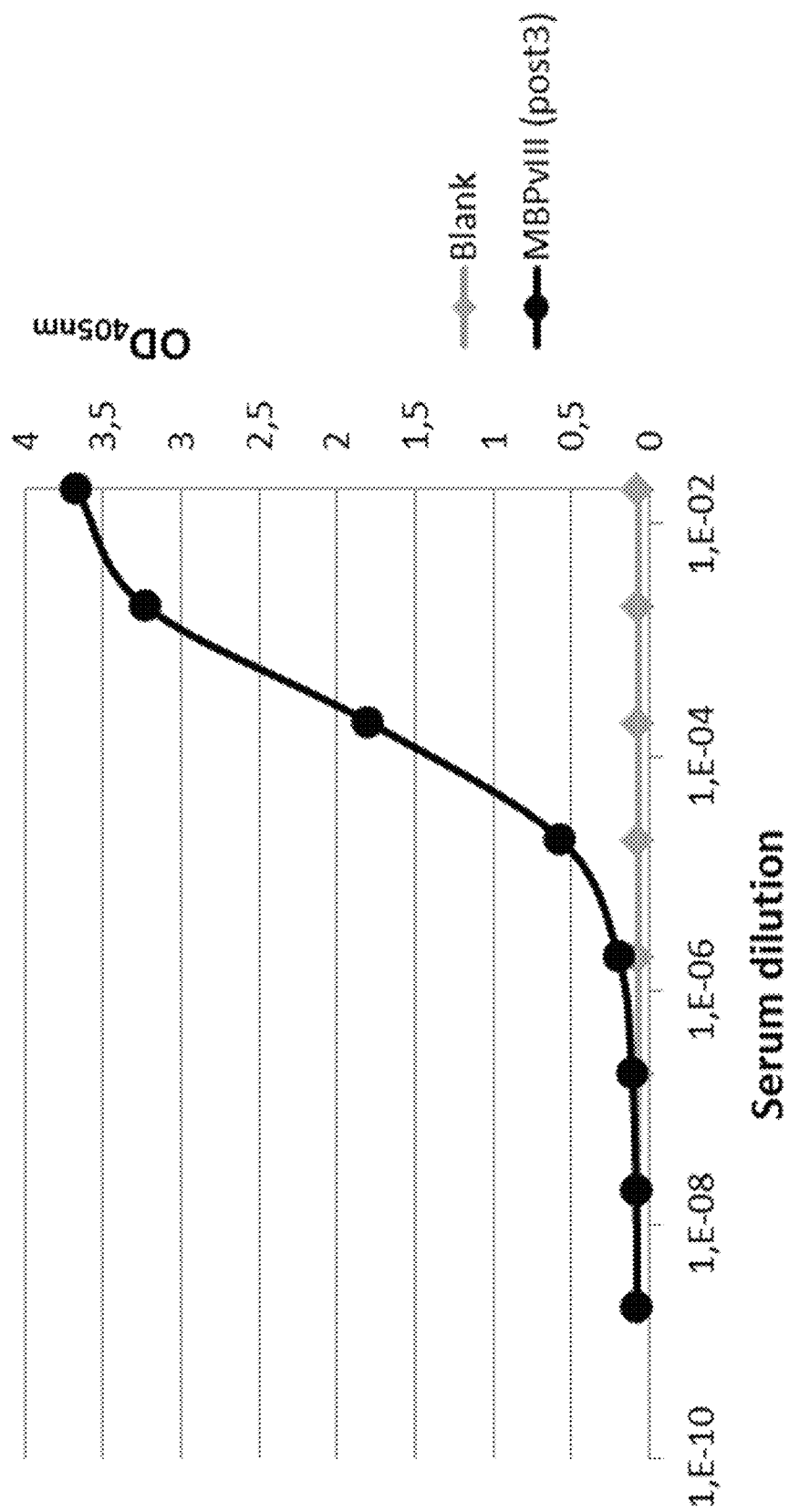
FIG. 17. Analysis of EGFRvIII-specific IgG induced in mice immunized with OMVs expressing MBPvIII. Antigen-specific IgGs were measured by ELISA in sera from mice immunized with three doses of OMVs expressing MBPvIII. Anti-mouse IgGs conjugated to alkaline phosphatase were used as secondary antibody. OD405 was measured for each serum dilution.

OMV Engineering with MBPvIII pET-MBPvIII Plasmid Construction

In an attempt to deliver EGFRvIII peptide to the lumen of OMVs, the Maltose binding protein (MBP), which is naturally delivered to the periplasm, was used as a carrier (FIG. 1D). In essence, a fusion protein was designed constituted by the whole MBP carrying the 13 amino acid vIII peptide at its carboxyl terminus (FIG. 2A). For this purpose, the DNA sequence coding for MBP was amplified by PCR from *E. coli* K12-MG1655 genomic DNA, using primers NdI-MalEf and R1-MalEr. The forward primer (NdI-MalEf) anneals to the 5' end of malE, the gene coding for MBP; the reverse primer (R1-MalEr) anneals to the 3' end of malE (excluding the stop codon) and its 5' tail contains nucleotides 1-17 of the vIII sequence. Then, in order to complete the vIII coding sequence at the 3' of malE, a second and a third polymerase chain reactions were performed using the same forward primer (NdI-MalEf) but different reverse primers. The reverse primer used in the second amplification step (R2-MalEr) anneals to a region containing the 3' end of malE and nucleotides 1-17 of the vIII sequence; its 5' tail contains nucleotides 18-31 of the vIII sequence. The reverse primer used in the third amplification step (XhI-R3-MalEr) anneals to nucleotides 2-31 of the vIII sequence; its 5' tail contains nucleotides 32-39 of the vIII sequence and the TAA stop codon (Table 1 and FIG. 14). With the aim of cloning the fusion gene coding for MBPvIII in pET21 expression vector the PIPE cloning method was used (Klock and Lesley, 2009). Briefly, pET21 was amplified using primers petrev/nohisflag and the fusion gene coding for MBPvIII was reamplified using primers pET21-MalEf/pET21-R3-MalEr, which have 5' tails that generate extremities complementary to pET21 expression vector linear DNA (Table 1 and FIG. 14). *E. coli* HK100 transformation leads to the generation of pET-MBPvIII plasmid. The correctness of the cloning of the MBPvIII fusion in pET21 was verified by DNA sequencing (SEQ ID NO:101).

Expression of MBPvIII Heterologous Protein in *E. coli* BL21(DE3)/ΔompA

The recombinant plasmid encoding MBP fused to one copy of the EGFRvIII peptide was used to transform *E. coli* strain BL21(DE3)/ΔompA.

One recombinant strain was obtained: BL21(DE3)/ΔompA(pET-MBPvIII). The strain was grown in LB medium and when culture reached an OD600 value of 0.6, IPTG was added at 1 mM final concentration.

After two additional hours of growth at 37° C., cells were collected and 25 μg of total protein extracts were analyzed by SDS-PAGE. As shown in FIG. 15A, a protein band with an electrophoretic mobility corresponding to MBPvIII accumulated in the protein extract prepared after IPTG induction. Western Blot of total cell extracts was also carried out to confirm the expression of MBPvIII. To this aim, 13 μg of total proteins from each strain were separated by SDS-PAGE and proteins were transferred to nitrocellulose filters. The filters were blocked for 2h at room temperature by agitation in blocking solution (10% skimmed milk and 0.05% TWEEN in PBS), followed by incubation for 90 minutes at 37° C. with a 1:1.000 dilution of rabbit anti-vIII polyclonal antibodies or mouse anti-MBP monoclonal antibody in 1% skimmed milk and 0.05% TWEEN in PBS. After 3 washing steps in PBS-TWEEN, the filters were incubated in a 1:5,000 dilution of peroxidase-conjugated anti-rabbit or anti-mouse immunoglobulin (Dako) in 1% skimmed milk and 0.05% TWEEN in PBS for 1 hour at room temperature, and after 3 washing steps, bound conjugated IgGs were detected using the Super Signal West Pico chemo-luminescent substrate (Pierce). As shown in FIG. 15B, EGFRvIII fused to MBP was found expressed in the cell lysates. No immune reactive bands were detected in total lysates from *E. coli* cells carrying empty pET21 plasmid.

Expression of MBPvIII into OMVs

Having demonstrated that MBPvIII was expressed in *E. coli* BL21(DE3)/ΔompA strain, the presence of the antigen in the OMV fraction was analyzed. Strain BL21(DE3)/ΔompA(pET-MBPvIII) was grown in LB medium and when the culture reached an OD600 value of 0.6, IPTG was added at 1 mM final concentration. After two additional hours of growth at 37° C., vesicles were purified from culture supernatants by using ultrafiltration coupled to ultracentrifugation. More specifically, OMVs were collected from culture supernatants by filtration through a 0.22 μm pore size filter (Millipore) and by high-speed centrifugation (200,000×g for 2 hours). Pellets containing OMVs were finally suspended in PBS. The presence of the antigens in OMVs preparations was verified by SDS-PAGE and Western Blot analyses as described in the previous section. Data indicate that MBP carrying one copy of vIII peptide was incorporated into OMVs (FIGS. 16A and B).

Antibody Titers Elicited in Mice Immunized with MBPvIII in Engineered OMVs

To test whether OMVs purified from BL21(DE3)/ΔompA strain expressing MBPvIII were able to induce EGFRvIII-specific antibody responses, CD1 mice were i.p. immunized three times at two-week interval with 10 μg OMVs in Alum. Blood samples were collected nine days after third dose administration and anti-vIII IgGs were detected by using plates coated in each well with 0.5 μg of synthetic vIII peptide conjugated to Keyhole limpet hemocyanin (vIII-KHL). PBS containing 1% BSA was used as negative control. More specifically, coating was carried out by incubating plates overnight at 4° C. with 100 μl of conjugated peptide (5 μg/ml). Subsequently, wells were washed three times with PBST (0.05% TWEEN 20 in PBS, pH 7.4), incubated with 100 μl of 1% BSA in PBS for 1 h at room temperature and washed again three times with PBST. Serial dilutions of serum samples in PBST containing 1% BSA were added to the plates, incubated 2 h at 37° C., and washed three times with PBST. Then 100 μl/well of 1:2,000 diluted, alkaline phosphatase-conjugated goat anti-mouse IgGs were added and left for 2 h at 37° C. After triple PBST wash, bound alkaline phosphatase-conjugated antibodies were detected by adding 100 μl/well of 3 mg/ml para-nitrophenyl-phosphate disodium hexahydrate (Sigma-Aldrich) in 1M diethanolamine buffer (pH 9.8). After 10 minute incubation at room temperature, the reaction was stopped with 100 μl 7% EDTA and substrate hydrolysis was analyzed at 405 nm in a microplate spectrophotometer. As shown in FIG. 17, OMVs carrying MBPvIII fusion protein were able to induce high anti-vIII IgG titers in mice.

Engineered OMVs Expressing FAT1 Peptide

Two strategies were designed to deliver the FAT1 peptide to the E. coli OMVs. The first strategy envisaged the fusion of FAT1 peptide to the carboxyl terminus of either full length fHbp or fHbpDomA. For this purpose, a synthetic DNA fragment encoding three copies of IQVE-ATDKDLGPNGHVTYSIVTDTD (SEQ ID NO:6) peptide was ligated to the 3' end of the full length fHbp gene and to the DNA sequence coding for the Domain A of fhbp (fHbpDomA), thus generating chimeric proteins carrying the FAT1 peptide at their C-terminus.

The second strategy was designed to deliver the FAT1 peptide into the lumen of OMVs. To this aim, the synthetic DNA coding for three copies of the FAT1 peptide was fused to the 3' end of the MBP gene to create an in frame C-terminal fusion.

Construction of pET21_FL-fHbp-FAT1 and pET21_fHbp-DomA-FAT1 Plasmids

The fusion of three copies of the FAT1 peptide to full length fHbp (FL-fHbp) and to fHbp-DomA was carried out in two main steps. First, the DNA fragments encoding FL-fHbp and fHbp-DomA were cloned into plasmid pET21, thus generating plasmids pET21-fHbp and pET21-fHbp-DomA. Subsequently, the two plasmids were linearized to clone the synthetic DNA encoding three copies of FAT1 peptide (FAT1 Minigene) at the end of fHbp and fHbp-DomA coding sequences. The sequence of FAT1 Minigene was designed taking into consideration BL21 E. coli codon usage (SEQ ID NO:102).

pET21_FL-fHbp and pET21_fHbp-DomA were generated as described in section 5.1.1.

To generate pET21_FL-fHbp-FAT1 and pET21_fHbp-DomA-FAT1 plasmids, pET21-fHbp and pET21-fHbp-DomA were linearized by PCR amplification using the two couples of primers FHBP-F/FHBPFL-R and FHBP-F/FHBPDA-R (Table 2) and the linear fragments were combined with the synthetic DNA coding for FAT1 Minigene (Table 2, Sequence 18). FAT1 Minigene was constructed by assembling six complementary oligonucleotides the sequence of which is reported in Table 2 and the assembled DNA fragment was amplified with primers F-FATFH/R-FATFH F-FATDomA/R-FATFH (Table 2) to make its extremities complementary to linearized pET21_FL-fHbp and pET21_FL-fHbpDomA, respectively. The DNA mixtures were then used to transform E. coli HK100 competent cells and clones carrying pET21_FL-fHbp-FAT1 and pET21_fHbp-DomA-FAT1 plasmids were selected on LB agar plates supplemented with 100 μg/ml Amplicillin. From one clone of each transformation the plasmid was purified and the correctness of the fHbp-FAT1 and fHbpDomA-FAT1 gene fusions was verified by DNA sequencing (SEQ ID NOs:104 and 103).

pET-MBP-FAT1 Plasmid Construction

To express FAT1 peptide in the lumen of OMVs, the Maltose binding protein (MBP) which is naturally delivered to the periplasm was used as a carrier and the FAT1 Minigene was cloned as an in frame fusion to the 3' end of the MBP gene. For this purpose, plasmid pET-MBPvIII (see Section 5.1.3) has been used as template for a PCR reaction carried out according to the PIPE method (Klock H. E. and Lesley S. A (2009) Methods Mol. Biol. 498, 91-103), using primers pET21-MBPF and pET21-MBPR (see Table 2) to generate a linear fragment missing the vIII coding sequence. Then, the linear fragment was ligated to FAT1 Minigene, which was assembled in vitro using the six synthetic oligonucleotides reported in Table 2 and subsequently amplified with primers MBPFA-F and MBPFA-R. The DNA mixture was used to transform MK-100 competent cells and clones carrying pET-MBP-FAT1 plasmid were selected on LB agar plates supplemented with 100 μg/ml of Ampicillin. The correctness of the MBP and FAT1 Minigene fusion in pET-MBP-FAT1 plasmid purified from one of the Ampicillin resistant clones was verified by DNA sequencing (SEQ ID NO:105).

Expression of fHBP-FAT1 and MBP FAT1 Peptide in E. coli BL21(DE3)ΔompA

Plasmids pET21_FL-fHbp-FAT1, pET21_fHbp-DomA-FAT1 and pET-MBP-FAT1 were used to transform BL21 (DE3) ΔompA strain. Recombinant clones were grown in 200 ml LB medium at 37 C and when the cultures reached OD600=0.6, the expression of the fusion proteins was induced by addition of 1 mM IPTG. After 2 hour growth, the expression of protein fusions was assessed by SDS-PAGE and Western Blot. To this aim, the equivalent in volume of 1 $OD_{600}$ of each bacterial culture was collected, centrifuged at 13,000×g for 5 minutes and pellets were lysed in 200 μl of BPer Reagent, Lysozime 1 mg/ml, DNAase 10 U/ml and 0.1 mM $MgCl_2$ for 30 minutes. Then the samples were centrifuged at 13.000×g for 20 minutes to separate the supernatants (soluble fraction) from the pellets (insoluble fraction). The soluble fraction was collected (200 μl) and diluted with 100 μl of 4× SDS-PAGE loading buffer while the pellets were re-suspended in 300 μl of 2× loading buffer. 20 μl of each sample were loaded onto an SDS-polyacrylamide gel and the proteins separated by electrophoresis (SDS-PAGE).

TABLE 2

Primers used to fuse FAT1 and MUC1 to fHbp and fHbpDomA using plasmids pET21_fHbpFL and pET21_fHbpDomA

| | |
|---|---|
| fHbp-F | TAACATCACCATCACCATCACGATTACAAAGA (SEQ ID NO: 69) |
| fHbpFL-R | TTATTGCTTGGCGGCAAGGC (SEQ ID NO: 70) |

TABLE 2-continued

| | |
|---|---|
| fHbpDomA-R | TTGTTTGTATACTTGGAACTCTCCACTCTC<br>(SEQ ID NO: 71) |

Primers used to fuse FAT1 and MUC1 to MBP using plasmid pET21-MBPvIII

| | |
|---|---|
| pET21-MBPF | CATCACCATCACCATCACGATTAC<br>(SEQ ID NO: 72) |
| pET21-MBPR | CTTGGTGATACGAGTCTGCGCGTC<br>(SEQ ID NO: 73) |

Oligos used to assemble the synthetic gene (FAT1 Minigene) coding for three copies FAT1 peptide

| | |
|---|---|
| F1-FAT | ATTCAAGTGGAAGCGACTGACAAAGATCTGGGCCCGAATG<br>GCCAT<br>(SEQ ID NO: 74) |
| R1-FAT | ATCTGTATCCGTAACGATTGAATAAGTTACATGGCCATTCG<br>GGCC<br>(SEQ ID NO: 75) |
| F2-FAT | ACGGATACAGATATCCAGGTAGAGGCAACCGATAAAGATT<br>TAGGTCCC<br>(SEQ ID NO: 76) |
| R2-FAT | GGTATCCGTTACGATACTATATGTGACGTGGCCATTGGGAC<br>CTAAATC<br>(SEQ ID NO: 77) |
| F3-FAT | GTAACGGATACCGACATTCAGGTGGAAGCTACCGATAAAG<br>ACCTGGGTCCG<br>(SEQ ID NO: 78) |
| R3-FAT | ATCTGTATCGGTAACAATAGAATACGTCACGTGACCATTCG<br>GACCCAGGTC<br>(SEQ ID NO: 79) |

Primers to insert FAT1 Minigene gene into pET21_fHbpFL, pET21_fHbpDomA and pET21_MBP

| | |
|---|---|
| F-FATFH | CTTGCCGCCAAGCAAATTCAAGTGGAAGCG<br>(SEQ ID NO: 80) |
| F-FATDomA | CAAGTATACAAACAAATTCAAGTGGAAGCG<br>(SEQ ID NO: 81) |
| R-FATFH | GTGATGGTGATGGTGATGTTAATCTGTATCGGTAAC<br>(SEQ ID NO: 82) |
| MBPFA-F | CGCGCAGACTCGTATCACCAAGATTCAAGTGGAAGCG<br>(SEQ ID NO: 83) |
| MBPFA-R | TCGTGATGGTGATGGTGATGTTAATGCGCCGGCGGAGC<br>(SEQ ID NO: 84) |

Then the gel was stained with COOMASSIE blue overnight at room temperature. For Western blot analysis 5 µl of the same samples were loaded onto a 4-12% polyacrilamide gel (Invitrogen). After electrophoretic separation proteins were transferred onto nitrocellulose filter by standard methods. The filters were blocked overnight at 4° C. by agitation in blocking solution (10% skimmed milk and 0.1% TWEEN in PBS), followed by incubation for 90 minutes at 37° C. with anti-FAT1 mAb198.3 at 3 µg/ml in 1% skimmed milk and 0.1% TWEEN in PBS. After three washing steps in PBS-TWEEN, the filters were incubated in a 1:5.000 dilution of peroxidase-conjugated anti-mouse immunoglobulin (PerkinElmer) in 1% skimmed milk and 0.1% TWEEN in PBS for an hour, and after three washing steps, bound conjugated IgGs were detected using the Super Signal West Pico chemo-luminescent substrate (Pierce) and the resulting signal was detected by using the Western lighting plus ECL (PerkinElmer).

Figure 18:
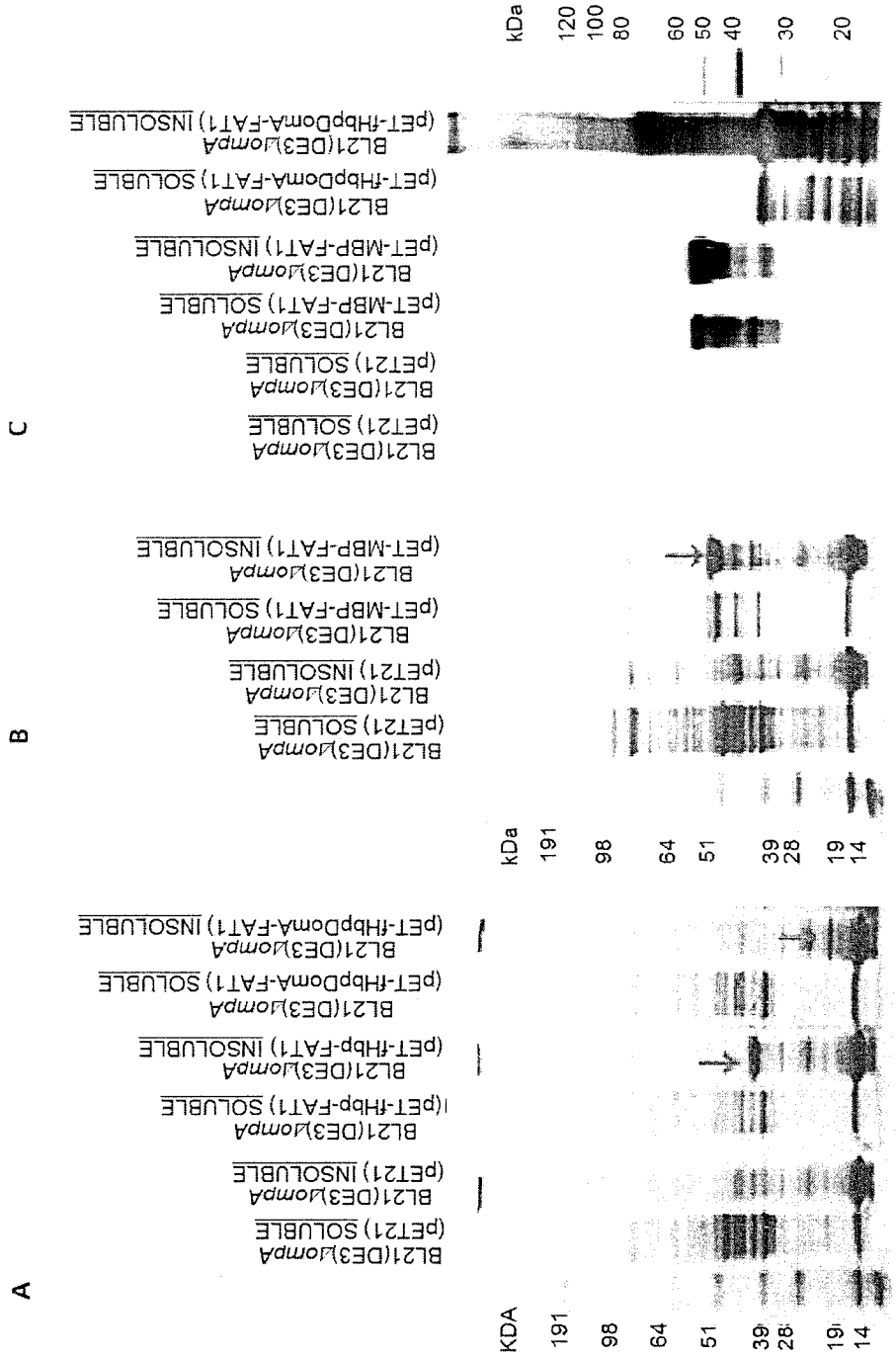
FIGS. 18A-18C. SDS-PAGE and Western Blot analyses of proteins preparations from BL21(DE3) ΔompA recombinant strains expressing fHbp-FAT1, fHbpDomA-FAT1 and MBP-FAT1 fusions proteins. A) Recombinant clones were grown in LB at 37 C and when the cultures reached OD600=0.6, the expression of the fusion proteins was induced by addition of 1 mM IPTG. After 2 hour growth, the equivalent in volume of 1 $OD_{600}$ of each bacterial culture was collected, centrifuged at 13,000×g for 5 minutes and pellets were lysed in 200-1 of Bacterial protein Extraction Reagent (BPer) (Thermo Scientific, Cat. Number 78266), Lysozime 1 mg/ml, DNAase 10 U/ml and 0.1 mM $MgCl_2$ for 30 minutes. The samples were centrifuged at 13.000×g for 20 minutes to separate the supernatants (soluble fraction) from the pellets (insoluble fraction). The soluble fractions were collected (200 µl) and diluted with 100 µl of 4× SDS-PAGE loading buffer while the pellets were re-suspended in 300 µl of 2× loading buffer. 20 µl of each sample were analyzed by SDS-PAGE. B) For Western blot analysis 5 µl of the samples prepared as described in A) were loaded onto a 4-12% polyacrilamide gel, transferred to a nitrocellulose filter and fusion proteins carrying FAT1 peptide visualized by using the FAT1-specific mAb 198.3. C) The Western Blot analysis using anti-FAT mAb198.3 confirmed that the proteins expressed after IPTG inductioon carried the FAT1 peptide.

As shown in FIG. 18A and FIG. 18B, protein species with apparent molecular mass corresponding fHbp-FAT1, fHbpDomA-FAT1 and MBP-FAT1 were clearly visible after COOMASSIE Blue staining of SDS-polyacrylamide gels. The proteins largely compartmentalized in the insoluble fraction and were expressed after IPTG induction. The Western Blot analysis using anti-FAT1 mAb198.3 confirmed that the proteins expressed after IPTG induction carried the FAT1 peptide (FIG. 18C).

Expression of fHbp-FAT1, fHbpDomA-FAT1 and MBP-FAT1 into OMVs

Figure 19:
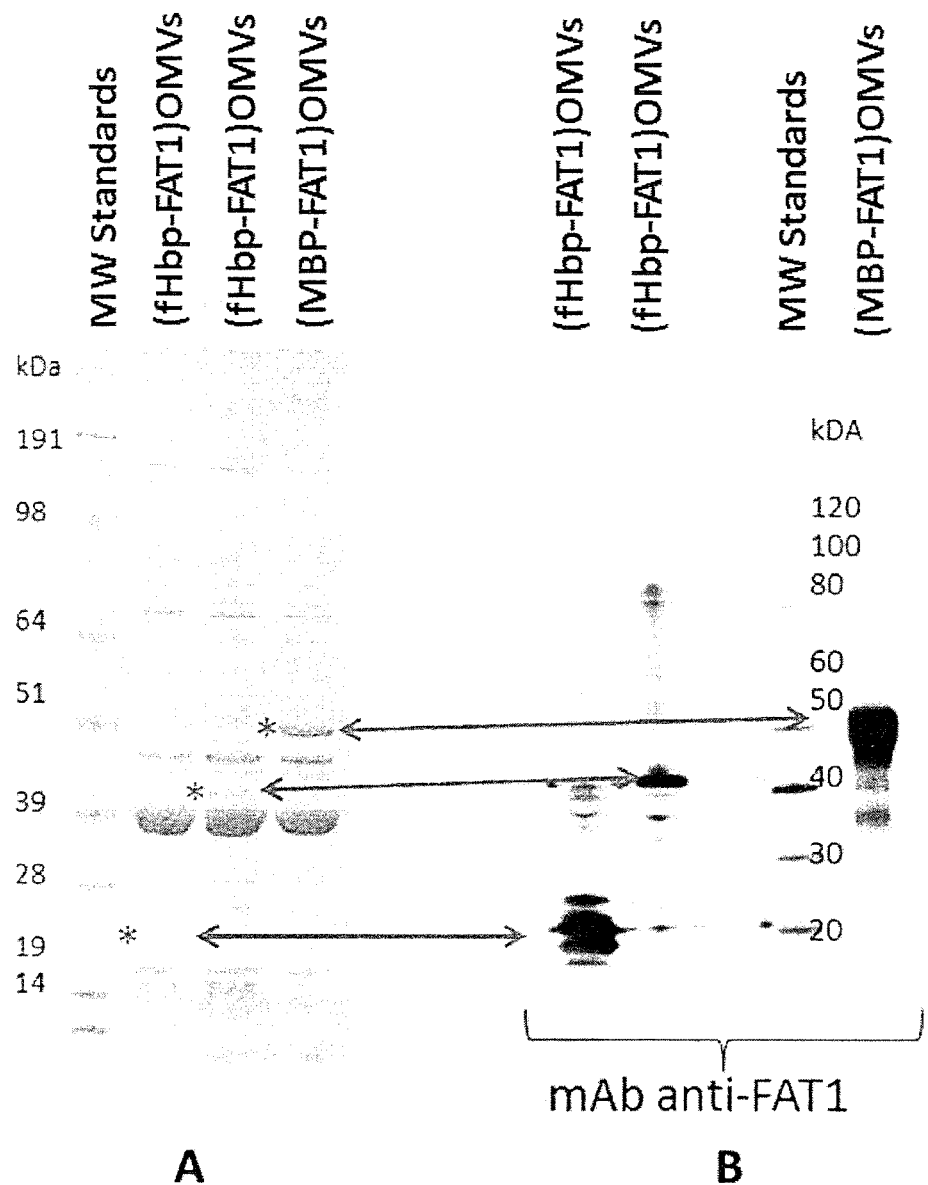
FIGS. 19A-19B. SDS-PAGE and Western Blot analyses of OMVs preparations purified from BL21(DE3)ΔompA recombinant strains expressing fHbp-FAT1, fHbpDomA-FAT1 and MBP-FAT1 fusions proteins. A) BL21(DE3)/ΔompA (pET-fHbp-FAT1), BL21(DE3)/ΔompA (pET-fHbpDomA-FAT1) and BL21(DE3)/ΔompA (pET-MBP-FAT1) strains were grown in LB and when the cultures reached an $OD_{600}$=0.6 1 mM IPTG was added. OMVs were purified from the culture supernatants by using ultrafiltration coupled to ultracentrifugation. 10 µg of total proteins of each OMV preparation were analyzed by SDS-PAGE. B) For Western blot analysis the samples prepared as described in A) were loaded onto a 4-12% polyacrilamide gel, transferred to a nitrocellulose filter and fusion proteins carrying FAT1 peptide visualized by using the FAT1-specific mAb 198.3.
Figure 20:
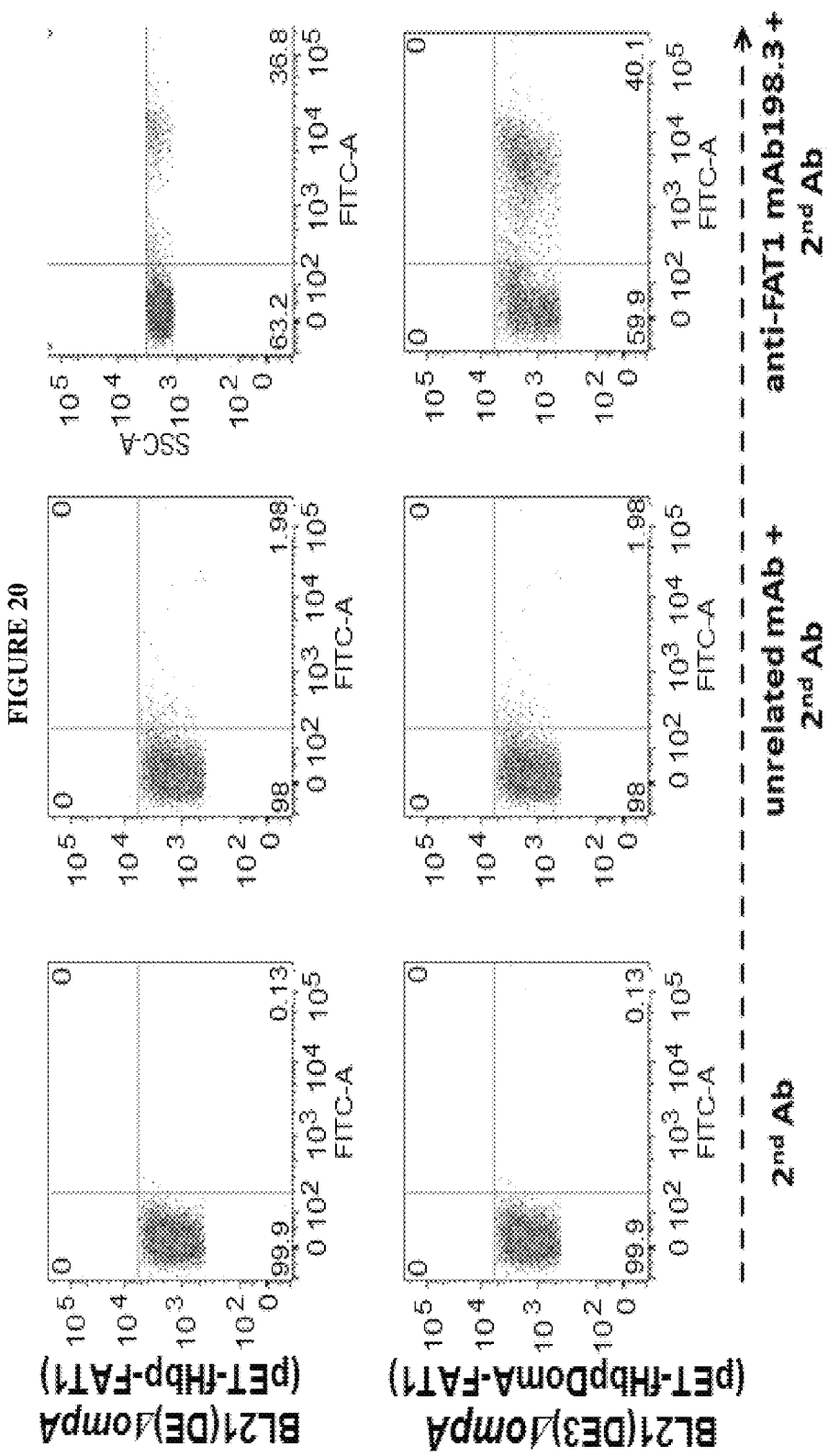
FIG. 20. Analysis of fHBP-FAT1 and fHBPDomA-FAT1 expression on the surface of *E. coli* BL21(DE3)-ompA strain by FACS.

Having demonstrated that fHbp-FAT1, fHbpDomA-FAT1 and MBP-FAT1 peptide were expressed in E. coli BL21 (DE3)/ΔompA, the presence of the fusions in the OMV fraction was analyzed. 200 ml of the bacterial cultures BL21(DE3)/ΔompA (pET-fHbp-FAT1), BL21(DE3)/ΔompA (pET-fHbpDomA-FAT1) and BL21(DE3)/ΔompA (pET-MBP-FAT1) were grown in LB and when the cultures reached an $OD_{600}$=0.6 were induced with 1 mM IPTG. Vesicles were purified from the culture supernatants by using ultrafiltration coupled to ultracentrifugation. Briefly, cultures were centrifuged at 4000×g for 15 min, and the supernatants were concentrated using a membrane with a cut off of 100 kDA (Amicon) until a final volume of 30 ml was reached. Then an ultracentrifugation step was performed at 160.000×g for 2 hours. The pellets were re-suspended in 200 µl of PBS. Protein quantization was performed by DC Protein Assay (BioRad). The presence of the specific antigen in OMVs preparation was verified by Western Blot and SDS-PAGE analysis as already described by loading 10 µg of total proteins of each OMV preparation. As shown in FIG. 19A the three fusion constructs compartmentalized in OMVs with bands corresponding to the expected molecular mass visible by Coomoassie Blue staining of the gels.

The presence of FAT1 peptide in the three fusion proteins was also confirmed by Western Blot, where the anti FAT1 mAb198.3 recognized the three protein species visible in the OMVs preparations by COOMASSIE Blue staining (FIG. 19B).

Analysis of fHBP-FAT1 Expression on the Surface of *E. coli* BL21(DE3) ΔompA by FACS In order to confirm the ability of fHbp to deliver the FAT1 peptide on the outer membrane of *E. coli* ΔompA, FAT1 expression on the bacterial surface was analyzed by FACS.

BL21(DE3)/ΔompA (pET-fHbp-FAT1) and BL21(DE3)/ΔompA (pET-fHbpDomA-FAT1) *E. coli* strains were grown in 10 ml LB medium at 37 C and when the cultures reached $OD_{600}$=0.6, the expression of the fusion proteins was induced by addition of 1 mM IPTG. After 2 hour growth bacteria cells corresponding to those contained in 1 ml culture at $OD_{600}$=1 were collected by centrifugation at 13.000×g for 5 minutes and pellets were re-suspended in 50 ml of PBS containing 1% BSA. 50 µl of cell suspensions were incubated with 50 µl of an appropriate dilution of anti-FAT1 mAb198.3 or, as negative control, with 50 µl of PBS containing 1% BSA. After 1 hour, 100 µl of PBS containing 1% BSA were added and the suspensions were centrifuged at 3.000×g for 10 minutes and supernatants discarded. Pellets were washed with 200 µl of PBS containing 1% BSA and bacteria subsequently incubated for 30 minutes on ice with goat anti-mouse antibodies (Alexa flour488, Life Technology) added at a final dilution of 1:200. Finally, After 2 wash steps, pellets were re-suspended in 200 µl of PBS and analyzed with FACS CANTOII evaluating collected data with FlowJo software. As shown in FIG. 20, the FAT1 peptide, fused to fHbpDomA and fHbpFL, was clearly expressed on the surface of *E. coli* as indicated by the shift in fluorescence intensity observed after incubation of bacterial cells with anti-FAT1 specific monoclonal antibody.

Antibody Titers Elicited in Mice Immunized with fHbp-FAT1, fHbpDomA-FAT1 and MBP-FAT1 in Engineered OMVs To test whether OMVs purified from BL21(DE3)/ΔompA strain expressing fHbpFLFAT1, fHbpDomA-FAT1 and MBP-FAT1 were capable of inducing FAT1 peptide-specific antibody responses, groups of CD1 mice (5 mice per group) were i.p. immunized three times at two-week interval with 20 ug OMVs in Alum. After two weeks from the third immunization, sera were collected and pooled to analyze anti-FAT1 antibody titers by ELISA. ELISA was performed using plates coated with synthetic FAT1 peptide conjugated to the carrier protein Keyhole limpet hemocyanin (KLH). Coating was carried out at room temperature for 14 hours by adding to each well 100 µl of conjugated peptide at a concentration of 5 µg/ml. After three washes with 200 µl/well of PBS supplemented with 0.05% TWEEN 20 (PBST) the plates were incubated one hour at 37 C with 100 µl/well of PBS containing 1% BSA and subsequently washed three times with PBST. Different dilutions of sera in PBST containing 0.1% BSA were added in duplicate in a final volume of 100 µl/well and plates were stored at 37 C for 2 hours. After three washes in PBST, 100 µl of goat anti-mouse antibodies conjugated to alkaline phosphatase (SouthernBiotech, Cat. 1030-04, 1:2.000 dilution) were added to each well and incubated at 37 C for 1 hour. Finally, after three washes, the phosphatase substrate (4-Nitrophenyl phosphate disodium salt) was added to each well at a concentration of 1 mg/ml (100 ml/well) and after 30 minutes incubation at room temperature in the dark, substrate hydrolysis was measured spectrophotometrically at 405 nm. As shown in FIG. 23B, OMV engineered with FAT1 induced high concentrations of anti-FAT1 antibodies detectable even at serum dilutions higher them 1:24.000. In particular, OMV expressing fHbpFL-FAT1 and MBP-FAT1 induced antibodies titers which at the highest dilution (1:24.000) still gave saturating OD values similar to what observed with the anti-FAT1 mAb 198.3 which at 1:24.000 dilution corresponded to a concentration of 100 ng/ml. No significant titer against conjugated FAT1 was detected using sera from mice immunized with OMV engineered with the uncorrelated peptide MUC1.

Engineered OMVs Expressing MUC1 Peptide

Two strategies were designed to deliver the MUC1 peptide to *E. coli* OMVs. The first strategy was designed to deliver MUC1 peptide to the membrane of the vesicles by fusing MUC1 to the C-terminus of fHbpDomA. To achieve this, a synthetic DNA fragment encoding five copies of the MUC1 peptide GVTSAPDTRPAPGSTAPPAH (SEQ ID NO:7) was ligated to the 3' end of the gene coding for Domain A of fHbp (fHbpDomA).

The second strategy was designed to deliver the MUC1 peptide into the lumen of OMVs. To this aim, the synthetic DNA coding for five copies of the peptide was fused to the 3' end of the MBP gene to create an in frame C-terminal fusion.

OMV Engineering with fHbpDomA MUC1 Peptide

The fusion of five copies of the MUC1 peptide to fHbp-DomA was carried out in two main steps. First, the DNA fragment encoding fHbp-DomA were cloned into plasmid pET21 thus generating plasmid pET21_fHbp-DomA as already described. Subsequently, the plasmid was linearized by PCR and ligated to the synthetic DNA fragment encoding five copies of MUC1 peptide (MUC1 Minigene). The sequence coding for MUC1 Minigene was designed taking into consideration the *E. coli* codon usage. More specifically, pET21_fHbp-DomA was generated as follows. The fHbpDomA gene was amplified by PCR from *Neisseria meningitidis* serogroup B strain MC58 genome. The primers were designed to amplify the gene with its natural leader sequence for secretion and the lipobox. The polymerase incomplete primer extension (PIPE) cloning method (Klock H. et al., 2009) was used to insert the PCR product into plasmid pET21b which was amplified using primers pet-rev/nohisflag (Table 2). In so doing plasmid pET21_fHbp-DomA was generated (see also above for additional details).

To generate pET21_fHbp-DomA-FAT1 plasmid the PIPE cloning method was used. pET21_fHbp-DomA was linearized by PCR amplification using primers FHBP-F and FHBPDA-R (Table 2) and the linear fragment was combined with the synthetic DNA coding for MUC1 Minigene (Table 2 and Sequence 22). MUC1 Minigene was constructed by assembling ten complementary oligonucleotides the sequence of which is reported in Table 3 and the assembled DNA fragment was amplified with primers RMUCFH and FMUCDomA (Table 3) to make its extremities complementary to the amplified vector. The DNA mixture was then used to transform *E. coli* HK100 competent cells and clones carrying pET21_fHbp-DomA-MUC1 plasmid were selected on LB agar plates supplemented with 100 µg/ml Amplicillin. From one clone the plasmid was purified and the correctness of the fHbpDomA-MUC1 gene fusion was verified by DNA sequencing (SEQ ID NO:107).

pET-MBP-MUC1 Plasmid Construction

To express MUC1 peptide in the lumen of OMVs, the Maltose binding protein (MBP) which is naturally delivered to the periplasm was used as a carrier and the MUC1 Minigene was cloned as an in frame fusion to the 3' end of the MBP gene. For this purpose, plasmid pET-MBPvIII (see Section 5.1.3) has been used as template for a PCR reaction carried out according to the PIPE method (Klock H. E. and Lesley S. A (2009) Methods Mol. Biol. 498, 91-103), using primers pET21-MBPF and pET21-MBPR (see Table 2) to generate a linear fragment missing the vIII coding sequence. Then, the linear fragment was ligated to MUC1 Minigene constructed as described above and amplified with primers MBPMU-F and MBPMU-R (Table 3) to make its extremities complementary to the amplified vector. The DNA mixture was then used to transform *E. coli* HK100 competent cells and clones carrying pET21 MBP-MUC1 plasmid were selected on LB agar plates supplemented with 100 µg/ml Amplicillin. From one clone the plasmid was purified and the correctness of the MBP-MUC1 gene fusion was verified by DNA sequencing (SEQ ID NO:108).

TABLE 3

| \multicolumn{2}{c}{Synthetic oligonucleotides used for assembling the MUC1 Minigene coding from 5 copies of MUC1} | |
|---|---|
| F1-MUC | GGGGTGACGAGCGCGCCAGATACACGTCCGGCTCCT<br>(SEQ ID NO: 131) |
| R1-MUC | ATGCGCCGGCGGGGCCGTCGAGCCAGGAGCCGGACG<br>(SEQ ID NO: 132) |
| F2-MUC | CCGCCGGCGCATGGAGTAACGTCAGCACCAGACACGCGCC<br>CG<br>(SEQ ID NO: 133) |
| R2-MUC | GTGGGCAGGGGGAGCGGTGGATCCCGGTGCCGGGCGCG<br>TGTC<br>(SEQ ID NO: 134) |
| F3-MUC | CCCCCTGCCCACGGTGTTACTAGTGCGCCCGATACCCGT<br>CCA<br>(SEQ ID NO: 135) |
| R3-MUC | ATGCGCCGGCGGCGCGGTGGAGCCCGGTGCTGGACGGG<br>TATC<br>(SEQ ID NO: 136) |
| F4-MUC | CCGCCGGCGCATGGAGTCACGTCAGCACCGGACACTCGT<br>CCA<br>(SEQ ID NO: 137) |
| R4-MUC | GTGTGCTGGAGGCGCGGTTGAACCCGGGGCTGGACGAGT<br>GTC<br>(SEQ ID NO: 138) |
| F5-MUC | CCTCCAGCACACGGCGTCACCTCAGCTCCAGATACGCGC<br>CCG<br>(SEQ ID NO: 139) |
| R5-MUC | ATGTGCCGGCGGAGCGGTACTGCCTGGGGCCGGGCGCGT<br>ATC<br>(SEQ ID NO: 140) |
| \multicolumn{2}{c}{Primers used to insert MUC1 Minigene into pET21_fHbpDomA and pET21_MBP} | |
| R-MUCFH | GTGATGGTGATGGTGATGTTAATGCGCCGGCGGAGC<br>(SEQ ID NO: 141) |
| F-MUCDomA | CAAGTATACAAACAAGGGGTGACGAGCGCG<br>(SEQ ID NO: 142) |
| MBPMU-F | CGCGCAGACTCGTATCACCAAGGGGGTGACGAGCGCG<br>(SEQ ID NO: 143) |
| MBPMU-R | TCGTGATGGTGATGGTGATGTTAATGCGCCGGCGGAGC<br>(SEQ ID NO: 144) |

Expression of fHbpDomA-MUC1 and MBP-MUC1 Fusions in E. coli BL21(DE3) ΔompA

Plasmids pET21_fHbp-DomA-MUC1 and pET-MBP-MUC1 were used to transform BL21(DE3) ΔompA strain. Recombinant clones were grown in 200 ml LB medium at 37 C and when the cultures reached OD600=0.6, the expression of the fusion proteins was induced by addition of 1 mM IPTG. After 2 hour growth, the expression of protein fusions was assessed by SDS-PAGE. To this aim, the equivalent in volume of 1 $OD_{600}$ of bacteria culture was collected, centrifuged at 13.000× g for 5 minutes and pellets were lysed in 200 μl of BPer Reagent, Lysozime 1 mg/ml, DNAase 10U/ml and 0.1 mM $MgCl_2$ for 30 minutes. Then the samples were centrifuged at 13.000×g for 20 minutes to separate the supernatants (soluble fraction) from the pellets (insoluble fraction). The soluble fractions were collected (200 ul) and diluted with 100 μl of 4× SDS-PAGE loading buffer while the pellets were re-suspended in 300 μl of 2× loading buffer. 20 μl of each sample were loaded onto an SDS-polyacrylamide gel and proteins separated by electrophoresis (SDS-PAGE). Then the gel was stained with COOMASSIE blue overnight at room temperature. As shown in FIG. 21, protein species with apparent molecular mass corresponding fHbpDomA-MUC1 and MBP-MUC1 were visible after COOMASSIE Blue staining of SDS-polyacrylamide gels. The proteins largely compartmentalized in the insoluble fractions and were expressed after IPTG induction.

Compartmentalization of fHbpDomA-MUC1 and MBP-MUC1 Fusions into OMVs

Having demonstrated that fHbpDomA-MUC1 and MBP-MUC1 were expressed in E. coli BL21(DE3)/ΔompA, the presence of the fusions in the OMV compartment was analyzed. To this aim, 200 ml of the bacterial cultures BL21(DE3)/ΔompA (pET-fHbpDomA-MUC1) and BL21 (DE3)/ΔompA (pET-MBP-MUC1) were grown in LB and when the cultures reached an $OD_{600}$=0.6 were induced with 1 mM IPTG. Vesicles were purified from the culture supernatants by using ultrafiltration coupled to ultracentrifugation. Briefly, cultures were centrifuged at 4.000×g for 15 min, and the supernatants were concentrated using a membrane with a cut off of 100 kDA (Amicon) until a final volume of 30 ml was reached. Then an ultracentrifugation step was performed at 160.000×g for 2 hours. The pellets were re-suspended in 200 μl of PBS. Protein quantization was performed by DC Protein Assay (BioRad). The presence of the fusion proteins in the OMVs preparation was verified by SDS-PAGE analysis as already described by loading 10 μg of total proteins of each OMV preparation. As shown in FIG. 22, the two fusion constructs compartmentalized in OMVs as indicated by the appearance of protein bands corresponding to the expected molecular mass.

Antibody Titers Elicited in Mice Immunized with Engineered OMVs Carrying fHbpDomA-MUC1 and MBP-MUC1

To test whether OMVs purified from BL21(DE3)/ΔompA (pET-fHbpDomA-MUC1) and BL21(DE3)/ΔompA (pET-MBP-MUC1) strains were capable of inducing MUC1-specific antibody responses, CD1 mice (5 mice per group) were i.p. immunized three times at two-week intervals with 20 μg of engineered OMVs in Alum. After two weeks from the third immunization, sera were collected and pooled to analyze anti-MUC1 antibody titers by ELISA. ELISA was performed using plates coated with the synthetic MUC1 peptide GVTSAPDTRPAPGSTAPPAH (SEQ ID NO:7). Coating was carried out at room temperature for 14 hours by adding to each well 100 μl of a solution of synthetic MUC1 peptide at a concentration of 5 μg/ml. After three washes with 200 μl/well of PBS supplemented with 0.05% TWEEN 20 (PBST) the plates were incubated one hour at 37 C with 100 μl/well of PBS containing 1% BSA and subsequently washed three times with PBST. Different dilutions of sera in PBST containing 0.1% BSA were added in duplicate in a final volume of 100 μl/well and plates were stored at 37 C for 2 hours. After three washes in PBST, 100 μl of goat anti-mouse antibodies conjugated to alkaline phosphatase (SouthernBiotech, Cat. 1030-04, 1:2.000 dilution) were added to each well and incubated at 37 C for 1 hour. Finally, after three washes, the phosphatase substrate (4-Nitrophenyl phosphate disodium salt) was added to each well at a concentration of 1 mg/ml (100 μl/well) and after 30 minute incubation at room temperature in the dark, substrate hydrolysis was measured spectrophotometrically at 405 nm. As shown in FIG. 23A, OMV engineered with MUC1 induced high concentrations of anti-MUC1 antibodies detectable even at serum dilutions higher them 1:24.000. In particular, both engineered OMV expressing fHbpDomA-MUC1 and MBP-MUC1 induced antibodies titers which at the highest dilution (1:24.000) still gave saturating OD values. No relevant titers against MUC1 peptide was detected using sera from mice immunized with OMV engineered with the uncorrelated peptide FAT1.

Engineered OMVs Expressing Aa-fHbp pET-Aa-fHbp-HIS8 Plasmid Construction

The gene encoding the 828 bp lipoprotein gna1870 like-protein was chemically synthetized (GeneArt™ Gene Synthesis, Thermo Fisher Scientific) using the reported gene sequence (EnsemblBacteria gene ID HMPREF9996_00541) from Aggregatibacter actinomycetemcomitans Y4 with the exception that the natural GTG start codon was replaced by an ATG start codon. The synthetic gene (SEQ ID NO:116) was cloned into pET21b⁺ fused to a 8-HIS tag at the C-term for subsequent detection of the protein using an anti-HIS polyclonal antibody. For cloning: the synthetic gene was amplified by PCR using the AgfHbp_F and AgfHbp_R primers, and annealed to pET21b⁺ plasmid backbone amplified with pET HIS-F and pET 2-R primers (Table1).

Expression of the Aa-fHbp Heterologous Protein in E. coli BL21(DE3)/ΔompA Strain To investigate whether Aa-fHbp was surface-associated when expressed in E. coli, the pET Aa-fHbp-Hiss recombinant plasmid was used to transform E. coli BL21ΔompA and the expression and localization of Aa-fHbp was analyzed as described previously. Each strain was grown in LB medium and when cultures reached an $OD_{600}$ value of 0.6, IPTG was added at 1 mM final concentration. After two additional hours of growth at 37° C., cells were collected and total protein extracts were analyzed by SDS-PAGE followed by COOMASSIE staining. No bands were visible in total lysates from E. coli cells carrying empty pET21 plasmid. A band corresponding to the Aa-fHbp protein is detected in the total lysate of the strain carrying the pET Aa-fHbp-Hiss recombinant plasmid as detected by COOMASSW.

Analysis of Aa-fHbp Expression in OMVs

Figure 24:
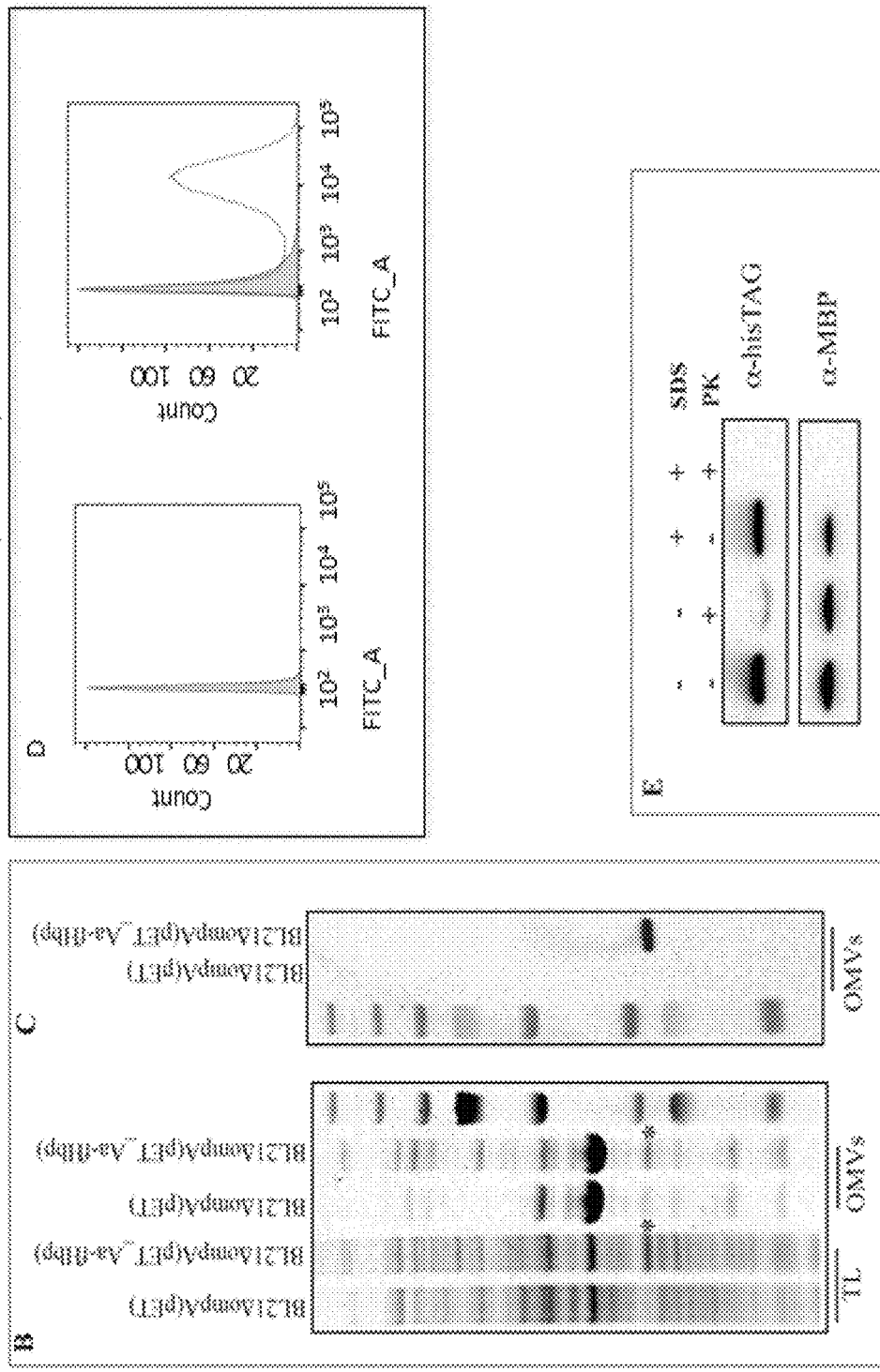

Having demonstrated that the exogenous Aa-fHbp protein was well expressed in E. coli BL21(DE3)/ΔompA strain, we then analysed its cellular localization and compartmentalization to the OMV fraction. The recombinant strain BL21 (DE3)/ΔompA(pETAa-fHbp-HIS8) was grown in LB medium and when the cultures reached an $OD_{600}$ value of 0.6, IPTG was added at 1 mM final concentration. After two additional hours of growth at 37° C., vesicles were purified from culture supernatants by using ultrafiltration coupled to ultracentrifugation. More specifically, OMVs were collected from culture supernatants by filtration through a 0.22 μm pore size filter (Millipore) and by high-speed centrifugation (200.000×g for 2 hours). Pellets containing OMVs were finally suspended in PBS. The presence of the Aa-fHbp HIS8 fusion protein in OMVs preparations was verified by COOMASSIE and Western Blot analysis as described in the previous section (FIG. 24). Data indicate that the recombinant protein was incorporated into OMVs as shown by the presence of the corresponding correct molecular weight band in the COOMASSIE stained SDS-PAGE and a specular specific band in the western blot analysis probed by anti-His tag antibody.

Analysis of Cellular Localization of Aa-fHbp

The localization of recombinant Aa-fHbp protein was evaluated by flow cytometry. To this aim, recombinant E. coli strains BL21(DE3)/ΔompA(pET-Aa-fHbp-HIS8) and E. coli BL21(DE3)/ΔompA(pET21), as negative control, were grown at 37° C. under agitation. When cultures reached an $OD_{600}$ value of 0.6, IPTG was added at a final concentration of 1 mM and bacteria were grown for 2 additional hours. Subsequently, bacteria cells corresponding to those contained in 1 ml culture at $OD_{600}$=1 were collected by centrifugation at 13,000×g for 5 minutes and pellets were re-suspended in 50 ml of PBS containing 1% BSA. 50 μl of cell suspensions were incubated with 50 μl of an appropriate dilution of anti-His-tag antibody with 50 μl of PBS containing 1% BSA as negative control. After 1 hour, 100 μl of PBS containing 1% BSA were added and the suspensions were centrifuged at 3,000×g for 10 minutes and supernatants discarded. Pellets were washed with 200 μl of PBS containing 1% BSA and bacteria subsequently incubated for 30 minutes on ice with goat anti-mouse antibodies (Alexa flour488, Life Technology) added at a final dilution of 1:2,000. Finally, After 2 wash steps, pellets were re-suspended in 200 μl of PBS and analyzed with FACS CANTOII evaluating collected data with FlowJo software. As shown in FIG. 24, in the presence of anti-his-tag antibody, a clear shift in fluorescence intensity was observed in a substantial fraction of bacterial cells expressing Aa-fHbp-HIS8 fusion protein. No difference in fluorescence intensity was observed when E. coli BL21(DE3)/ΔompA were incubated with anti-his-tag antibody. Taken together these data indicate not only that AafHbp is expressed in E. coli BL21(DE3)/ΔompA and is associated to the outer membrane but is also capable of exposing a foreign tag fused to its C-terminal portion to the extracellular compartment.

The invention claimed is:

1. An isolated bacterial outer membrane vesicle comprising a fusion protein, wherein the fusion protein comprises an isolated bacterial protein fused to one or more copies of an immunogenic tumor antigen protein, wherein the isolated bacterial protein is selected from the group consisting of *Neisseria meningitidis* factor H binding protein (fHbp) of SEQ ID NO: 1, *Neisseria meningitidis* NHBA of SEQ ID NO: 109, *Escherichia coli* outer membrane protein-F (OmpF) of SEQ ID NO: 3, and *Aggregatibacter actinomycetemcomitans* factor H binding protein (Aa-fHbp) of SEQ ID NO: 110.

2. The isolated bacterial outer membrane vesicle of claim 1, wherein the outer membrane vesicle is secreted by *Escherichia coli*.

3. The isolated bacterial outer membrane vesicle of claim 1, wherein the one or more copies of the immunogenic tumor antigen protein in the fusion protein is selected from hEGFRvIII, hFAT-1 and hMUC-1 or an immunogenic fragment thereof.

4. The isolated bacterial outer membrane vesicle of claim 3, wherein the immunogenic fragment of the hEGFRvIII is LEEKKGNYVVTDH (SEQ ID NO: 5).

5. The isolated bacterial outer membrane vesicle of claim 3, wherein the immunogenic fragment of the hFAT-1 is IQVEATDKDLGPNGHVTYSIVTDTD (SEQ ID NO: 6).

6. The isolated bacterial outer membrane vesicle of claim 3, wherein the immunogenic fragment of the hMUC-1 is GVTSAPDTRPAPGSTAPPAH (SEQ ID NO: 7).

7. An immunogenic composition comprising the isolated bacterial outer membrane vesicle of claim 1.

8. The immunogenic composition of claim 7 further comprising pharmaceutically acceptable excipients and adjuvants.

9. The immunogenic composition of claim 7, wherein the bacterial outer membrane vesicle is purified and the immunogenic composition is in the form of a cancer vaccine.

10. An immunogenic composition comprising a mixture of isolated bacterial outer membrane vesicles each comprising a fusion protein, wherein the fusion protein comprises an isolated bacterial protein fused to an immunogenic tumor antigen protein, wherein the isolated bacterial protein is selected from the group consisting of *Neisseria meningitidis* factor H binding protein (fHbp) of SEQ ID NO: 1, *Neisseria meningitidis* NHBA of SEQ ID NO: 109, *Escherichia coli* outer membrane protein-F (OmpF) of SEQ ID NO: 3, and *Aggregatibacter actinomycetemcomitans* factor H binding protein (Aa-fHbp) of SEQ ID NO: 110 and wherein each of the bacterial outer membrane vesicle differs from the other in the type of the immunogenic tumor antigen protein comprised in the fusion protein.

* * * * *